United States Patent
Hartwell et al.

(10) Patent No.: US 11,638,666 B2
(45) Date of Patent: May 2, 2023

(54) COMPOSITION, APPARATUS, KIT AND METHOD AND USES THEREOF

(71) Applicant: Smith & Nephew PLC, Watford (GB)

(72) Inventors: Edward Yerbury Hartwell, Hull (GB); Christopher John Fryer, York (GB); Sarah Jenny Collinson, York (GB); Marcus Damian Phillips, Wakefield (GB)

(*) Notice: Subject to any disclaimer, the term of this patent is extended or adjusted under 35 U.S.C. 154(b) by 771 days.

(21) Appl. No.: 15/654,524

(22) Filed: Jul. 19, 2017

(65) Prior Publication Data
US 2018/0010025 A1    Jan. 11, 2018

Related U.S. Application Data

(63) Continuation of application No. 14/360,591, filed as application No. PCT/GB2012/000866 on Nov. 26, 2012, now abandoned.

(30) Foreign Application Priority Data

Nov. 25, 2011 (GB) ........................... 1120454
May 30, 2012 (GB) ........................... 1209619

(51) Int. Cl.
*A61M 1/00* (2006.01)
*A61F 13/00* (2006.01)
(Continued)

(52) U.S. Cl.
CPC ....... *C09J 183/00* (2013.01); *A61F 13/00063* (2013.01); *A61F 13/00068* (2013.01);
(Continued)

(58) Field of Classification Search
CPC ......... A61M 1/00; A61M 27/00; A61F 13/00; A61F 13/02; A61F 13/00063;
(Continued)

(56) References Cited

U.S. PATENT DOCUMENTS 3,274,155 A    9/1966    Saunders et al.
3,646,155 A    2/1972    Scott et al.
(Continued)

FOREIGN PATENT DOCUMENTS

CN    1805761 A    5/2010
CN    101730524 A    6/2010
(Continued)

OTHER PUBLICATIONS

US 6,216,701 B1, 04/2001, Heaton et al. (withdrawn)
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

A curable composition for use in wound care comprising, apportioned between at least one Part A and at least one Part B: one or more alkenyl-group containing polymers (i) having at least one alkenyl group or moiety per molecule, one or more SiH-containing polymers (ii) having at least one Si—H unit per molecule; and a catalyst (iii) for curing by addition of alkenyl-containing polymer (i) to SiH-containing polymer (ii), Part A and Part B independently having viscosity at 23° C. in the range 5-300 Pa·s, preferably 10-100 Pa·s, at a shearing rate of 10 s$^{-1}$, and when combined in one Part having cure time at 23° C. in the range from 0.5 min to 25 min, wherein when dispensed into a location about a wound dressing, said wound dressing overlying a wound site and skin thereabout, said dispensing being so as to intimately contact and overlie an edge of said dressing and skin about said edge, the composition cures in contact with said edge and skin at 32° C. to an elastomer exhibiting zero or low tack at a time in the range from 0.5 to less than 30 minutes, apparatus for use with said composition comprising (Continued)

dispensing apparatus or wound dressing, a kit comprising the same, and methods of dispensing and curing the same and of using the same in sealing a wound dressing and in treating a wound site of a human in need thereof.

19 Claims, 13 Drawing Sheets

(51) Int. Cl.
  *A61F 13/02* (2006.01)
  *C09J 183/00* (2006.01)
  *A61F 17/00* (2006.01)
  *A61L 15/22* (2006.01)
  *A61L 15/42* (2006.01)
  *A61L 15/58* (2006.01)
  *A61M 5/19* (2006.01)
  *C09J 201/02* (2006.01)
  *A61M 27/00* (2006.01)
  *A61K 9/22* (2006.01)

(52) U.S. Cl.
  CPC .......... *A61F 13/0216* (2013.01); *A61F 17/00* (2013.01); *A61L 15/225* (2013.01); *A61L 15/42* (2013.01); *A61L 15/585* (2013.01); *A61M 1/90* (2021.05); *A61M 5/19* (2013.01); *C09J 201/02* (2013.01)

(58) Field of Classification Search
  CPC . A61F 13/00068; A61F 13/0216; A61K 9/22; A61L 15/225; A61L 15/585
  See application file for complete search history.

(56) References Cited

U.S. PATENT DOCUMENTS

| | | |
|---|---|---|
| 3,783,870 A | 1/1974 | Schachet |
| 3,808,178 A | 4/1974 | Gaylord |
| 3,809,086 A | 5/1974 | Schachet et al. |
| 3,809,087 A | 5/1974 | Lewis, Jr. |
| 3,928,629 A | 12/1975 | Chandra et al. |
| 3,972,328 A | 8/1976 | Chen |
| 4,073,294 A | 2/1978 | Stanley et al. |
| 4,117,551 A | 9/1978 | Books et al. |
| 4,266,545 A | 5/1981 | Moss |
| 4,278,089 A | 7/1981 | Huck et al. |
| 4,392,860 A | 7/1983 | Huck et al. |
| 4,529,553 A | 7/1985 | Faltynek |
| 4,538,920 A | 9/1985 | Drake et al. |
| 4,569,674 A | 2/1986 | Phillips |
| 4,578,060 A | 3/1986 | Huck et al. |
| 4,655,754 A | 4/1987 | Richmond et al. |
| 4,661,093 A | 4/1987 | Beck et al. |
| 4,713,052 A | 12/1987 | Beck et al. |
| 4,714,739 A | 12/1987 | Arkles |
| 4,720,431 A | 1/1988 | Wong |
| 4,728,499 A | 3/1988 | Fehder |
| 4,753,536 A | 6/1988 | Spehar et al. |
| 4,767,026 A | 8/1988 | Keller |
| 4,771,919 A | 9/1988 | Ernst |
| 4,791,149 A | 12/1988 | Pocknell |
| 4,798,583 A | 1/1989 | Beck et al. |
| 4,813,942 A | 3/1989 | Alvarez |
| 4,826,494 A | 5/1989 | Richmond et al. |
| 4,838,253 A | 6/1989 | Brassington et al. |
| 4,872,450 A | 10/1989 | Austad |
| 4,923,444 A | 5/1990 | Daoud et al. |
| 4,936,834 A | 6/1990 | Beck et al. |
| 4,969,880 A | 11/1990 | Zamierowski |
| 4,991,574 A | 2/1991 | Pocknell |
| 5,004,643 A | 4/1991 | Caldwell |
| 5,010,115 A | 4/1991 | Grisoni |
| 5,033,650 A | 7/1991 | Colin et al. |
| 5,056,510 A | 10/1991 | Gilman |
| 5,064,653 A | 11/1991 | Sessions et al. |
| 5,080,493 A | 1/1992 | McKown et al. |
| 5,089,606 A | 2/1992 | Cole et al. |
| 5,100,395 A | 3/1992 | Rosenberg |
| 5,141,503 A | 8/1992 | Sewell, Jr. |
| 5,145,933 A | 9/1992 | Grisoni et al. |
| 5,153,231 A | 10/1992 | Bouquet et al. |
| 5,181,905 A | 1/1993 | Flam |
| 5,238,732 A | 8/1993 | Krishnan |
| 5,249,709 A | 10/1993 | Duckworth et al. |
| 5,266,326 A | 11/1993 | Barry et al. |
| 5,333,760 A | 8/1994 | Simmen et al. |
| 5,348,392 A | 9/1994 | Bouquet et al. |
| 5,397,848 A | 3/1995 | Yang et al. |
| 5,456,745 A | 10/1995 | Rorefer et al. |
| 5,549,584 A | 8/1996 | Gross |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,636,643 A | 6/1997 | Argenta et al. |
| 5,645,081 A | 7/1997 | Argenta et al. |
| 5,660,823 A | 8/1997 | Chakrabarti et al. |
| 5,717,030 A | 2/1998 | Dunn et al. |
| 5,747,064 A | 5/1998 | Burnett et al. |
| 5,759,570 A | 6/1998 | Arnold |
| 5,776,193 A | 7/1998 | Kwan et al. |
| 5,834,007 A | 11/1998 | Kubota |
| 5,840,777 A | 11/1998 | Eagles et al. |
| 5,852,126 A | 12/1998 | Barnard et al. |
| 5,874,500 A | 2/1999 | Rhee et al. |
| D406,899 S | 3/1999 | Cottle |
| RE36,235 E | 6/1999 | Keller et al. |
| 5,944,703 A | 8/1999 | Dixon et al. |
| 5,945,115 A | 8/1999 | Dunn et al. |
| 5,962,010 A | 10/1999 | Greff et al. |
| 5,998,472 A | 12/1999 | Berger et al. |
| 6,022,904 A | 2/2000 | Sollradl et al. |
| 6,024,731 A | 2/2000 | Seddon et al. |
| 6,065,270 A | 5/2000 | Reinhard et al. |
| 6,071,267 A | 6/2000 | Zamierowski |
| 6,121,341 A | 9/2000 | Sawhney et al. |
| 6,135,116 A | 10/2000 | Vogel et al. |
| D434,150 S | 11/2000 | Tumey et al. |
| 6,142,982 A | 11/2000 | Hunt et al. |
| 6,143,352 A | 11/2000 | Clark et al. |
| 6,165,201 A | 12/2000 | Sawhney et al. |
| 6,168,788 B1 | 1/2001 | Wortham |
| D439,341 S | 3/2001 | Tumey et al. |
| 6,214,332 B1 | 4/2001 | Askill et al. |
| 6,252,129 B1 | 6/2001 | Coffee |
| 6,261,276 B1 | 7/2001 | Reitsma |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,447,802 B2 | 9/2002 | Sessions et al. |
| 6,458,109 B1 | 10/2002 | Henley et al. |
| 6,471,685 B1 | 10/2002 | Johnson |
| 6,486,285 B2 | 11/2002 | Fujita |
| 6,495,127 B1 | 12/2002 | Wallace et al. |
| 6,509,031 B1 | 1/2003 | Miller et al. |
| 6,521,251 B2 | 2/2003 | Askill et al. |
| 6,527,203 B2 | 3/2003 | Hurray et al. |
| 6,547,467 B2 | 4/2003 | Quintero |
| 6,553,998 B2 | 4/2003 | Heaton et al. |
| 6,564,972 B2 | 5/2003 | Sawhney et al. |
| 6,569,113 B2 | 5/2003 | Wirt et al. |
| 6,575,940 B1 | 6/2003 | Levinson et al. |
| 6,596,704 B1 | 7/2003 | Court et al. |
| 6,626,891 B2 | 9/2003 | Ohmstede |
| 6,627,216 B2 | 9/2003 | Brandt et al. |
| 6,629,774 B1 | 10/2003 | Guruendeman |
| 6,648,852 B2 | 11/2003 | Wirt et al. |
| 6,648,862 B2 | 11/2003 | Watson |
| 6,685,681 B2 | 2/2004 | Lockwood et al. |
| 6,695,823 B1 | 2/2004 | Lina et al. |
| 6,698,622 B2 | 3/2004 | Sawhney et al. |
| 6,730,299 B1 | 5/2004 | Tayot et al. |

(56) References Cited

U.S. PATENT DOCUMENTS

| | | |
|---|---|---|
| 6,732,887 B2 | 5/2004 | Bills |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,776,769 B2 | 8/2004 | Smith |
| 6,790,438 B1 | 9/2004 | Constancis et al. |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,840,462 B2 | 1/2005 | Hurray et al. |
| 6,855,135 B2 | 2/2005 | Lockwood et al. |
| 6,856,821 B2 | 2/2005 | Johnson |
| 6,926,695 B2 | 8/2005 | Levinson et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,128,735 B2 | 10/2006 | Weston |
| 7,129,210 B2 | 10/2006 | Lowinger et al. |
| 7,132,170 B2 | 11/2006 | Parker |
| 7,175,336 B2 | 2/2007 | Voellmicke et al. |
| 7,216,651 B2 | 5/2007 | Argenta et al. |
| 7,279,612 B1 | 10/2007 | Heaton et al. |
| 7,303,757 B2 | 12/2007 | Schankereli et al. |
| 7,316,330 B2 | 1/2008 | Muller et al. |
| 7,361,184 B2 | 4/2008 | Joshi |
| 7,381,859 B2 | 6/2008 | Hunt et al. |
| 7,387,432 B2 | 6/2008 | Lu et al. |
| 7,396,507 B2 | 7/2008 | Grunwald et al. |
| 7,524,315 B2 | 4/2009 | Blott et al. |
| 7,534,927 B2 | 5/2009 | Lockwood |
| 7,543,843 B2 | 6/2009 | Keshavaraj et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,635,343 B2 | 12/2009 | Mcintosh et al. |
| 7,674,837 B2 | 3/2010 | Gaserod et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,708,940 B2 | 5/2010 | Grunwald et al. |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |
| 7,749,531 B2 | 7/2010 | Booher |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,862,831 B2 | 1/2011 | Wang et al. |
| 7,882,983 B2 | 2/2011 | Reidt et al. |
| 7,910,135 B2 | 3/2011 | St. John et al. |
| 7,910,791 B2 | 3/2011 | Coffey |
| 7,919,182 B2 | 4/2011 | Hamada et al. |
| 7,922,703 B2 | 4/2011 | Riesinger |
| 7,922,743 B2 | 4/2011 | Heinrich et al. |
| 7,927,318 B2 | 4/2011 | Risk, Jr. et al. |
| 7,954,672 B2 | 6/2011 | Keller |
| 7,959,624 B2 | 6/2011 | Riesinger |
| 7,964,766 B2 | 6/2011 | Blott et al. |
| 7,976,519 B2 | 7/2011 | Bubb et al. |
| 8,007,164 B2 | 8/2011 | Tatsunosuke et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,331 B2 | 11/2011 | Zamierowski |
| 8,074,843 B2 | 12/2011 | Keller |
| 8,080,702 B2 | 12/2011 | Blott et al. |
| 8,096,979 B2 | 1/2012 | Lina et al. |
| 8,100,887 B2 | 1/2012 | Weston et al. |
| 8,118,794 B2 | 2/2012 | Weston et al. |
| 8,119,160 B2 | 2/2012 | Looney et al. |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,207,392 B2 | 6/2012 | Haggstrom et al. |
| 8,225,981 B2 | 7/2012 | Criscuolo et al. |
| 8,226,942 B2 | 7/2012 | Charier et al. |
| 8,235,972 B2 | 8/2012 | Adahan |
| 8,241,261 B2 | 8/2012 | Randolph et al. |
| 8,267,918 B2 | 9/2012 | Johnson et al. |
| 8,273,368 B2 | 9/2012 | Ambrosio et al. |
| 8,282,611 B2 | 10/2012 | Weston |
| 8,286,832 B2 | 10/2012 | Keller |
| 8,303,552 B2 | 11/2012 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,410,189 B2 | 4/2013 | Carnahan et al. |
| 8,425,478 B2 | 4/2013 | Olson |
| 8,444,612 B2 | 5/2013 | Patel et al. |
| 8,444,613 B2 * | 5/2013 | Svedman ............ A61M 1/0031 424/447 |
| 8,454,580 B2 | 6/2013 | Locke et al. |
| 8,460,255 B2 | 6/2013 | Joshi et al. |
| 8,481,801 B2 | 7/2013 | Addison et al. |
| 8,535,296 B2 | 9/2013 | Blott et al. |
| 8,540,699 B2 | 9/2013 | Miller et al. |
| 8,545,466 B2 | 10/2013 | Andresen et al. |
| 8,613,734 B2 | 12/2013 | Lina et al. |
| 8,628,505 B2 | 1/2014 | Weston |
| 8,641,691 B2 | 2/2014 | Fink |
| 8,663,198 B2 | 3/2014 | Buan et al. |
| 8,708,998 B2 | 4/2014 | Weston et al. |
| 8,715,256 B2 | 5/2014 | Greener |
| 8,753,670 B2 | 6/2014 | Delmotte |
| 8,764,732 B2 | 7/2014 | Hartwell |
| 8,791,316 B2 | 7/2014 | Greener |
| 8,795,243 B2 | 8/2014 | Weston |
| 8,795,635 B2 | 8/2014 | Tamarkin et al. |
| 8,795,713 B2 | 8/2014 | Makower et al. |
| 8,795,800 B2 | 8/2014 | Evans |
| 8,801,685 B2 | 8/2014 | Armstrong et al. |
| 8,808,274 B2 | 8/2014 | Hartwell |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,894,620 B2 | 11/2014 | Swain |
| 8,916,742 B2 | 12/2014 | Smith |
| 8,956,336 B2 | 2/2015 | Haggstrom et al. |
| 8,968,773 B2 | 3/2015 | Thomas et al. |
| 8,998,866 B2 | 4/2015 | Hicks |
| 9,012,714 B2 | 4/2015 | Fleischmann |
| 9,028,872 B2 | 5/2015 | Gaserod et al. |
| 9,061,095 B2 | 6/2015 | Adie et al. |
| 9,067,003 B2 | 6/2015 | Buan et al. |
| 9,173,777 B2 | 11/2015 | Zurovcik |
| 9,199,012 B2 | 12/2015 | Vitaris et al. |
| 9,220,822 B2 | 12/2015 | Hartwell et al. |
| 9,254,353 B2 | 2/2016 | Locke et al. |
| 9,387,126 B2 | 7/2016 | Blott et al. |
| 9,421,309 B2 | 8/2016 | Robinson et al. |
| 9,427,505 B2 | 8/2016 | Askem et al. |
| 9,446,178 B2 | 9/2016 | Blott et al. |
| 9,474,661 B2 | 10/2016 | Fouillet et al. |
| 9,492,326 B2 | 11/2016 | Miller et al. |
| 9,629,986 B2 | 4/2017 | Patel et al. |

(56) References Cited

U.S. PATENT DOCUMENTS

| | | |
|---|---|---|
| 9,682,179 B2 | 6/2017 | May |
| 10,046,096 B2 | 8/2018 | Askem et al. |
| 10,070,994 B2 | 9/2018 | Dodd et al. |
| 2001/0004082 A1 | 6/2001 | Keller et al. |
| 2001/0043913 A1 | 11/2001 | Spaans et al. |
| 2002/0010299 A1 | 1/2002 | Guyuron et al. |
| 2002/0017304 A1 | 2/2002 | Heaton et al. |
| 2002/0038826 A1 | 4/2002 | Hurray et al. |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0146662 A1 | 10/2002 | Radl et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0069535 A1 | 4/2003 | Shalaby |
| 2003/0069563 A1 | 4/2003 | Johnson |
| 2003/0093041 A1 | 5/2003 | Risk, Jr. et al. |
| 2003/0125646 A1 | 7/2003 | Whitlock |
| 2003/0143189 A1 | 7/2003 | Askill et al. |
| 2003/0183653 A1 | 10/2003 | Bills |
| 2003/0212357 A1 | 11/2003 | Pace |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0057855 A1 | 3/2004 | Gerlach et al. |
| 2004/0073152 A1 | 4/2004 | Karason et al. |
| 2004/0084812 A1 | 5/2004 | Grunwald et al. |
| 2004/0121438 A1 | 6/2004 | Quirk |
| 2004/0167617 A1 | 8/2004 | Voellmicke et al. |
| 2004/0171998 A1 | 9/2004 | Marasco, Jr. |
| 2005/0020955 A1 | 1/2005 | Sanders et al. |
| 2005/0085795 A1 | 4/2005 | Lockwood |
| 2005/0100692 A1 | 5/2005 | Parker |
| 2005/0137272 A1 | 6/2005 | Gaserod et al. |
| 2005/0163904 A1 | 7/2005 | Walker et al. |
| 2005/0230422 A1 | 10/2005 | Muller et al. |
| 2006/0009577 A1 | 1/2006 | Hara |
| 2006/0009744 A1 | 1/2006 | Edrman et al. |
| 2006/0079599 A1 | 4/2006 | Arthur |
| 2006/0100586 A1 | 5/2006 | Karpowicz |
| 2006/0173253 A1 | 8/2006 | Ganapathy et al. |
| 2006/0173514 A1 | 8/2006 | Biel et al. |
| 2006/0217016 A1 | 9/2006 | Lin et al. |
| 2006/0228318 A1 | 10/2006 | Fabo |
| 2006/0253082 A1 | 11/2006 | Mcintosh et al. |
| 2006/0273109 A1 | 12/2006 | Keller |
| 2007/0004896 A1 | 1/2007 | Ito et al. |
| 2007/0009580 A1 | 1/2007 | DiCosmo et al. |
| 2007/0040454 A1 | 2/2007 | Freudenberger et al. |
| 2007/0055209 A1 | 3/2007 | Patel et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185463 A1 | 8/2007 | Mulligan |
| 2007/0186404 A1 | 8/2007 | Drew et al. |
| 2007/0203062 A1 | 8/2007 | Ellis-Behnke et al. |
| 2007/0219513 A1 | 9/2007 | Lina et al. |
| 2007/0225663 A1 | 9/2007 | Watt et al. |
| 2007/0237811 A1 | 10/2007 | Scherr |
| 2007/0248642 A1 | 10/2007 | Dornish et al. |
| 2008/0004549 A1 | 1/2008 | Anderson et al. |
| 2008/0031748 A1 | 2/2008 | Ihle et al. |
| 2008/0060550 A1 | 3/2008 | MacDonald et al. |
| 2008/0089173 A1 | 4/2008 | Lu et al. |
| 2008/0132821 A1 | 6/2008 | Propp et al. |
| 2008/0206155 A1 | 8/2008 | Tamarkin et al. |
| 2008/0208163 A1 | 8/2008 | Wilkie |
| 2008/0232187 A1 | 9/2008 | Tatsunosuke et al. |
| 2008/0249259 A1 | 10/2008 | Kashiwagi |
| 2008/0254103 A1 | 10/2008 | Harris et al. |
| 2008/0279807 A1 | 11/2008 | Belcheva et al. |
| 2008/0287880 A1 | 11/2008 | Keller |
| 2008/0306456 A1 | 12/2008 | Riesinger |
| 2008/0314929 A1 | 12/2008 | Keller |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0093550 A1 | 4/2009 | Rolfes et al. |
| 2009/0098073 A1 | 4/2009 | MacDonald et al. |
| 2009/0098503 A1 | 4/2009 | Knispel et al. |
| 2009/0134186 A1 | 5/2009 | Keller |
| 2009/0157017 A1 | 6/2009 | Ambrosio |
| 2009/0196844 A1 | 8/2009 | Choi et al. |
| 2009/0234306 A1 | 9/2009 | Vitaris |
| 2009/0254053 A1 | 10/2009 | Svensby et al. |
| 2009/0275872 A1 | 11/2009 | Addison et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2010/0012210 A1 | 1/2010 | Miyano et al. |
| 2010/0022972 A1 | 1/2010 | Lina et al. |
| 2010/0030132 A1 | 2/2010 | Niezgoda et al. |
| 2010/0036305 A1 | 2/2010 | Green |
| 2010/0036334 A1 | 2/2010 | Heagle et al. |
| 2010/0069850 A1 | 3/2010 | Fabo |
| 2010/0125258 A1 | 5/2010 | Coulthard et al. |
| 2010/0125259 A1 | 5/2010 | Olson |
| 2010/0135915 A1 | 6/2010 | Greener et al. |
| 2010/0137775 A1 | 6/2010 | Hu et al. |
| 2010/0230467 A1 | 9/2010 | Crisuolo et al. |
| 2010/0259406 A1 | 10/2010 | Caso et al. |
| 2010/0268177 A1 | 10/2010 | Hall |
| 2010/0318052 A1 | 12/2010 | Ha et al. |
| 2011/0004172 A1 | 1/2011 | Eckstein et al. |
| 2011/0021431 A1 | 1/2011 | Jones et al. |
| 2011/0028919 A1 | 2/2011 | Johnnison et al. |
| 2011/0033503 A1 | 2/2011 | Sinko et al. |
| 2011/0036889 A1 | 2/2011 | Heinrich et al. |
| 2011/0066123 A1 | 3/2011 | Tout et al. |
| 2011/0086077 A1 | 4/2011 | McCrea et al. |
| 2011/0118683 A1 | 5/2011 | Weston |
| 2011/0144599 A1 | 6/2011 | Croizat et al. |
| 2011/0147432 A1 | 6/2011 | Heinrich et al. |
| 2011/0147435 A1 | 6/2011 | Heinrich et al. |
| 2011/0224631 A1 | 9/2011 | Simmons |
| 2011/0250447 A1 | 10/2011 | Taniguchi et al. |
| 2011/0257611 A1 | 10/2011 | Locke et al. |
| 2011/0313374 A1 | 12/2011 | Lockwood et al. |
| 2012/0051945 A1 | 3/2012 | Orndorff et al. |
| 2012/0083755 A1 | 4/2012 | Lina et al. |
| 2012/0095380 A1 | 4/2012 | Gergley et al. |
| 2012/0123356 A1 | 5/2012 | Greener |
| 2012/0123358 A1 | 5/2012 | Hall et al. |
| 2012/0222687 A1 | 9/2012 | Czajka, Jr. et al. |
| 2013/0023841 A1 | 1/2013 | Johnson et al. |
| 2013/0066285 A1 | 3/2013 | Locke et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0296762 A1 | 11/2013 | Toth |
| 2013/0302545 A1 | 11/2013 | Schnelker et al. |
| 2013/0310780 A1 | 11/2013 | Phillips |
| 2013/0310781 A1 | 11/2013 | Phillips et al. |
| 2014/0114268 A1 | 4/2014 | Auguste et al. |
| 2014/0171888 A1 | 6/2014 | Croizat et al. |
| 2014/0228791 A1 | 8/2014 | Hartwell |
| 2014/0228792 A1 | 8/2014 | Weston et al. |
| 2014/0316359 A1 | 10/2014 | Collinson et al. |
| 2015/0032035 A1 | 1/2015 | Banwell et al. |
| 2015/0159066 A1 | 6/2015 | Hartwell et al. |
| 2015/0190286 A1 | 7/2015 | Allen et al. |
| 2015/0216733 A1 | 8/2015 | Allen et al. |
| 2015/0306273 A1 | 10/2015 | Karim et al. |
| 2016/0120706 A1 | 5/2016 | Collinson et al. |
| 2016/0144084 A1 | 5/2016 | Collinson et al. |

(56) References Cited

U.S. PATENT DOCUMENTS

| | | | |
|---|---|---|---|
| 2019/0247535 A1 | 8/2019 | Philips | |
| 2020/0139023 A1 | 5/2020 | Haggstrom et al. | |

FOREIGN PATENT DOCUMENTS

| | | |
|---|---|---|
| DE | 34 43 101 | 5/1986 |
| DE | 3 838 587 | 5/1990 |
| DE | 20 2004 017 052 | 7/2005 |
| EP | 0 251 810 | 1/1988 |
| EP | 0 358 302 | 3/1990 |
| EP | 0 425 164 | 5/1991 |
| EP | 0 322 118 | 6/1992 |
| EP | 0 521 434 | 1/1993 |
| EP | 0 325 771 | 9/1993 |
| EP | 0 617 152 | 9/1994 |
| EP | 0 578 999 | 5/1996 |
| EP | 0 549 781 | 9/1996 |
| EP | 0 762 860 | 3/1997 |
| EP | 0 506 241 | 5/1997 |
| EP | 0 793 019 | 9/1997 |
| EP | 0 620 720 | 3/1998 |
| EP | 0 858 810 | 8/1998 |
| EP | 0 651 983 | 9/1998 |
| EP | 0 888 141 | 1/1999 |
| EP | 0 912 251 | 5/1999 |
| EP | 0 923 905 | 6/1999 |
| EP | 1 007 015 | 6/2000 |
| EP | 1 013 290 | 6/2000 |
| EP | 1 029 585 | 8/2000 |
| EP | 1 030 657 | 8/2000 |
| EP | 0 688 189 | 9/2000 |
| EP | 1 088 569 | 4/2001 |
| EP | 1 105 171 | 6/2001 |
| EP | 1 105 180 | 6/2001 |
| EP | 1 107 813 | 6/2001 |
| EP | 1 114 933 | 7/2001 |
| EP | 1 139 951 | 10/2001 |
| EP | 0 921 775 | 12/2001 |
| EP | 1 177 781 | 2/2002 |
| EP | 1 219 311 | 7/2002 |
| EP | 1 306 123 | 2/2003 |
| EP | 1 374 915 | 1/2004 |
| EP | 1 440 737 | 7/2004 |
| EP | 1 018 967 | 8/2004 |
| EP | 1 633 830 | 1/2005 |
| EP | 1 637 088 | 3/2006 |
| EP | 1 798 835 | 6/2007 |
| EP | 1 476 217 | 3/2008 |
| EP | 1 955 887 | 8/2008 |
| EP | 1 978 046 | 10/2008 |
| EP | 1 988 125 | 11/2008 |
| EP | 2 111 804 | 10/2009 |
| EP | 2 127 690 | 12/2009 |
| EP | 2 263 627 | 12/2010 |
| EP | 1 374 914 B1 | 3/2011 |
| EP | 2 335 747 | 6/2011 |
| EP | 2 366 721 | 9/2011 |
| EP | 2 462 908 | 6/2012 |
| EP | 2 529 767 | 12/2012 |
| EP | 2 477 674 | 7/2013 |
| EP | 2 451 498 | 4/2014 |
| EP | 2 544 642 | 1/2015 |
| EP | 2 648 668 | 1/2015 |
| FR | 1 163 907 | 10/1958 |
| GB | 2288734 | 11/1995 |
| GB | 2306580 | 5/1997 |
| GB | 2329127 | 3/1999 |
| GB | 2305610 | 7/1999 |
| GB | 2389794 | 12/2003 |
| GB | 2423019 | 8/2006 |
| GB | 2424582 | 10/2006 |
| GB | 2435419 | 2/2007 |
| GB | 2435422 | 8/2007 |
| JP | S59-36608 | 2/1984 |
| JP | H05-070692 | 3/1993 |
| JP | 2005-261376 | 9/2005 |
| JP | 2005-334188 | 12/2005 |
| JP | 2009-148393 | 7/2009 |
| JP | 2009-542408 | 12/2009 |
| WO | WO 1992/009301 | 6/1992 |
| WO | WO 1992/09651 | 6/1992 |
| WO | WO 1992/10983 | 7/1992 |
| WO | WO 1993/06802 | 4/1993 |
| WO | WO 1993/09176 | 5/1993 |
| WO | WO 1993/09727 | 5/1993 |
| WO | WO 1994/020133 | 9/1994 |
| WO | WO 1994/21207 | 9/1994 |
| WO | WO 1995/04511 | 2/1995 |
| WO | WO 1995/029959 | 11/1995 |
| WO | WO 1996/01731 | 1/1996 |
| WO | WO 1996/05873 | 2/1996 |
| WO | WO 1996/40174 | 12/1996 |
| WO | WO 1997/03717 | 2/1997 |
| WO | WO 1997/11658 | 4/1997 |
| WO | WO 1997/14384 | 4/1997 |
| WO | WO 1997/33922 | 9/1997 |
| WO | WO 1997/38732 | 10/1997 |
| WO | WO 1997/42986 | 11/1997 |
| WO | WO 1997/43991 | 11/1997 |
| WO | WO 1998/06444 | 2/1998 |
| WO | WO 1998/13000 | 4/1998 |
| WO | WO 1999/17698 | 4/1999 |
| WO | WO 1999/19013 | 4/1999 |
| WO | WO 1999/30629 | 6/1999 |
| WO | WO 1999/39671 | 8/1999 |
| WO | WO 1999/047097 | 9/1999 |
| WO | WO 1999/48621 | 9/1999 |
| WO | WO 1999/65536 | 12/1999 |
| WO | WO 2000/00016 | 1/2000 |
| WO | WO 2000/17968 | 3/2000 |
| WO | WO 2000/38752 | 7/2000 |
| WO | WO 2000/40190 | 7/2000 |
| WO | WO 2000/61206 | 10/2000 |
| WO | WO 2000/62827 | 10/2000 |
| WO | WO 2000/064394 | 11/2000 |
| WO | WO 2000/064396 | 11/2000 |
| WO | WO 2000/074738 | 12/2000 |
| WO | WO 2001/10363 | 2/2001 |
| WO | WO 2001/37773 | 5/2001 |
| WO | WO 2001/49233 | 7/2001 |
| WO | WO 2001/062312 | 8/2001 |
| WO | WO 2001/066017 | 9/2001 |
| WO | WO 2001/072251 | 10/2001 |
| WO | WO 2001/87271 | 11/2001 |
| WO | WO 2001/89588 | 11/2001 |
| WO | WO 2002/02079 | 1/2002 |
| WO | WO 2002/05737 | 1/2002 |
| WO | WO 2002/17840 | 3/2002 |
| WO | WO 2002/24132 | 3/2002 |
| WO | WO 2002/38096 | 5/2002 |
| WO | WO 2002/070040 | 9/2002 |
| WO | WO 2002/094256 | 11/2002 |
| WO | WO 2002/102864 | 12/2002 |
| WO | WO 2003/005943 | 1/2003 |
| WO | WO 2003/022333 | 3/2003 |
| WO | WO 2003/041786 | 5/2003 |
| WO | WO 2003/065877 | 8/2003 |
| WO | WO 2003/072748 | 9/2003 |
| WO | WO 2004/016313 | 2/2004 |
| WO | WO 2004/037334 | 5/2004 |
| WO | WO 2004/052982 | 6/2004 |
| WO | WO 2004/054632 | 7/2004 |
| WO | WO 2004/060148 | 7/2004 |
| WO | WO 2004/077387 | 9/2004 |
| WO | WO 2004/098474 | 11/2004 |
| WO | WO 2004/108175 | 12/2004 |
| WO | WO 2005/009488 | 2/2005 |
| WO | WO 2005/017000 | 2/2005 |
| WO | WO 2005/018695 | 3/2005 |
| WO | WO 2005/019343 | 3/2005 |
| WO | WO 2005/025447 | 3/2005 |
| WO | WO 2005/046760 | 5/2005 |
| WO | WO 2005/082435 | 9/2005 |
| WO | WO 2005/118011 | 12/2005 |

(56) References Cited

FOREIGN PATENT DOCUMENTS

| | | |
|---|---|---|
| WO | WO 2005/123170 | 12/2005 |
| WO | WO 2006/005939 | 1/2006 |
| WO | WO 2006/014534 | 2/2006 |
| WO | WO 2006/028244 | 3/2006 |
| WO | WO 2006/030054 | 3/2006 |
| WO | WO 2006/034128 | 3/2006 |
| WO | WO 2006/034166 | 3/2006 |
| WO | WO 2006/046060 | 5/2006 |
| WO | WO 2006/052839 | 5/2006 |
| WO | WO 2006/081403 | 8/2006 |
| WO | WO 2006/114637 | 11/2006 |
| WO | WO 2006/116992 | 11/2006 |
| WO | WO 2006/135506 | 12/2006 |
| WO | WO 2006/135934 | 12/2006 |
| WO | WO 2007/031757 | 3/2007 |
| WO | WO 2007/031762 | 3/2007 |
| WO | WO 2007/092397 | 8/2007 |
| WO | WO 2007/095180 | 8/2007 |
| WO | WO 2007/106590 | 9/2007 |
| WO | WO 2007/106594 | 9/2007 |
| WO | WO 2007/116347 | 10/2007 |
| WO | WO 2007/123451 | 11/2007 |
| WO | WO 2007/124198 | 11/2007 |
| WO | WO 2007/133618 | 11/2007 |
| WO | WO 2007/143060 | 12/2007 |
| WO | WO 2008/008032 | 1/2008 |
| WO | WO 2008/028494 | 3/2008 |
| WO | WO 2008/036162 | 3/2008 |
| WO | WO 2008/039223 | 4/2008 |
| WO | WO 2008/040681 | 4/2008 |
| WO | WO 2008/043067 | 4/2008 |
| WO | WO 2008/060475 | 5/2008 |
| WO | WO 2008/076407 | 6/2008 |
| WO | WO 2008/082444 | 7/2008 |
| WO | WO 2008/086397 | 7/2008 |
| WO | WO 2008/100437 | 8/2008 |
| WO | WO 2008/104609 | 9/2008 |
| WO | WO 2008/134544 | 11/2008 |
| WO | WO 2008/134774 | 11/2008 |
| WO | WO 2008/135997 | 11/2008 |
| WO | WO 2009/011856 | 1/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/077722 | 6/2009 |
| WO | WO 2009/086580 | 7/2009 |
| WO | WO 2009/088925 | 7/2009 |
| WO | WO 2009/090074 | 7/2009 |
| WO | WO 2009/102021 | 8/2009 |
| WO | WO 2009/103031 | 8/2009 |
| WO | WO 2009/122989 | 10/2009 |
| WO | WO 2009/124100 | 10/2009 |
| WO | WO 2009/124407 | 10/2009 |
| WO | WO 2009/126102 | 10/2009 |
| WO | WO 2009/146441 | 12/2009 |
| WO | WO 2009/156709 | 12/2009 |
| WO | WO 2009/158128 | 12/2009 |
| WO | WO 2010/006182 | 1/2010 |
| WO | WO 2010/19997 | 1/2010 |
| WO | WO 2010/121033 | 10/2010 |
| WO | WO 2010/122665 | 10/2010 |
| WO | WO 2010/142959 | 12/2010 |
| WO | WO 2010/147533 | 12/2010 |
| WO | WO 2011/072840 | 6/2011 |
| WO | WO 2011/112870 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO-2011135284 A1 | 11/2011 |
| WO | WO 2012/009370 | 1/2012 |
| WO | WO-2012021553 A1 | 2/2012 |
| WO | WO 2012/041296 | 4/2012 |
| WO | WO 2012/069793 | 5/2012 |
| WO | WO 2012/069794 | 5/2012 |
| WO | WO 2012/074512 | 6/2012 |
| WO | WO 2012/078707 | 6/2012 |
| WO | WO 2012/131237 | 10/2012 |
| WO | WO 2012/140378 | 10/2012 |
| WO | WO 2012/143665 | 10/2012 |
| WO | WO 2013/010907 | 1/2013 |
| WO | WO 2013/029652 | 3/2013 |
| WO | WO 2013/033131 | 3/2013 |
| WO | WO 2013/064852 | 5/2013 |
| WO | WO 2013/076450 | 5/2013 |
| WO | WO 2013/083800 | 6/2013 |
| WO | WO 2013/090810 | 6/2013 |
| WO | WO 2013/110008 | 7/2013 |
| WO | WO 2013/136181 | 9/2013 |
| WO | WO 2013/149078 | 10/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |

OTHER PUBLICATIONS

International Preliminary Report on Patentability, re PCT Application No. PCT/GB2012/000866, dated Jun. 5, 2014.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
International Search Report and Written Opinion, re PCT Application No. PCT/GB2012/000866, dated Feb. 28, 2013.
Jahns et al., Poster "Problemwundversorgung mit einem neuen anschmiegsamen Silikonschaumverband mit Anwendung der Vakuumtechnik," 2nd Congress of German Wound Treatment Society 1998.
Kendall ULTEC Hydrocolloid Dressing (4"x4"), product ordering page, web page downloaded Jul. 13, 2014.
Khan, et al., "Influence of Chitosan Molecular Weight on its Physical Properties", EIMJM (2003); 2(1); pp. 1-8.
Product Data Sheet, WACKER SilGel 612 A/B. Jun. 2014.
Protz, Kerstin: "Modern Wundauflagen unterstutzen Heilungsprozess", Wundversorgung: Indikation und Anwendung, Geriatrie Journal, Apr. 2005, pp. 3333-3339, with translation.
Sogias, et al., "Exploring the Factors Affecting the Solubility of Chitosan in Water", Macromol. Chem. Phys. (2010); 211; pp. 426-433.
Wacker SILPURAN 2445 data sheet, dated Oct. 11, 2014.
Wooding-Scott, Margaret, et al., "No Wound is Too Big for Resourceful Nurses," RN Dec. 1988, pp. 22-25 USA.
X-ray Sterilisation dated Mar. 1, 2008. Retrieved from http://www.emdt.co.uk/article/x-ray-sterilisation.
X-ray Sterilisation. The Technology of the Future dated Feb. 1, 2010. Retrieved from http://www.emdt.co.uk/article/x-ray-sterilisation-technology-future.

* cited by examiner

COMPOSITION, APPARATUS, KIT AND METHOD AND USES THEREOF

CROSS-REFERENCE TO RELATED APPLICATIONS

This application is continuation of U.S. application Ser. No. 14/360,591, having a 371(c) date of Nov. 4, 2014, which is a U.S. National Phase of the PCT International Application No. PCT/GB2012/000866, filed on Nov. 26, 2012, which claims priority to UK Application Nos. 1120454.2 and 1209619.4, filed on Nov. 25, 2011 and May 30, 2012, respectively.

Embodiments relate to a composition, an apparatus, a kit, methods using the same and uses thereof in the field of wound care, particularly in advanced wound management, more particularly in the application of topical negative pressure (TNP) therapy to a wound site. In particular, but not exclusively, certain embodiments relate to the management of negative pressure loss from a wound dressing intended for covering a wound site whilst TNP therapy is applied.

BACKGROUND

Many different types of wound dressing are known for aiding in the healing process of a human or animal subject in need thereof. These different types of wound dressing include many different types of materials and layers, for example, gauze, pads and/or foam pads with overlying drapes or multi-layer wound dressings. Advanced wound management dressings are known for the management or healing of complex wounds. Advanced wound management dressings are dressings which are tailored to include specific provision for management of wound exudates (ALLEVYN, DURAFIBER, Gentle Border), infection management (ACTICOAT, IODOSORB), iv site care (IV3000), management of compromised skin about the wound, and the like, NPWT (RENASYS F/AB, PICO), post operative such as surgical drapes (OPSITE), temporary bioskin dressings (BIOBRANE). Advanced wound management dressings include for example Gentle Border® dressings and complex multi-layer TNP therapy dressings, amongst others.

TNP therapy sometimes referred as vacuum assisted closure VAC™ or negative pressure wound therapy (NPWT) has recently been proposed as a successful mechanism for improving the healing rate of a wound. Such therapy using sub-atmospheric pressure is applicable to a broad range of wounds such as chronic wounds, incisional wounds, open wounds and abdominal wounds or the like.

During TNP therapy, a suction source such as a vacuum pump or the like is utilised to create a negative pressure region. That is to say, a region where an experienced pressure is below that of the surroundings. The suction source creates a negative pressure via a dressing or drape positioned over and sealed about or around the periphery of the wound. Wound exudate and other potentially harmful material is enclosed under the dressing or drape and extracted therefrom. Throughout the specification, the terms wound cover, wound dressing and dressing are hereinafter used interchangeably unless otherwise indicated or intimated, and the term drape is intended to refer to such wound cover, wound dressing or dressing, unless otherwise indicated. Throughout the specification, the terms sealant and composition are hereinafter used interchangeably unless otherwise indicated or intimated.

Many known techniques provide an inefficient seal enclosing the wound. An inefficient seal results in loss of negative pressure. Creating an efficient seal is particularly challenging in the case of wounds which are subject to friction or shear when the subject or wearer is moving, or in the case of wounds on complex body topography or complex body geography, such as heels and the like, which are poorly accessible or problematic to dress effectively, for example wounds on concave or convex surfaces and the like.

Loss of negative pressure can reduce the effectiveness of the applied therapy, i.e. the apparatus operates at sub-optimal levels of negative pressure or moves to an alarm state. This can prolong the period for which therapy must be continued, and can reduce or limit the overall recovery of the wound.

Moreover in the case of mobile and disposable TNP therapy apparatus, where the vacuum source relies on a finite energy source (for example a mechanically powered system such as spring driven mechanism, (SNaP® Spiracur), or a chemically powered system such as battery operated PICO™ having a finite battery life), therapy must be discontinued while the battery is replaced or recharged. An inefficient seal places heavier demand on the battery and demands increase in capacity of pump, which goes counter to the goal of mobile and disposable apparatus. Many TNP systems include a negative pressure sensor and an automatic shut-down initiated by detection of a loss in negative pressure. The subject is instructed to secure the source of negative pressure loss if possible or have the dressing reapplied before the therapy can continue.

One approach to improving the effectiveness of a seal between skin adjacent or surrounding a wound site and a dressing or drape is to use a dressing or drape of which the wound contacting surface comprises a strongly adhering adhesive, which adheres to the skin (e.g stratum corneum or the like). Such adhesives include for example acrylic pressure sensitive adhesive (PSA) provided as a coating on a polyurethane dressing or drape. However these adhesives are prone to adhere so well to the skin that adjusting or repositioning of the dressing or drape, or removal of the dressing or drape, can cause distress to the subject or cause damage to weak or friable skin. PICO™ (Smith & Nephew) comprising a mildly adhering combination dressing incorporating drape, functional wound therapy layers and an integral attachment for a negative pressure source, together with a number of acrylic PSA coated polyurethane adhesive "retention" strips presents a significant improvement. The mildly adhering dressing is applied and may be repositioned without distress to the subject, and once satisfactorily positioned is secured in place by the adhesive strips applied around its outer edges, overlaying the edge of the dressing and the surrounding skin. PICO™ works admirably on simple wound locations but is less well suited to more complex surfaces, at which it may be difficult to apply the strips smoothly.

A further approach is adopted with Kalypto's NPWT dressing which incorporates a hydrocolloid gasket applied to the drape portion of the dressing.

The inherent texture of a skin surface, healthy or damaged, presents barely visible channels or microchannels when covered over by a sheet material such as a dressing, which render the seal between skin and dressing air permeable, with resulting loss of negative pressure. Such microchannels can best be sealed by introducing a fluid sealant and allowing this to gel or solidify in position and thereby flexibly plug the microchannels. The silicone based two-part adhesive sealant Mepiseal™ may be combined in one part and applied to healthy skin whereafter a dressing is adhered thereover, thereby containing harmful wound exudates within the bounds of the sealant. In recent usage, Mepiseal™ has found application as a TNP sealant applied about a wound dressed or filled with wound filler, an acrylic drape positioned over and about the wound, filler and sealant and adhered strongly to the skin and sealant around or about the wound by means of an acrylic PSA adhesive at its surface. The drape thus overlies and forms a seal with the pre-positioned Mepiseal™ which cures to form a flexible polymer. The sealant adheres preferentially to the acrylic drape and this minimises any distress caused to the subject during removal of or changing a dressing, over the distress of removing the dressing itself.

Whilst Mepiseal™ works effectively with an acrylic coated polyurethane drape, the strongly adhering drape is prone to causing distress to subjects. The seal is so effective that Mepiseal™ could in theory be used with less well adhering, and more skin-friendly, drapes such as silicone based drapes, which are known to have excellent properties as skin contact layers. However we have found that Mepiseal™ is incompatible with TNP dressings and drapes incorporating a silicone based skin contact layer, such as PICO™. There are two separate issues involved. Firstly we have found that the silicone based Mepiseal™ elastomer applied to skin and subsequently covered over with a PICO™ dressing in novel manner resulted in unstable border adhesion of the dressing, noticeably disrupted by low-level movement of the subject wearing the dressing, resulting in dressing lift at the edges, although it did remove cleanly with the dressing. Secondly, Mepiseal™ applied in novel manner after positioning the PICO dressing, at the interface of PICO and skin, adhered equally to both skin and to such dressings or drapes, but with failure of the Mepiseal™ seal bridging the two. This appears to be caused by cohesive failure of the Mepiseal™, resulting in remnants remaining adhered to both skin and dressing.

SUMMARY

It is an aim of certain embodiments to at least mitigate the above-mentioned problems.

It is an aim of certain embodiments to provide a dispensable skin-compatible composition which may be dispensed to the skin about a wound as an effective sealant for adhering or locating a wound dressing incorporating a skin-compatible skin contact surface. Preferably a composition is provided which may be dispensed as a sealant for a dressing and for irregular skin topography such as crevices or depressions, preferably an advanced wound management dressing, more preferably a negative pressure dressing, more preferably a combination TNP therapy dressing, which is able to contain a negative pressure at a wound site.

It is an aim of certain embodiments to provide a wound dressing kit including a dressing, preferably an advanced wound management dressing, more preferably a negative pressure dressing, more preferably a combination TNP therapy dressing, comprising a skin-compatible skin contact layer or surface, together with a skin-compatible sealant, adapted to be applied in conjunction at a wound site in fluid-tight manner that is to say, the wound cover, dressing or drape may be adapted to be applied in conjunction with a sealant at a wound site in a negative pressure efficient manner, such as in manner to contain a negative pressure, and able to be used with TNP therapy.

It is an aim of certain embodiments to provide an apparatus in the form of a wound dressing or cover, preferably an advanced wound management dressing, comprising a silicone based skin contact layer or surface for use in conjunction with a skin-compatible sealant, which is adapted to be applied in fluid-tight manner at a wound site. Preferably the wound cover is adapted to be applied in negative pressure efficient manner, such as in manner to contain a negative pressure at a wound site.

It is an aim of certain embodiments to provide a method of treating a wound with TNP therapy transmitted through a wound dressing or drape, preferably an advanced wound management dressing, comprising a silicone based skin contact surface in conjunction with a skin-compatible sealant, which is applied in a negative pressure efficient manner, that is to say in manner to contain a negative pressure at a wound site.

It is further an aim of certain embodiments to manage the transmission of negative pressure to a wound by means of a wound dressing or drape, preferably an advanced wound management dressing, comprising a silicone based skin contact layer in conjunction with a skin-compatible sealant, which is negative pressure efficient, such as in manner to contain a negative pressure at a wound site.

It is further an aim of certain embodiments to provide an elastomeric seal between skin about a wound and a wound dressing, which seals microchannel and macrochannel, i.e. skin textural features and body topographical features. The former is essential to a seal whilst the latter plugs potential gaps or leaks by planarising an irregular body geometry surface to be fit to receive a dressing.

According to a first embodiment there is provided a curable composition for use in wound care, comprising, apportioned between at least one Part A and at least one Part B:

one or more alkenyl-group containing polymers (i) having at least one alkenyl group or moiety per molecule, one or more SiH-containing polymers (ii) having at least one Si—H unit per molecule; and a catalyst (iii) for curing by addition of alkenyl-containing polymer (i) to SiH-containing polymer (ii), Part A and Part B independently having viscosity at 23° C. in the range up to 300 Pa·s, preferably in the range 10-100 Pa·s, at a shearing rate of $10 \text{ s}^{-1}$, and when combined in one Part, having cure time at 23° C. in the range from 0.5 min to 25 min, wherein when dispensed into a location about a wound dressing, said wound dressing overlying a wound site and skin thereabout, said dispensing being so as to intimately contact and overlie an edge of said dressing and skin about said edge, the composition cures in contact with said edge and skin at 32° C. to an elastomer exhibiting zero or low tack at a time in the range from 0.5 to less than 30 minutes.

A "unit" as herein referred is a group or moiety or part thereof. A "moiety" as herein referred is a group of atoms having further atoms disposed on two or more sides thereabout, ie having two or more valencies unspecified. A "group" as herein referred is a group of atoms having further atoms disposed on one side thereof, ie having one valency unspecified. Si—H units herein have the same meaning as SiH units Polymers (i) and (ii) as hereinbefore defined are fluid-phase polymers incorporating reactive groups which crosslink in presence of catalyst to form a copolymer more preferably a cured elastomer. Suitably Part A comprises catalyst together with polymer (i), and Part B comprises polymer (ii) optionally together with any remaining polymer (i). Suitably polymers, catalyst and optional further components are apportioned in manner to balance volumes and viscosities of both Parts. Preferably polymer (i) is an alkenylsiloxane-containing polymer.

An edge of said dressing may be more precisely referred to as a perimeter of said dressing, whereby said perimeter overlies skin about said wound site and said composition is dispensed to intimately contact and overlie said perimeter and skin adjacent thereto and/or thereabout.

Throughout the specification, reference to tack in the range of less than or equal to low tack is to zero-tack or low tack.

Cure time and low tack time are given as the time where t=0 is the time of combining and/or dispensing said Parts. Preferably in practice these actions are substantially simultaneous.

Preferably the Parts are combined and intimately admixed prior to or during to dispensing.

Preferably the composition cures in contact with said perimeter and skin to form an elastomeric seal therebetween.

Preferably the composition is dispensed to simultaneously contact dressing and skin. Such preference should however allow for human error in alignment to both surfaces simultaneously. Alternatively or additionally composition is dispensed and subsequently smoothed to contact both dressing and skin.

A number of methods are known in the art to monitor the cure of liquid polymers and in particular RTV-2 silicones, these vary from continuous monitoring across the full cure profile of the material with instruments such as scanning vibrating needle curemeters (B. G. Willoughby and K. W. Scott, *Understanding cure with the scanning vibrating needle curemeter* (scanning VNC), RTL2844, Rapra Technology Limited, Shawbury) or differential scanning calorimeters (L. M. Lopez, A. B. Cosgrove, J. P. Hernandez-Ortiz, T. A. Osswald, *Modeling the Vulcanization Reaction of Silicone Rubber*, Polym. Eng. Sci., 2007, 47, 675-683) through to empirical single point determinations typically based on clear physical changes, for example recording the time taken to reach the gel point.

During the trials described in the examples it was found that transfer of uncured sealant from the application site to other surfaces was a clear disadvantage. For the purpose of defining an unambiguous single point on the cure profile, cure time is taken to mean manual kinetic cure time. Manual kinetic cure time is herein defined as the cure time (at a specified temperature) at which material is no longer transferred to skin (i.e. a fingertip) when subject to a light, brief touch.

Due to the temperature dependence of the cure profile on addition cure RTV silicones it is important that comparison between any measurements is carried out at the same temperature and that the temperature be reported. Guidance set out in *Methods of Test for Surgical Dressings in the British Pharmacopoeia* (BP), 1993, 14$^{th}$ edition, A222, Appendix XX is that the temperature of a *regulated atmosphere* is taken as 20° C.±2° C. Within the silicone industry there are many instances where curing parameters of addition cure RTV-2 silicones are reported at a nominal temperature of 23° C., this falls in line with standard test methods for other temperature dependant properties such as viscosity (when measuring viscosity DIN EN ISO 3219: 1994 describes a preferred measurement temperature of 23.0° C.±0.2° C.), examples of this include: *Pot Life* reported by Wacker Silicones (at 23° C. on Technical data sheet for Silpuran® 2445 A/B, Version 1.3 & Technical data sheet for Silpuran® 2450 A/B, Version 1.3, Wacker Chemie A G, München); *Maximum Working Time* reported by Bluestar Silicones (at 23° C. on The Silbione® Difference, Silicones for Healthcare Applications, Bluestar Silicones France SAS, Lyon) and *Pot Life* reported by Momentive (defined as the time for initial viscosity to double at 23° C. on Silicone Gels for Healthcare Applications, 152-053-00E-GL, Momentive Performance Materials Inc., Columbus). When considering the temperature of a material applied to skin, it should be noted that the temperature of skin is nominally taken as 32° C. In a clinical environment, when a curing RTV-2 silicone is applied as a thin bead, layer or film in intimate contact with the skin, it has been assumed that the material will reach thermal equilibrium with the skin rapidly.

Within the literature other discrete points along the cure profile are routinely used, of note are: pot life, this usually indicates the maximum period of time after which the mixed silicones may still be worked, poured, spread etc. Where flow is an important requirement pot life is usually quoted as the time required for the initial viscosity to double (*Elastosil, Processing RTV-2 silicone rubbers*, 6020e/06.06, Wacker Chemie A G, München) and tack free time, this is an appropriate measure when considering a rubber (by definition the material must not have any discernible tack or grab once cured) and may be assessed in a similar way to manual kinetic.

Preferably the composition has cure time as hereinbefore defined at 23° C. in the range from 0.5 min to 20 min, more preferably from 0.5 to 18 min, more preferably from 0.5 to 16 min, most preferably 12 min, most preferably 0.5 to 5 min. Cure time is manual kinetic as hereinbefore defined.

Values at 32° C. are particularly instructive in the present application, preferably cure time at 32° C. is in the range 0.5 to 10 minutes, more preferably 0.5 to 8 minutes, most preferably in the range 0.5 to 7 minutes.

Tack is hereinbelow measured as maximum force required to separate a probe from cured composition. However for the purpose of determining tack-free or low tack time, a touch and lift test was performed at intervals with the finger, on controlled samples, and tack free or low tack time determined as the time at which the sample did not adhere to and lift with touch.

Preferably tack-free time is in the range from 0.5 to 25 minutes, more preferably from 0.5 to 22 minutes. Preferably the composition has tack as herein before defined at a period in the range from 0.5 minutes to 22 minutes after combining such as to not adhere items such as paper or clothing which contact the composition. Finger tack is a relatively subjective evaluation which can be obtained by touching the surface of the dispensed composition to determine the "stickyness" thereof. Descriptive terms such as high H), low (L) and moderate (M) can then be attributed as a preliminary measure.

Preferably the composition after curing as a sample with a height of 1 mm has extensibility such that the load required to produce a 20% extension at a rate of extension of 300 mm per minute is in the range of less than or equal to 1.4 kgf per cm width (kgfcm$^{-1}$), preferably in the range 0.001 to 1.4 kgf cm$^{-1}$ expressed preferably as 0.001 to 14.0 kgf cm$^{-2}$ to produce 20% extension, more preferably in the range 0.001 to 5.0 kgf cm$^{-2}$.

It will be clear that viscosity for each of Parts A and B is for the as-provided components, prior to mixing.

Suitably the components mix to a dispensible viscosity.

Preferably the cured composition has elongation at break as hereinbelow defined, greater than or equal to 50%.

Preferably the cured composition has tensile strength, as hereinbelow defined, greater than or equal to 5 kgfcm$^{-2}$.

Preferably for the cured composition permanent set is in the range 20% to 0%.

Preferably the composition is Silpuran 2445™, optionally incorporating viscosity and/or cure time modifier providing increased viscosity and reduced cure time. Preferably the composition has translucent appearance after curing.

Preferably the composition is dispensed to overly the edge of a TNP dressing overlying a wound site and skin thereabout, preferably as a sealant bridging the dressing and skin thereabout.

Preferably the composition is dispensed into a location as hereinbefore defined wherein the dressing comprises a skin and/or wound contact surface for overlying a wound and skin thereabout, wherein the contact surface is skin compatible, preferably is a silicone surface.

Preferably dispensing is in the form of a discrete or continuous bead or film bridging an interface between the dressing and skin about the dressing, and optionally additionally bridging an interface between overlapping dressings and optionally additionally bridging a topographical recess feature of skin about and/or underlying and/or adjacent the dressing.

Preferably the composition is dispensed for sealing a dressing suitable for applying to a wound selected from readily accessible and difficult to access wounds, exposed and concealed wounds, large and small wounds, regular and irregular shaped wounds, planar and topographically irregular, uneven or complex wounds, more preferably on a site selected from the heel, sacrum, axial, inguinal, shoulder, neck, foot, digit, knee, elbow, hand or for sealing a crevice adjacent or adjoining a wound site, selected from such as sacral cleft, fossar and the like.

Preferably the composition is dispensed as a sealant for a Negative Pressure Wound Therapy (NPWT) wound dressing, preferably a combination TNP dressing incorporating drape, functional wound therapy layers and an integral attachment for a negative pressure source, preferably a portable and/or periodic negative pressure source.

The composition as hereinbefore defined may be other than and distinct from a composition as described in WO2004/108175 or may represent a selection therefrom; preferably it is not a 2 or more part addition curing RTV silicone preparation which has tack other than hereinbefore defined whereby it is limited to being applied to the skin around a wound, immediately outside the edge of a wound, and to the upper side of which, being that side which faces away from the skin, an article for medical use may be applied and adhered after which the preparation is allowed to cure to form an elastomer which adheres to the skin with the article being affixed to the preparation after the latter has cured, with the primary purpose of protecting the skin around the wound, particularly against the leakage of wound liquid from the wound to the skin outside the wound at the same time as it protects against passage of liquids, for example urine, from the outside to inside the wound; more preferably it is not Mepiseal™.

It will be clear that compositions of WO2004/108175 are not primarily suitable for forming an exposed seal, overlying and about an edge of a wound dressing and the greater demands of affixing such wound dressing, particularly an advanced wound management dressing, more particularly a TNP wound dressing, most particularly a combination TNP wound dressing, with the primary purpose of adhering and sealing a dressing having a mildly adhering adhesive and/or with the primary purpose of sealing a dressing for containing a negative pressure; moreover is not suitable for sealing the edge of a mildly adhered wound dressing to skin about the edge of such dressing, moreover is not suited for the purpose of filling skin irregularities or crevices or complex body topography or complex body geography to provide a planar surface for dressing adhesion.

Preferably a composition is a sealant for sealing a wound cover comprising a skin-compatible skin and/or wound contact surface, in place at or about a wound site, being a dispensible skin-compatible composition which comprises skin wetting properties whereby it provides a seal at an interface between skin and a wound cover when dispensed in contact with skin and a wound cover and which cures to an extensible elastomer, i.e. having extensibility comparable to that of healthy skin. In a further advantage the sealant adheres to the wound dressing in preference to skin, or has a cohesion greater than or corresponding to its adhesion to skin.

The composition provides the advantages of enabling sealing a wound dressing after positioning the dressing, thereby enabling more accurately dispensing composition into the intended location to seal the dressing in general or to specifically seal leaks if appropriate. In the case of TNP wound dressing, the composition enables a NP to be established before sealing. The composition forms an exposed seal which is minimally disturbed by external influences after curing, thereby forming an optimally fluid-tight seal. The composition provides admirable adhesion to both dressing, including "hard-to adhere" dressings having a silicone wound-contact surface, and skin, including skin at wound sites such as irregular skin topography sites. The composition provides excellent mechanical properties which enable the seal to withstand body movement and remain intact for periods of 1, 2, 3, 4, 5, 6 or 7 days up to 10 days, without debonding or suffering cohesive failure. Moreover the composition provides excellent extensibility minimising traction damage to skin.

Further embodiments provide a kit, apparatus, use and methods for use in the field of wound care, including a method for treating a wound site.

Embodiments provide a composition for dispensing, or when dispensed, to form a seal about a wound covered with a skin compatible fluid-tight cover. Reference herein to fluid includes liquid and gas. However it is not intended that "fluid" should encompass "vapour", a favourable moisture vapour transmission rate (MVTR) being a requirement of dressings envisaged herein. The wound cover is impermeable or substantially impermeable to fluids including wound exudate. The cover is air-tight or substantially air-tight, whereby a negative pressure may be maintained at a wound site to which the dressing is applied and sealed thereabout with the composition. Wound exudates and other fluids may be contained within the wound site and/or apparatus and any collection means associated therewith.

Certain embodiments provide a method which facilitates applying TNP to a wound site whereby power consumption at a source such as a vacuum pump generating negative pressure is efficient and negative pressure, and thereby therapy, can be continued for as long as desired.

Certain embodiments facilitate applying TNP to a wound site whereby negative pressure is effectively applied at a wound site and therapy can facilitate in wound healing as desired.

Certain embodiments facilitate applying to a wound site a TNP dressing which is substantially undisturbed by external influences.

Certain embodiments facilitate accurately positioning or repositioning a dressing at a wound site as desired without causing significant distress to a patient or subject wearing the dressing.

Certain embodiments facilitate removing a dressing from a wound site without causing undue distress to a patient or subject wearing the dressing.

Certain embodiments provide the advantage that a wound dressing can be effectively applied to a wound site without undue distress to a patient or subject. A pump may be connected to the wound dressing and maintain at the wound site a negative pressure generated during a TNP therapy process and operated for an intended lifetime without inefficient power use by the pump caused by loss of negative pressure.

BRIEF DESCRIPTION OF THE DRAWINGS

Embodiments will now be described hereinafter, by way of non-limiting example only, with reference to the accompanying drawings in which:

FIGS. 3a to 3c illustrate the application and sealing of an embodiment of a wound cover kit, apparatus and sealant onto a subject.

In the drawings like reference numerals refer to like parts. Drawings are not to scale.

DETAILED DESCRIPTION

Figure 1A:
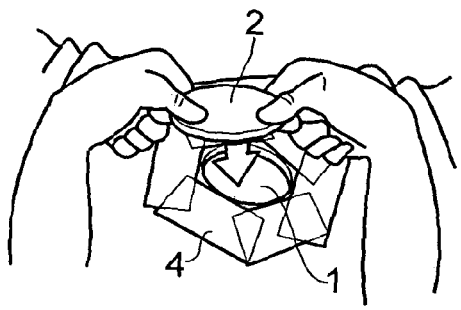
FIGS. 1a to 1g illustrate the conventional application and sealing of a TNP dressing.

The composition of certain embodiments are characterised by a viscosity as hereinbefore defined. Viscosity ($\eta$) was measured in accordance with DIN EN ISO 3219:1994, Annex B. Preferably viscosity is in the range 10-100 Pa·s.

The composition may be dispensed to skin about or adjacent any wound site, which may be upward or downward facing and remain in position, without significantly running, dropping off, dripping etc. until it has taken on elastomer form, moreover on dispensing it wets the skin such that it flows into any irregularities or crevices. The composition will consequently come into close mechanically adhesive or dispersively adhesive contact with skin around the region of the wound and thereby form a seal. In similar manner the composition will come into close mechanically adhesive or dispersively adhesive contact with a dressing and thereby form a seal.

The composition may be combined and allowed to partially cure to a suitable viscosity for application, or may have thixotropic properties such that a suitable viscosity is achieved when subject to shear forces during application.

The composition may have flow properties such that it can be drawn into defects by the prevailing negative pressure and then cure. The cured sealant preferably retains a degree of flow or conformability, for example extensibility, such that it can accommodate the dynamic conditions encountered when on the skin.

Preferably a composition, kit, apparatus, use or method as hereinabove or hereinafter described or claimed, comprises or provides any of the following properties: skin-wetting properties, dispensability, skin-compatibility, adherence to skin, extensibility, conformability, mechanical anchoring, fluid-tightness, efficiency of seal, surface tack, moisture vapour permeability (MVP), preferential adhesion or cohesion and other properties as hereinbelow defined.

Reference herein to a "dispensable" composition is to a composition which has viscosity in the range as hereinbefore or hereinbelow defined. Such composition may be dispensed in position and remain in position after dispensing High viscosity compositions are physically difficult to dispense, and low viscosity compositions have a tendency not to remain in position, when subject to gravity or abrasion by clothing etc. Medium viscosity compositions include. "non-sag spreadable" compositions, known in the art, which differ from spreadable grades in their reduced flowability: up to a dispensing thickness of 10 mm they neither run off under gravity from a vertical or inclined surface nor sag. High viscosity compositions may be dispensed as known in the art by means of smaller volumes, with use of suitably large cross section dispensing heads or apertures, or with use of mechanically advantageous dispensing means. Preferably medium viscosity compositions are non-sag spreadable as hereinbefore defined.

Skin compatible as used herein refers to the ability to apply or reapply a wound cover to skin and remove a wound cover from skin without trauma to the wearer, and without causing substantial damage to the skin. Skin compatible materials include adhesive or non-adhesive materials such as acrylic PSA, silicone and silicone based materials and other materials as hereinbelow recited. A particularly well known skin compatible material comprises silicone or is silicone based, and skin compatible materials are envisaged having properties corresponding to silicone or silicone based material. Unfortunately currently available silicone based sealants disrupt functionality of dressings incorporating silicone wound contact layers when applied under the dressings. Embodiments provide ways to address providing a preferentially adhering seal between silicone based sealants and drapes. Sealant and/or dressing may exhibit adherence to skin after curing on skin of 0.3-3.0N/25 mm. Suitably sealant or a skin and/or wound compatible dressing surface has a skin damage index on removal from skin, Hx, which is less than or equal to that of an acrylic dressing. Hx may be less than 0.1, preferably less than 0.5. Preferably adhesion enables removal without stripping of skin.

Embodiments of the cured composition, kit, and apparatus and methods are negative pressure efficient. Reference herein to negative pressure efficient is to such composition, kit or apparatus or method for transmitting negative pressure to a wound without loss or substantial loss of negative pressure, or which facilitates negative pressure loss—free TNP or substantially negative pressure loss—free TNP or which contains negative pressure at a wound. Such property is also referred herein as being fluid-tight, or substantially fluid-tight. Reference to fluid is to liquid or air as hereinbefore defined. It will however be appreciated that dressings described in this application may permit transpiration, and therefore fluid loss may take place from the dressing. In particular a composition, kit or apparatus may be applied to a patient or subject and provide an interface between the patients or subjects skin and the apparatus, in manner to maintain or contain negative pressure at the wound. Measuring loss of negative pressure at specific points of a dressing is not realistic, and reference is made to the overall Negative Pressure efficiency of dressing and seal together, and can be expressed as leak rate of air into the dressing, more particularly into the NP chamber of a dressing.

Commercially available negative pressure systems give a specification of negative pressure loss tolerance. The RENASYS*EZ™ system has a tolerance of 2 1 min$^{-1}$, RENASYS*EZ Plus™ of 2.5 1 min$^{-1}$, and currently under development portable systems, which have finite power life, for example finite battery life, have specifications of 5-10 ml min$^{-1}$. Generally the leak rate is related to the scale of the system pump and/or nature of power source. Preferably a negative-pressure efficient seal for a portable NPWT system as herein refers to a leak rate of less than or equal to 20 ml min$^{-1}$, more preferably less than or equal to 15 ml min$^{-1}$, more preferably less than or equal to 5 ml min$^{-1}$. An exemplary seal gives a leak rate of less than 3 ml min$^{-1}$, or less than 2 ml min$^{-1}$ or less than 1 ml min$^{-1}$, for example less than or equal to 0.5 ml min$^{-1}$.

Negative pressure leak rate is essentially the diminishing of negative pressure, as air seeps into a region of negative pressure. A measure of negative pressure efficiency is indicated as the ability of a dressing sealed by the composition as herein described, or a sealed dressing as herein described to contain a negative pressure applied by means of a negative pressure source such as a vacuum pump or mechanical resilient force or spring. Aspects and embodiments as herein defined when employed to dress a wound exhibit a negative pressure leak rate (flow of air per unit time) in the range up to 20 ml min$^{-1}$. Negative pressure leak rate is to some extent dependent on dressing type, dressing size and wound size, multiples of dressings applied to cover a wound, body geometry, condition of the subject's skin etc and a useful parameter is therefore % reduction in leak rate at a given dressed wound, which is preferably in the range of greater than or equal to 20% reduction in leak rate, i.e. 20% up to 100% reduction in leak rate. % Reduction in leak rate is herein defined as 100−(final leak rate/initial leak rate×100). So for example for a wound with a 100 ml/min leak rate reduced to 1 ml/min leak rate the % reduction in leak rate is 100−(1/100×100)=99%.

Embodiments dramatically reduce the amount of work required to be undertaken to maintain a given NP. This for example enables the use of portable NPWT devices with finite pump capacity and/or battery life. A negative pressure efficient sealed dressing is required to dress large or complex wounds such as wounds requiring application of multiple overlapping or adjoined dressings, and geometrically complex wound sites. Such overlapping dressings may be sealed in corresponding manner to skin to dressing seal, and references herein to a skin to dressing seal are of corresponding application to a dressing to dressing seal.

Reference herein to "skin wetting properties" of fluid phase sealant composition is to the ability to flow down into skin crevasses or channels before taking elastomer form. Good skin wetting and dressing wetting properties enable formation of an efficient seal, as hereinbefore defined, by sealant filling channels in the skin and dressing surface, moreover providing an element of adhesion by keying into the skin and dressing surface. Poor skin wetting ability of a composition can be readily observed by the formation of prominent droplets of sealant when dispensed to skin. Preferably a composition has skin wetting properties (preferably once smoothed to simultaneously contact skin and dressing) characterised by a contact angle of a droplet thereof at clean dry skin of less than or equal to 90°, more preferably less than or equal to 45°, more preferably less than or equal to 20°, for example less than or equal to 15'. Thereby poor interaction of composition and skin is substantially limited.

Reference herein to adhesion encompasses adhesion by mechanical means such as mechanical anchoring including wetting of skin or of a dressing surface by dispensable sealant and chemical means such as by application of a chemically adhesive surface. Preferably adhesion is predominantly by interaction of composition at the interface with skin and dressing, with a component of tacky or non-tacky chemical adhesion which enables re-adhesion post cure.

Adhesion of cured composition for use herein is conveniently defined as the peel strength, being the measure of the average force required to part two bonded materials. Preferably the peel strength in relation to parting a dressing sealed to skin or sealed to another dressing at an angle of 180°, is equivalent to that in relation to parting a PICO retention strip adhered to skin or adhered to another dressing, and greater than that in relation to parting a PICO dressing (product code 66800866) adhered to skin or adhered to another dressing. In view of the variability of peeling from skin or a dressing, it is not particularly instructive to measure the force required to part a dressing sealed to steel at an angle of 180°. Preferably peel strength is comparable to that of a PICO retention strip and greater than that of a PICO dressing (product code 66800866). Sealant adhesion may be single use, for example whereby the sealant is not suitable for self-reapplication or enable repeat self-adhesion post curing.

Reference herein to "preferential adhesion" to dressing over skin, or to cohesion greater than adhesion to skin is to such property enabling removal of a dressing with sealant attached, or to removal of residual sealant from skin by simple peeling action, without the need for scrubbing or abrasion of skin. Preferential adhesion refers to adhesion to any part of a dressing to which the sealant composition is intentionally applied, including a skin and/or wound-contacting surface thereof, a border region of the dressing and an upper surface and/or top film. Peeling may be facilitated by provision of a tab or release paper, or may be by gripping by hand or with forceps or the like and peeling back.

Sealant composition is dispensed in concealed or preferably exposed manner, whereby it is covered by a dressing or remains partially or fully exposed. It is therefore important that sealant composition intended for exposed dispensing does not adhere to garments and other objects after curing. This would result at best in inconvenience and at worst in disruption of the sealant and the seal. Accordingly a composition as herein defined preferably cures to a zero to low-tack elastomer.

Tack is a measure of the bond formed rapidly when a material is brought into contact with another surface. The testing was based upon the standards set out in ASTM D2979-01. Preferably the composition has tack as hereinbefore defined in the range 0 to 400 kgf·cm$^{-2}$, preferably 0 to 300 kgf·cm$^{-2}$, more preferably 0 to 250 kgf·cm$^{-2}$, more preferably 0 to 200 kgf·cm$^{-2}$, for example 0 to 175 kgf·cm$^{-2}$. In one embodiment the composition cures to have a zero to low level of tack as hereinbefore defined preferably 0 to 200 kgf·cm$^{-2}$, most preferably 0 to 175 kgf·cm$^{-2}$, for example 0 to 125 kgf·cm$^{-2}$, or 0 to 110 kgf·cm$^{-2}$, or 0 to 100 kgf·cm$^{-2}$.

Optimum results are obtained with selective tack compositions which allow a balance between permitting a degree of readhesion but without incurring a seal failure mode caused by significantly adhering to external objects and promoting resultant dressing edge lift. In a further embodiment therefore the composition cures to have a low level of tack as hereinbefore defined preferably in the range from 40 to 400 kgf·cm$^{-2}$, preferably 40 to 300 kgf·cm$^{-2}$, more preferably 40 to 250 kgf·cm$^{-2}$, more preferably 40 to 200 kgf·cm$^{-2}$, for example 40 to 175 kgf·cm$^{-2}$.

Adhesion by tack increases with prolonged contact under pressure. Whilst an item may not adhere on touch to the composition, adhesion may result from prolonged contact under pressure. Tack as herein defined is recorded with brief touch or "dwell" time.

Tack is measured for a brief contact of probe under very light pressure and composition. However adhesion (by tack) increases with contact time and pressure. In an advantage the composition has zero to low tack during the 1 to 7 days wear of a dressing such that the composition does not preferentially adhere to an external object with which it comes into contact under load (typically limb or body weight) for a period of 30 minutes to 8 hours (sitting, resting or sleeping time). Accordingly the composition should have tack in the range 0 to 400 kgf·cm$^{-2}$, preferably in a range as hereinbefore defined, when cured at 37 C for 1 hour.

In an advantage a film or smoothed bead of cured zero-tack or low tack elastomer when suspended as unsupported elastomer retains its planar shape (i.e. is resiliently deformable, for example does not curl or close in on itself as cling film, and preferentially lies in a straight plane or in a curled plane or cylindrical shape) and is attracted to a surface selected from skin and dressing, disposed a distance of at least approx. 1 cm. This combined shape retention and attraction causes it to preferentially lie as a film against a surface within 1 cm distance than to remain suspended. This holds true for a film suspended adjacent a surface disposed vertically adjacent the suspended film through to an angle of at least 30 degrees from vertical, such that the film or bead is required to lie on gravitationally lower face of the surface. Moreover the film, once attracted to the surface, remains adhered when the surface is oriented horizontally with the film attracted to its lower gravitational face. The attracted film remains preferentially attracted to the surface, and has a reduced attraction to a further skin or dressing surface held out of direct contact within 1 cm thereof. The attracted film is equally attracted to adjacent skin and dressing surfaces such that it will lie across the interface thereof.

This phenomenon enables the composition to form a cured seal which if partially detached at any point will nevertheless not become entrained by other objects in its vicinity, i.e. will not "flap about" and will not place further strain on the integrity of the remaining seal. In addition it continues to have some sealant effect across the skin to dressing interface, which is amplified by the effect of negative pressure at leaks in the interface.

This phenomenon is attributed to effects including the low surface energy environment presented at the silicone surface, localised dipole interactions, viscoelastic properties and the like.

Reference herein to an extensible elastomer is to an elastomer which conforms when subject to movement by a subject wearing the dressing, in preference to cohesive failure of the elastomer. Reference is made in this regard to properties described in respect of the drape of WO 2009/156709, the contents of which are incorporated herein by reference. Preferably a composition cures or is applied to form an elastomer having extensibility which is compatible with and approaches, mimics or approximates to that of skin and/or that of the dressing to be sealed.

This may be determined as a function of its extensibility or tensile strength and elongation at break. Extensibility is defined here as the force required to produce a 20% extension in the length of the material.

On a cured sample with a height of 1 mm the load required to produce a 20% extension at a rate of extension of 300 mm per minute should be less than or equal to 1.4 kgf per cm width (kgfcm$^{-1}$) (guidance set out for surgical dressings in the British Pharmacopoeia (BP), 1993, 14$^{th}$ edition, A222, Appendix XX G), preferably substantially 0 to 1.4 kgfcm$^{-1}$. For a standard tensile testing machine, limit of error is +/−0.01 kgf cm$^{-1}$ in the range 0-1 kg FSL. Accordingly extensibility is 0.001-1.4 (+/−0.01) kgf cm$^{-1}$, preferably 0.001-1.0 (+/−0.01) kgf cm$^{-1}$, more preferably 0.001-0.5 (+/−0.01) kgfcm$^{-1}$, more preferably 0.001-0.2 (+/−0.01) kgf cm$^{-1}$, most preferably 0.001-0.15 (+/−0.01) kgf cm$^{-1}$.

In determining the sample load required to produce a 20% extension, across a specimen of fixed width, then the height of the specimen will dictate the cross sectional area. Defining a realistic height is therefore important in determining appropriate parameters for extensibility.

From the height measurements recorded in the examples, it was observed that the minimum height of the cured silicone product was 0.07 mm and the maximum was 1.58 mm. Where recorded the mean heights of the smoothed-edge products ranged from 0.20 to 0.65 mm.

Whilst there is no strict upper or lower limit for the height of the sealant that could be applied, it seems likely that the sealant will be spread with a height in the range 0.01 to 5.00 mm, more preferably in the range 0.05 to 2.00 mm, with the majority of the sealant likely in the range 0.10 to 1.00 mm.

At the upper end of these three indicative height ranges (under loads in the range of 0.001-1.40 kgf·cm$^{-1}$): a 5.00 mm high sample would require a material with extensibility in the range 0.002-2.80 kgf·cm$^{-2}$; a 2.00 mm high sample would require a material with extensibility in the range 0.005-7.00 kgf·cm$^{-2}$ and a 1.00 mm sample would require a material with extensibility in the range 0.010-14.00 kgf·cm$^{-2}$ With the indicative upper height of the sealant defined this allows the load generated at the skin during extension of the material to be defined and given clear threshold values, minimising the potential for traction damage or discomfort during wear.

Extensibility values in kgfcm$^{-2}$ have been provided below at a range of different loads and sample heights. For ease of comparison they have also been converted into MPa and N mm$^{-2}$.

| | | | | Extensibility values for given loads and silicone heights (kgf · cm$^{-2}$) | | | | | |
|---|---|---|---|---|---|---|---|---|---|
| | | | | Load (kgf · cm$^{-1}$) | | | | | |
| | | | | 1.40 | 1.00 | 0.50 | 0.20 | 0.15 | 0.001 |
| Height descriptor | Likely upper height range (1) | Height (mm) | 5.00 | 2.80 | 2.00 | 1.00 | 0.40 | 0.30 | 0.002 |
| | Likely upper height range (2) | | 2.00 | 7.00 | 5.00 | 2.50 | 1.00 | 0.75 | 0.005 |
| | Max. reported height | | 1.58 | 8.86 | 6.33 | 3.16 | 1.27 | 0.95 | 0.006 |

-continued

| Extensibility values for given loads and silicone heights (kgf · cm$^{-2}$) | | | | | | | |
|---|---|---|---|---|---|---|---|
| | | Load (kgf · cm$^{-1}$) | | | | | |
| | | 1.40 | 1.00 | 0.50 | 0.20 | 0.15 | 0.001 |
| Likely upper height range (3) | 1.00 | 14.00 | 10.00 | 5.00 | 2.00 | 1.50 | 0.010 |
| Max. reported mean height | 0.65 | 21.54 | 15.38 | 7.69 | 3.08 | 2.31 | 0.015 |
| Min. reported mean height | 0.20 | 70.00 | 50.00 | 25.00 | 10.00 | 7.50 | 0.050 |
| Likely lower height range (3) | 0.10 | 140.00 | 100.00 | 50.00 | 20.00 | 15.00 | 0.100 |
| Min. reported height | 0.07 | 200.00 | 142.86 | 71.43 | 28.57 | 21.43 | 0.143 |
| Likely lower height range (2) | 0.05 | 280.00 | 200.00 | 100.00 | 40.00 | 30.00 | 0.200 |
| Likely lower height range (1) | 0.01 | 1400.00 | 1000.00 | 500.00 | 200.00 | 150.00 | 1.000 |

Accordingly Extensibility on a 1.00 mm high sample is 0.001-14.00 kgfcm$^{-2}$, preferably 0.001-10.00 kgfcm$^{-2}$, more preferably 0.001-5.00 kgfcm$^{-2}$, more preferably 0.001-2.00 kgfcm$^{-2}$, most preferably 0.001-1.50 kgfcm$^{-2}$.

| Extensibility values for given loads and silicone heights (MPa) | | | | | | | | |
|---|---|---|---|---|---|---|---|---|
| | | | | Load (kgf · cm$^{-1}$) | | | | |
| | | | | 1.40 | 1.00 | 0.50 | 0.20 | 0.15 | 0.001 |
| Height descriptor | Likely upper height range (1) | Height (mm) | 5.00 | 0.27 | 0.20 | 0.10 | 0.04 | 0.03 | 0.000 |
| | Likely upper height range (2) | | 2.00 | 0.69 | 0.49 | 0.25 | 0.10 | 0.07 | 0.000 |
| | Max. reported height | | 1.58 | 0.87 | 0.62 | 0.31 | 0.12 | 0.09 | 0.001 |
| | Likely upper height range (3) | | 1.00 | 1.37 | 0.98 | 0.49 | 0.20 | 0.15 | 0.001 |
| | Max. reported mean height | | 0.65 | 2.11 | 1.51 | 0.75 | 0.30 | 0.23 | 0.002 |
| | Min. reported mean height | | 0.20 | 6.86 | 4.90 | 2.45 | 0.98 | 0.74 | 0.005 |
| | Likely lower height range (3) | | 0.10 | 13.73 | 9.81 | 4.90 | 1.96 | 1.47 | 0.010 |
| | Min. reported height | | 0.07 | 19.61 | 14.01 | 7.00 | 2.80 | 2.10 | 0.014 |
| | Likely lower height range (2) | | 0.05 | 27.46 | 19.61 | 9.81 | 3.92 | 2.94 | 0.020 |
| | Likely lower height range (1) | | 0.01 | 137.29 | 98.07 | 49.03 | 19.61 | 14.71 | 0.098 |

Accordingly Extensibility on a 1.00 mm high sample is 0.001-1.37 MPa, preferably 0.001-0.98 MPa, more preferably 0.001-0.49 MPa, more preferably 0.001-0.20 MPa, most preferably 0.001-0.15 MPa (which can also be expressed as 0.001-1.37 N · mm$^{-2}$, preferably 0.001-0.98 N · mm$^{-2}$, more preferably 0.001-0.49 N · mm$^{-2}$, more preferably 0.001-0.20 N · mm$^{-2}$, most preferably 0.001-0.15 N · mm$^{-2}$).

Elongation at break is defined here as the maximum % extension of the material when under tension (sample extension/original length×100).

On a cured sample elongation at break may be greater than or equal to 50%, preferably 50% to 50000%, more preferably 100%-5000%, more preferably 100%-1200%, for example 50% to 1200% or 150%-1200% or 200%-1200%.

Tensile strength is a measure of the stiffness of an elastic material and is the ratio of stress given as force per unit area to strain which is dimensionless. Preferably tensile strength is greater than 5 kgfcm$^{-2}$, more preferably is greater than 15 kgfcm$^{-2}$, more preferably greater than 25 kgfcm$^{-2}$, for example is in a range including from 25 kgfcm$^{-2}$ to at least 50 or 100 kgfcm$^{-2}$.

An important property for the sealant is the elasticity of the material such that it extends in response to an applied load yet recovers original dimensions after removal of the extending load. Suitably sealant elasticity is compatible with or corresponds to that of the surface to which the sealant has been applied, i.e. the skin and/or wound surface, dressing or body part or limb to which it is applied. Permanent set or tensile set is defined here as the ability of the cured material to regain its original length following extension for 1 minute.

On a cured sample permanent set should be less than or equal to 1000%, preferably 20% to substantially 0% following an elongation of 300% or 500%. Conveniently a measure is made at elongation of 20% and has the same or values or lower values than those at elongation of 300% to 500%

In the context of dispensing a composition or sealant, reference herein to a bead of composition or sealant encompasses composition or sealant dispensed to a point, such as at an interface, or along the line of an interface, or within a skin defect or cavity for example as a discrete or continuous seal. This has the visual appearance of a spherical spot or dab, or elongate line or bead, or in-fill as known in the art of sealant or filler application.

Reference herein to a border region of a dressing is as known in the art of advanced wound management wound care, for example ALLEVYN™ Gentle Border (Smith & Nephew), Mepilex (Mölnlycke), PICO™ (Smith & Nephew). Suitably a border region denotes a border about a dressing at its periphery. The border is intended to only contact intact skin about a wound, and encloses a central portion intended to contact a wound and some skin thereabout. The border region may include an adhesion promoting region, hereinafter a peripheral region, over part or all of the border. An adhesion promoting peripheral region may be located at either surface of the dressing unless otherwise indicated. An adhesion promoting peripheral region may be present at a minimum surface area. Alternatively it may be cheaper to reproduce a property intended for an adhesion promoting peripheral region over an entire dressing surface rather than limit to that region or part thereof as a means to confer different properties on that region. An adhesion promoting peripheral region may be of any desired cross-sectional area to confer a desired property.

The composition addresses providing a seal interfacing a junction between skin and dressing, preferably also providing a seal interfacing a junction between overlapping dressings. In a particular advantage we have found that the composition functions admirably for the dual purpose of sealing dressing to skin or sealing two dressings at their overlap.

It will be understood that embodiments are generally applicable to use in advanced wound management. Briefly, Advanced Wound Management addresses wounds providing wound specific care by means of the dressings used, for example in relation to wound dressings which are tailored to include specific provision for i.a. management of wound exudates (ALLEVYN, DURAFIBER, Gentle Border), infection management (ACTICOAT, IODOSORB), iv site care (IV3000), management of compromised skin about the wound, NPWT (RENASYS F/AB, PICO), post operative care such as surgical drapes (OPSITE), temporary bioskin dressings (BIOBRANE) and the like. Advanced wound management dressings include for example Gentle Border® dressings, amongst others. One aspect of Advanced Wound Management is TNP therapy which assists in the management, closure and/or healing of many forms of wounds by reducing tissue oedema; encouraging blood flow and granular tissue formation; removing excess exudate and may reduce bacterial load (and thus infection risk). TNP therapy systems may also assist in the healing of surgically closed wounds by removing fluid and by helping to stabilise the tissue in the apposed position of closure. A further beneficial use of TNP therapy can be found in grafts and flaps where removal of excess fluid is important and close proximity of the graft to tissue is required in order to ensure tissue viability. Embodiments are more particularly applicable to use in topical negative pressure (TNP) therapy systems and the like.

It will be appreciated that throughout this specification reference is made to a wound. In this sense it is to be understood that the term wound is to be broadly construed and encompasses open and closed wounds in which skin is torn, cut or punctured such as points of venous access, or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, cosmetic wounds, trauma and venous ulcers or the like. Wounds addressed with particular emphasis herein are wounds on or adjacent topographically complex locations of the body in particular, including heel, sacrum, axial, inguinal, shoulder, neck, foot, digits, knee, elbow, hands and other contoured topographical sites, and creviced sites.

Composition and Method for Dispensing

In one embodiment the composition may comprise any polymers that follow a hydrosilylation reaction. One polymer (i) preferably contains alkenyl groups, the other (ii) preferably contains Si—H moieties. The group of siloxane polymers is based on a structure comprising alternate silicon and oxygen atoms with various organic moieties attached to the silicon. Curing can be defined as a treatment that decreases the flow of an elastomer. This change is generally brought about by linking reactions between polymer molecules. Where the silicon hydride (Si—H) moiety is part of a polysiloxane, it is possible for the alkenyl group to either be part of a siloxane polymer or otherwise part of a non-siloxane polymer. The position of the alkenyl functional group is not critical and it may be either at the molecular chain terminals or in non-terminal positions along the molecular chain.

Polymers (i) and/or (ii) are commercially available or may be obtained by known techniques. Suitably polymers (i) and/or (ii) are independently selected from known and novel fluid phase homopolymeric, and copolymeric polymers, and their entangled systems and mixtures thereof. The compositions, in turn, cure to form copolymers, and may also include their entangled systems and mixtures with other non-reactive polymers if present in the composition.

Copolymeric polymers include all hybrids derived from two or more monomeric species, including alternating, periodic, statistical, random, block, linear, branched, star, graft and pendant copolymers. Entangled systems include interpenetrating networks (IPNs) and semi-interpenetrating networks (SIPNs). It is also the case that these polymers can incorporate both organic and inorganic moieties.

Preferably polymers (i) and (ii) are selected from silicones, including siloxanes and modified siloxanes, polyurethanes (PU) including polyester and polyether urethanes, elastomeric polyether polyesters, polyglycolic acid, polyacetates such as ethyl vinyl acetate, polyacrylate, polyacid derivatives of polysaccharides, such as carboxyalkylcellulose, carboxyalkylchitosan and copolymers thereof, and their hybrids including copolymers, entangled systems and mixtures thereof.

The composition may make use of an addition cure reaction between organohydrogensiloxane units and organoalkenylsiloxane units. These units may be incorporated into a wide range of polymeric, copolymeric, entangled and mixed polymers as hereinbefore defined. Preferred siloxane polymers (i) and (ii) therefore include these respective units and are more preferably polyorganosiloxanes. Polymer (i) is preferably a polydiorganosiloxane polymer comprising alkenyl-containing units, more preferably is a polydiorganoalkenylsiloxane polymer. Preferably polymer (ii) is a polydiorganosiloxane polymer comprising SiH units, more preferably is a polydiorganohydrogensiloxane polymer.

Examples of hybrid organic-inorganic polymeric systems that have used both siloxane and organic units include: acrylate functionalized siloxane copolymers, which have found use in contact lenses (U.S. Pat. No. 3,808,178); hybrid grafts where organic polymers are grafted onto a polysiloxane chain or where siloxanes are grafted onto organic polymers, for example in silane graft technology for cross linkable HDPE (U.S. Pat. No. 3,646,155) where hybrid grafts have been used to allow the cross linking of organic polymers through siloxane bond formation; hybrid block copolymers for example silicone-polycarbonate block copolymers (U.S. Pat. No. 3,274,155); and copolymers of hybrids of silicone and ethylene copolymers, cross-linked with vinyl-containing silicone copolymers which have found use in coating textiles (US 2005/0100692);

IPNs represent a special class of hybrid polymeric systems, these systems use a combination of mechanical entanglement and crosslinking in which one polymer is cured about another; these include thermoplastics entangled with platinum catalyzed addition cure silicones such as silicone-urethane IPNs and semi-IPNs including silicone-urethane and silicone-polyamide systems which are of general application or have found specific use in coating textiles (U.S. Pat. Nos. 4,714,739, 7,543,843); hydrophilic components immobilised in a silicone polymer (U.S. Pat. No. 5,397,848) which have found use as contact lens material; and silicone polymer cured about a non-reactive polymer of comparable adhesion, which have found use in coating textiles (U.S. Pat. No. 7,132,170).

Polymers may also be selected from modified silicones (MS) which find use as adhesives in catheter tubing and the like.

Preferred compositions comprise a polydiorganosiloxane polymer (i) and/or (ii) and/or their respective combinations with the aforementioned polymers. A composition in which polymers comprise or consist essentially of polydiorganosiloxane polymers (i) and (ii) has particular advantages, for example in applications where low toxicity is an advantage, preferably in medical or dental applications or in non-medical or non-dental applications requiring low toxicity or favorable biocompatibility.

Alternatively or additionally polymers (i) and (ii) are as commercially available (Silpuran 2445 A/B, and the like) or variants thereof, optimised for viscosity, cure time, tack and optionally other properties as hereinbefore defined.

Polymer (i) and (ii) may comprise respective alkenyl-containing units and organohydrogensiloxane units situated along the length of polymer chains, and/or as polymer chain end-capping units or a combination thereof. Polymer (i) in-chain and end-capping alkenyl units preferably comprise alkenyl group or moiety $R^{Alk}$ selected from $C_{2-20}$ alkenyl optionally substituted or including one or more aryl groups or moieties. $R^{Alk}$ may comprise terminal or non terminal unsaturation, and may be of the formula i-I:

$$-R^{Alk1}-CR^{Alk1}=CR^{Alk2}{}_2 \qquad \text{(i-I)}$$

in which the groups $R^{Alk1}$ and $R^{Alk2}$ are independently selected from H, $C_{1-20}$ alkyl and $C_{5-20}$ aryl groups and combinations thereof and a moiety $R^{Alk1}$ is selected from a single bond, $C_{1-20}$ alkyl and $C_{5-20}$ aryl groups and combinations thereof. One of $R^{Alk2}$ may be a moiety linking to polymer chain. More preferably each $R^{Alk}$ is independently selected from vinyl, allyl, propenyl, and from terminally and non-terminally unsaturated butenyl, pentenyl, hexenyl, heptenyl, octenyl, nonenyl and decenyl groups, most preferably selected from vinyl and hexenyl groups.

Preferably polymer (i) comprises a polydiorganosiloxane polymer or copolymer comprising alkenyl-containing units of the formula (i-Ii):

≡Si—$R^{Alk}$, more particularly of the formula (i-III) and/or (i-IV): (i-II)

—O—SiR$^1$R$^{Alk}$—O— (i-III)

—O—SiR$^1{}_2$R$^{Alk}$ (i-IV)

wherein $R^{Alk}$ is as hereinbefore defined and one or more groups $R^1$ are organo groups suitably independently selected from alkyl and aryl groups, more preferably $C_{1-20}$ alkyl and $C_{5-20}$ aryl groups and combinations thereof, for example from methyl, ethyl, propyl, butyl, pentyl, hexyl, heptyl, octyl, nonyl and/or decyl groups and moieties.

More particularly polymer (i) is selected from the formula i-V and i-VI:

$$P^i\text{—}O\text{—}SiR^1R^{Alk}\text{—}O\text{—}P^i \qquad \text{i-V:}$$

$$P^i\text{—}O\text{—}SiR^1{}_2R^{Alk} \qquad \text{i-VI}$$

wherein $P^i$ denotes the remainder of the polymer chain which may incorporate same or different units, and $R^1$ is as hereinbefore defined.

Polymer (i) may also comprise a polyorganosiloxane exhibiting, per molecule, at least two $C_2$-$C_6$ alkenyl groups bonded to the silicon and having, for example, a viscosity of between 10 and 300 000 mPa·s, that is to say 0.01 to 300 Pa·s, such that when combined in Part A with further Part A components and optionally additionally in Part B with further Part B components, Part A, and Part B as appropriate, is (are) of viscosity in a range as hereinbefore defined, which can in particular be formed of at least two siloxyl units of formula:

$$Y_d R_e SiO_{\frac{(4-d-e)}{2}} \qquad \text{(III)}$$

in which:
Y is a $C_2$-$C_6$ alkenyl such as vinyl, allyl or hexenyl groups, preferably vinyl,
R is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
d is 1 or 2, e is 0, 1 or 2 and d+e=1, 2 or 3,
optionally all the other units being units of average formula:

$$R_f SiO_{\frac{4-f}{2}} \qquad \text{(IV)}$$

in which R has the same meaning as above and f=0, 1, 2 or 3.

Examples of polymer (i) are, for example, dimethylpolysiloxanes comprising dimethylvinylsilyl ends, (methylvinyl)(dimethyl)polysiloxane copolymers comprising trimethylsilyl ends or (methylvinyl)(dimethyl)polysiloxane copolymers comprising dimethylvinylsilyl ends.

A convention accepted in the art for denoting the units of silicones according to the number of oxygen atoms bonded to the silicon is used here. This convention uses the letters M, D, T and Q (abbreviations for "mono", "di", "tri" and "quatro") to denote this number of oxygen atoms. This nomenclature of silicones is described, for example, in the work by Walter Noll, "Chemistry and Technology of Silicones", Academic Press, 1968, 2nd edition, on pages 1 to 9.

Polymer (i) may also be a silicone resin bearing at least two alkenyl, preferably vinyl groups. Such silicone resin comprising at least two different siloxane units chosen from those of M siloxane unit of formula $R_3SiO_{1/2}$, D siloxane unit of formula $R_2SiO_{2/2}$, T siloxane unit of formula $RSiO_{3/2}$ and Q siloxane unit of formula $SiO_{4/2}$, wherein R denotes a monovalent hydrocarbon group, with the conditions that at least one of these siloxane units being a T or Q siloxane unit and that at least two of the M, D and T siloxane units comprises an alkenyl group.

The silicone resin could be selected from the group consisting of:

an organopolysiloxane resin of formula $MT^{Vi}Q$ consisting essentially of:
(a) trivalent siloxane units $T^{Vi}$ of the formula $R'SiO_{3/2}$;
(b) monovalent siloxane units M of the formula $R_3SiO_{1/2}$, and
(c) tetravalent siloxane units Q of the formula $SiO_{4/2}$ an organopolysiloxane resin of formula $MD^{Vi}Q$ consisting essentially of:
(a) divalent siloxane units $D^{Vi}$ of the formula $RR'SiO_{2/2}$;
(b) monovalent siloxane units M of the formula $R_3SiO_{1/2}$, and
(c) tetravalent siloxane units Q of the formula $SiO_{4/2}$ an organopolysiloxane resin of formula $MDD^{Vi}Q$ consisting essentially of:
(a) divalent siloxane units $D^{Vi}$ of the formula $RR'SiO_{2/2}$;
(b) divalent siloxane units D of the formula $R_2SiO_{2/2}$
(b) monovalent siloxane units M of the formula $R_3SiO_{1/2}$, and
(c) tetravalent siloxane units Q of the formula $SiO_{4/2}$ an organopolysiloxane resin of formula $M^{Vi}Q$ consisting essentially of:
(a) monovalent siloxane units $M^{Vi}$ of the formula $R'R_2SiO_{1/2}$; and
(b) tetravalent siloxane units Q of the formula $SiO_{4/2}$, and an organopolysiloxane resin of formula $M^{Vi}T^{Vi}Q$ consisting essentially of:
(a) monovalent siloxane units $M^{Vi}$ of the formula $R'R_2SiO_{1/2}$;
(b) trivalent siloxane units $T^{Vi}$ of the formula $R'SiO_{3/2}$, and
(c) tetravalent siloxane units Q of the formula $SiO_{4/2}$ wherein R denotes a monovalent hydrocarbon group such as methyl and R' denotes a vinyl group:

Such resins are well-known branched organopolysiloxane oligomers or polymers which are commercially available. They are provided in the form of solutions, preferably siloxane solutions.

Polymer (ii) in-chain and end-capping polyorganohydrogensiloxane units are preferably selected from the formula ii-I and ii-II:

     ii-I

—O—SiR²₂H, more preferably polymer (ii) is selected from formula ii-III and ii-IV:     ii-II

     ii-III

 wherein     ii-IV $P^{ii}$ denotes the remainder of the polymer chain which may incorporate same or different units and one or more groups $R^2$ are organo groups suitably independently selected from $C_{1-20}$ alkyl, $C_{5-20}$ aryl and combinations thereof, for example from methyl, ethyl, propyl, butyl, pentyl, hexyl, heptyl, octyl, nonyl and/or decyl groups.

Polymer (ii) preferably comprises a polyorganohydrogensiloxane-polydiorganosiloxane copolymer, incorporating one or more units ii-I and/or ii-II:

     ii-I

—O—SiR²₂H and one or more units ii-V and/or ii-VI:     ii-II

     ii-V

     ii-VI wherein $R^2$ is as hereinbefore defined, more preferably copolymer incorporating polyorganohydrogensiloxane end-capping units, i.e polymer chains terminate with the group or moiety ii-VII:

≡Si—H, more particularly with the unit of formula ii-II:     ii-VII

—O—SiR²₂H as hereinbefore defined. Most preferably polymer(ii) comprises methylhydrogensiloxane-dimethylsiloxane copolymers.     ii-II Polymer (ii) may also comprises a polyorganosiloxane, exhibiting, per molecule, at least two hydrogen atoms bonded to the silicon and preferably at least three ≡SiH units and having, for example, a viscosity of between 1 and 5000 mPa·s, that is to say between 0.001 and 5 Pa·s, up to 300 Pa·s as hereinbefore defined, such that when combined in Part B with further Part B components, Part B is of viscosity in a range as hereinbefore defined, which can in particular be formed of siloxyl units of formula:

$$H_g X_i SiO_{\frac{4-g-i}{2}} \quad (V)$$

in which:
X is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
g=1 or 2, preferably =1, i=0, 1 or 2 and g+i=1, 2 or 3,
optionally all the other units being units of average formula:

$$X_j SiO_{\frac{4-j}{2}} \quad (VI)$$

in which X has the same meaning as above and j=0, 1, 2 or 3.

Examples of polymer (ii) are polymethylhydrosiloxanes or methylhydrodimethylsiloxane copolymers.

In the case that polymers include other units additional to iIII, iIV, iiI and iiII for example, these are suitably not reactive with the respective polymer at ambient temperature or under sterilising conditions.

Suitably the ratio of silicon-bonded hydrogen atoms provided by (ii) to silicon-bonded alkenyl moieties provided by (i) is at least 0.5:1, preferably 1:1, Preferably embodiments of the curable composition follow the catalysed addition cure reaction according to the following scheme:

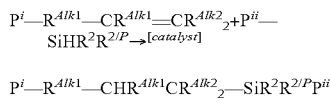

more preferably:

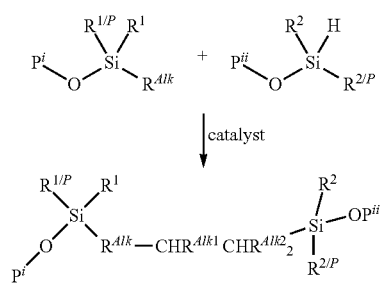

wherein integers are as hereinbefore defined and $R^{1/P}$ is selected from $P^i$ and $R^1$ as hereinbefore defined and $R^{2/P}$ is selected from $P^{ii}$ and $R^2$ as hereinbefore defined.

The polymers (i) and (ii) and catalyst (iii) may be apportioned in at least one Part A and at least one Part B in manner to provide respective Parts A and B which in isolation are not reactive at ambient temperature, nor under sterilisation conditions, such as heat or radiation. Apportioning may also be determined according to volume and viscosity.

Preferably polymers (i) and (ii) and catalyst (iii) are apportioned in at least one Part A and at least one Part B in manner such that polymer (ii) is absent from Part A and polymer (i) is absent from Part B or Part B incorporates a trace amount of polymer (i) represented as molar ratio (Si—H unit or moiety)/(alkenyl unit or moiety) of greater than or equal to 2000. Such composition may be sterilised at effective gamma or radiation dose for example as disclosed in WO2012/069794, the contents of which are incorporated herein by reference.

The at least one Part A and at least one Part B may be of substantially equal volume and viscosity or of different volume and/or viscosity. Part A or Part B may incorporate a suitable viscosity moderator or diluent, in amount to increase or reduce volume and/or viscosity. By this means Part A and Part B having different volume and viscosity may be volume and viscosity matched for improved ease and intimacy of mixing and dispensing. A suitable diluent is for example a silicone oil which is available in any desired viscosity for thickening or thinning effect. Alternatively or additionally at least one Part A and at least one Part B are sealed in respective receptacles or on respective supports which are thermally stable at an elevated temperature of 121° C. or more for a period of up to 28 hours, for example as disclosed in WO2012/069793, the contents of which are incorporated herein by reference.

The composition may thereby be rendered terminally sterile by being sterilised in its primary packaging and this property may be characterised by a Sterility Assurance Level (SAL). The SAL is defined in ISO 11139:2006 as the probability of a single viable microorganism occurring on an item after sterilization. The term SAL takes a quantitative value, in the format of $10^{-n}$, where typically n=3, 4, 5 or 6, preferably SAL=$10^{-3}$ or $10^{-6}$.

A catalyst as hereinbefore defined may be any catalyst which is effective in catalysing the addition curing reaction as hereinbefore defined, more preferably as hereinabove illustrated. Suitable catalysts are selected from any known form of platinum, rhodium, palladium, nickel and like addition curing hydrosilylation catalysts, for example as disclosed in U.S. Pat. No. 5,153,231, US 2006/0217016, U.S. Pat. Nos. 3,928,629 and 4,529,553 the contents of which are incorporated herein by reference.

A platinum catalyst may be selected from platinum black, platinum as deposited on carriers including silica such as silica gel or carbon such as powdered charcoal, platinic chloride or chloroplatinic acid and alcohol solutions thereof, salts of platinic and chloroplatinic acids and platinum complexes such as platinum/olefin, platinum/alkenylsiloxane, platinum/beta-diketone, platinum/phosphine and the like. Chloroplatinic acid may be the hexahydrate or anhydrous form. A platinum complex may be prepared from chloroplatinic acid and its hexahydrate, or from platinous chloride, platinum dichloride, platinum tetrachloride and their neutralised complexes with divinyltetramethyldisiloxane, optionally diluted with dimethylvinylsiloxy endcapped polydimethylsiloxane.

A palladium catalyst may be selected from palladium on carbon, palladium chloride and the like.

A rhodium catalyst may be selected from rhodium chloride and one or more complexes of rhodium having the general formula iii-I or iii-II:

 (iii-I)

 (iii-II)

wherein each X represents a halogen atom and each R represents an alkyl or aryl radical or combination thereof having from 1 to 8 inclusive carbon atoms or the $R'_3SiQ$ group in which Q represents a divalent aliphatic hydrocarbon radical having from 1 to 6 inclusive carbon atoms and R' represents an alkyl or aryl radical or combination thereof having from 1 to 8 inclusive carbon atoms or a $(CH_3)_3Si$— group, not more than one R' per molecule being $(CH_3)_3Si$—. For example rhodium chloride/di(n-butyl)sulfide complex and the like.

A nickel catalyst is preferably a zero valent nickel selected from $M_2Ni^{(0)}$ such as bis(1,5-cyclo-octadienyl) nickel $(Ni(COD)_2)$ and from $MNi^{(0)}G$ wherein M is a bidentate alkene cyclic hydrocarbon ring of $C_{8-12}$ and G is selected from monodentate and bidentate phosphorous groups having hydrogen atoms, substituted or unsubstituted hydrocarbon radicals or mixtures thereof bonded to the phosphorous atoms of the phosphorous groups.

The composition may include a catalyst inhibitor. Suitable inhibitors are known in the art. For example a catalyst inhibitor may be selected from a polymethylvinylsiloxane cyclic compound and an acetylenic alcohol, such as methyl butynol for example as in Cavi-Care or disclosed in U.S. Pat. No. 5,153,231, the contents of which are incorporated herein by reference.

Preferably the composition comprises an addition-reaction retardant or a crosslinking inhibitor chosen, for example, from the following compounds:
  polyorganosiloxanes substituted with at least one alkenyl that may optionally be in cyclic form, tetramethylvinyltetrasiloxane being particularly preferred,
  organic phosphines and phosphites,
  unsaturated amides,
  alkyl maleates, and
  acetylenic alcohols.

These acetylenic alcohols (see FR-A-1 528 464 and FR-A-2 372 874), which are among the preferred thermal blockers of the hydrosilylation reaction, have the formula:

(R')(R")C(OH)—C≡CH in which formula
R' is a linear or branched alkyl radical, or a phenyl radical;
R" is H or a linear or branched alkyl radical, or a phenyl radical; the radicals R', R" and the carbon atom alpha to the triple bond possibly forming a ring; and
the total number of carbon atoms contained in R' and R" being at least 5 and preferably from 9 to 20.
Examples that may be mentioned include:
1-ethynyl-1-cyclohexanol;
3-methyl-1-dodecyn-3-ol;
3,7,11-trimethyl-1-dodecyn-3-ol;
1,1-diphenyl-2-propyn-1-ol;
3-ethyl-6-ethyl-1-nonyn-3-ol;
2-methyl-3-butyn-2-ol;
3-methyl-1-pentadecyn-3-ol.

These α-acetylenic alcohols are commercial products. Such a retardant is present in a maximum proportion of 3000 ppm relative to the total weight of the polyorganosiloxanes in the silicone composition. Methyl butynol could be chosen as in Cavi-Care.

The composition may be non-foamable or may be foamable, comprising (iv) a blowing agent, selected from any agent which evolves gas or vapour as part of or during the curing reaction, for example selected from H-donors, OH-containing agents, H-bonding agents such as:
  alcohols including methanol, ethanol, n-propanol, isopropanol, n-butanol, 2-butanol, tert-butanol, n-hexanol, n-octanol and benzyl alcohol. n-Propanol, n-butanol, n-hexanol and n-octanol are particularly preferred,
  polyols such as diols including, 4-butanediol, 1,5-pentanediol and 1,7 heptanediol,
  silane or polysilane having at least one silanol group, or water.

The composition forms, after hydrosilylation, a silicone elastomer which may be foaming or have gel properties. The term "silicone gel" denotes a crosslinked silicone product characterized by a degree of penetration of, for example, between 20 and 500 tenths of a mm (measured by ASTM D 2137 penetrometry, weight of the rod and of the cone: 62.5 g).

When the composition is prepared for a silicone gel it may have at least one nonfunctionalized polyorganosiloxane comprising:
a) end siloxyl units of type $M=(R^6)_3SiO_{1/2}$
in which the $R^6$ radicals which are identical or different, correspond to an optionally substituted linear or branched $C1-C_6$ alkyl group and/or a substituted or unsubstituted aryl group, and
b) identical or different siloxyl units of type $D=(R^7)_2SiO_{2/2}$
in which the $R^7$ radicals correspond to the same definition as $R^6$.

The physical properties of these gels are adjusted according to the use by varying the levels of siloxyl units carrying Si-alkenyl and SiH functional groups and when it is present by varying the percentage by weight of nonfunctionalized polyorganosiloxane, which is well known in the prior art.

To enhance the adhesive properties of a silicone gel, the composition can further comprises a monofunctional polyorganosiloxane carrying a single Si-alkenyl group per molecule as taught by European patent application EP-1633830-A2.

Further, a composition may also comprise inorganic filler such as reinforcing or bulking fillers. These fillers can be provided in the form of very finely divided products, the mean particle diameter of which is less than 0.1 μm. These fillers include in particular fumed silicas and precipitated silicas; their specific surface is generally greater than 10 m²/g and generally lies within the range 20-300 m²/g.

These fillers can also be provided in the form of more coarsely divided products, with a mean particle diameter of greater than 0.1 μm. Mention may in particular be made, as examples of such fillers, of ground quartz, calcium carbonate, diatomaceous silicas, calcined clay, titanium oxide of the rutile type, iron, zinc, chromium, zirconium or magnesium oxides, the various forms of alumina (hydrated or nonhydrated), boron nitride, lithopone or barium metaborate; their specific surfaces are generally less than 30 m²/g.

The filler may have a hydrophobic surface, which may be obtained by treating the filler, e.g. with suitable silanes, short chain siloxanes, fatty acids or resinous silicone materials. Hexamethyldisilazane treated fumed silica may be considered, or if translucence is to be maintained, vinyl "Q" reinforcing resins may be used. A filler may be hydrophobic. Suitable materials and processes for rendering the surface of fillers hydrophobic have been described in the literature, and are known to the person skilled in the art. The fillers can also be composed of a mixture of several types of fillers with different particle sizes.

The composition may comprise a thixotropic agent. A thixotropic agent confers on a composition properties whereby it becomes viscous during application and reverts to higher viscosity after application when no longer being worked. Thixotropes include fillers such as silica, and certain silicone-based substances.

A composition may include additional components including other adjuvants, preservatives including propyl gallate, extenders, rheology regulators, adhesion promoters or adhesion reducers, moisture vapor permeability (MVP) or moisture vapor transmission rate (MVTR) promoters to prevent maceration of skin having composition applied thereto, whereby skin can transpire and pass liquid but still function as a sealant and bacterial barrier, and the like. Suitably such additional components confer properties as hereinbefore defined on the composition.

Advantageously for example a composition comprises skin wetting properties as hereinbefore defined, whereby an effective seal may be provided, blocking microchannels generated between the skin and a wound dressing.

The composition has extensibility as hereinbefore defined. A desired extensibility is conferred as known in the art by adapting polymer cross-linking or chain-length, filler content, chain entanglement and the like.

The composition may comprise active agents, which may have any desired activity for the intended purpose, and include active pharmaceutical ingredients (API's) and the like.

Antimicrobial agents, biocides and disinfectants may be selected from silver, in particular nano crystalline silver, and derivatives including silver complexes and salts such as ionic silvers, silver zeolite, silver oxide, silver nitrate, silver acetate, silver chloride, silver sulphadiazine), biguanides including polyhexamethylene biguanide, chlorhexidine digluconate and its acetate salts chlorhexidine acetate and diacetate, manuka honey, peroxides (e.g. hydrogen peroxide), iodine (e.g. povidone iodine), sodium hypochlorite, copper, copper complexes; zinc (e.g. zinc oxide, zinc pyrithione), gold, gold complexes; phosphates, amines, amides and sulphonamides (e.g. hexatidine, proflavine. mafenide, nitrofurazone, norfloxacin); antibiotics (e.g. gentamicin, bacitracin, rifampicin; alcohols and acids (e.g. ethanol, phenoxy ethanol, mupirocin).

Nutrients, pain killers and other pain management techniques suitably include analgesics and anasthetics and may be selected from amethocaine, lignocaine, non-steroidal anti-inflammatory drugs, anti inflammatories such as hydrocortisone, paraffin to reduce adherence to the skin, urea to reduce dehydration of the skin; buffering components to promote healing of the skin.

Heamostats may be selected from chitin, chitosan, kaolin; antifibrinolytics such as amino acids, aminocaproic acid, tranexamic acid, aminomethylbenzoic acid; Proteinase inhibitors including aprotinin, alfa1 antitrypsin, C1-inhibitor, camostat; Vitamin K and other hemostatics including vitamin K, phytomenadione, menadione; fibrinogen including human fibrinogen; local hemostatics including absorbable gelatin sponge, oxidized cellulose, tetragalacturonic acid hydroxymethylester, adrenalone, thrombin, collagen, calcium alginate, epinephrine; blood coagulation factors including coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa (activated), nonacog alfa, thrombin and systemic hemostatics: etamsylate, carbazochrome, batroxobin, romiplostim, eltrombopag.

Active agents may further include combination materials including superabsorbers, odour management agents, wovens and non wovens, gellable fibres; growth factors, wound debridements—mechanical, autolytic and enzymatic; resorbable dressings and micro structure to influence cell ingrowth; cells, tissue (e.g. autologous treatments); indicators; dyes and colourants and coloured indicators, whiteners such as zinc oxide and titanium oxide.

The composition may be in a form that it may be applied to skin or dressing in any known manner, such as by pallet knife, syringe, roll-on applicator, spray, wipe, brush, foam, sponge, non-woven, part integrated or fully integrated into dressing, or manually applied. An applicator using a sponge is demonstrated with Chloraprep i.e. http://www.chloraprep.co.uk. For a two part curing system that requires mixing, a double barrelled syringe with a mixing head could be employed.

Preferably therefore the composition is provided as at least one Part A and at least one Part B sealed in or on respective receptacles or supports suitable for cooperatively dispensing from a cooperative dispensing device, preferably sealed in respective barrels or respective cassettes for a double barrel syringe, more preferably provided together with a cooperating dispensing device.

More preferably a double barrelled syringe with a mixing head and a spreader tip to allow spread of material may be used (e.g. Double-Syringe Prefilled Delivery System (L-System), Medmix Systems Ag, fitted with static mixer and spreader tip http://www.medmix.ch/L-SYSTEM.html).

For certain embodiments there is a clear advantage in using an applicator with an integral spreader. Where material is applied directly to the junction between the skin and the dressing edge it is advantageous to manipulate this material to ensure optimal placement. An integral spreader minimises cross contamination when the sealant is manipulated. During the manipulation cross contamination could relate to: contamination of the sealant with a microbiological burden, contamination of the sealant with foreign bodies, contamination of the sealant with chemicals (such chemicals may have an influence on the sealant) and contamination of personnel or equipment with the sealant. For other embodiments there is advantage in using an applicator without a spreader, for example for filling body crevices etc.

Where the composition is a curing system chemical contamination may adversely affect the cure process. For example where the composition is a platinum catalysed RTV-2 silicone, contact with latex or nitrile containing gloves may affect the curing. The problem caused by the example given has been documented in the dental press with regards to the delayed setting of polyvinyl siloxane dental impression materials when mixed with certain types of glove (Y. Walid, Z. AI-Ani and R. Gray, Silicone impression materials and latex gloves. Is interaction fact or fallacy?, Dent Update, 2012, 39, pp. 39-42).

In a medical setting an integral applicator with spreader therefore overcomes the obstacle of a clinician being unable to use a gloved finger (subject to the chemical composition of the glove) to manipulate the sealant, overcomes the possibility of using an ungloved finger, thus eliminating direct hand to patient contact (not only would this approach be inappropriate for most clinical settings, it would likely result with transfer of the curing composition to the clinician's fingertip) and overcomes the requirement to contaminate any other medical devices or implements with the curing composition.

In the case of a curing system the sealant may have flow properties such that it can be drawn into defects by the negative pressure and then cure. The cured sealant preferably retains a degree of flow or conformability such that it can accommodate the dynamic conditions encountered when on the skin.

Removal properties of the cured composition are a further consideration. Preferably it should have properties allowing it to be removed substantially in one piece. Preferably the sealant can be removed with adhesion to the dressing or drape.

The sealant may be non-foaming or may have a degree of foaming or expansion to expand into crevices, skin or dressing defects. It may have flow properties such that it could be drawn into defects by the negative pressure.

The properties during wear are key to the effectiveness of the seal. The sealant located at the skin-dressing interface should key to the skin and dressing, but not be so tacky (or adhesive) once cured so as to preferentially stick to clothing. i.e. it should preferentially key to dressing over skin, in turn over clothing and other external items. It should be shower proof.

In a particular advantage the sealant is adapted to adhere on curing to previously cured sealant to allow the location and plugging of leaks, or to adhere to skin and dressing about previously cured sealant Preferably the sealant is a TNP sealant which generates or enhances a fluid-tight, preferably an air-tight, seal.

In one embodiment a composition comprises a RTV-2 silicone such as Silpuran®2445 (Wacker) which may optionally be modified to have viscosity and cure as hereinbefore defined. Modification of viscosity and cure is as known in the art and is suitably by incorporating filler such as for example fumed silica or optionally translucent filler or resin or reinforcing resin as hereinbefore defined, to achieve the hereinbefore defined viscosity, or by combining Parts A and B and allowing to pre-react to the hereinbefore defined viscosity before application, or the like. Increasing cure rate is as known in the art, for example increasing the amount of catalyst or reducing the amount of catalyst inhibitor present, if any. Extensibility may be increased by means of additive or by modification of polymers or their reactive sites as hereinbefore described.

A dressing as hereinbefore defined may be any wound dressing, preferably is a wound dressing having a Si wound contact surface, more preferably is Also TNP dressings may be employed, optionally modified to comprise a perimeter region as hereinbefore defined. Known TNP dressings include: Smith & Nephew Disposable Kits for TNP such as Smith & Nephew, RENASYS-F/AB, Abdominal Dressing Kit; Smith & Nephew, RENASYS-F/P, Foam Dressing Kit With Port; Smith & Nephew, RENASYS-G, Gauze Dressing Kit; Smith & Nephew, PICO™ dressing kit; and KCI Kits for TNP including, V.A.C.™ GranuFoam Dressings Kits; and the like. Additional dressings and methods of treating wounds with negative pressure are disclosed in the following applications that are hereby incorporated by reference: U.S. application Ser. No. 13/381,885, filed 30 Dec. 2011 and published as US2012/0116334; U.S. application Ser. No. 12/886,088, filed 20 Sep. 2010 and published as US2011/0213287; U.S. application Ser. No. 13/092,042, filed 21 Apr. 2011 and published as US2011/0282309; U.S. application Ser. No. 12/744,277, filed 20 Sep. 2010 and published as US2011/0028918; and U.S. application Ser. No. 12/744,218, filed 20 Sep. 2010 and published as US2011/0054421, also WO2011/000622, WO 2011/000621, WO2011/135285, WO2011/135286, U.S. Pat. Nos. 7,964,766 and 7,615,036 (all Smith & Nephew) the contents of which are incorporated herein by reference.

Conventional TNP dressings are applied with a drape placed thereover, of which the second face is air-tight. Such dressings can additionally comprise a tissue (wound) contact layer, a negative pressure distribution layer and an optional wound exudate absorbing layer as hereinbefore defined. The PICO™ dressing incorporates an integral air-tight surface and is supplied together with a number of adhesive strips comprised of drape material. The apparatus as hereinbefore defined may optionally omit such strips. The sealant as hereinbefore defined may optionally be applied to the PICO™ dressing without adhesive strips.

Preferably such dressing is characterised by features such as:
  Comprising a wound contact layer and/or tissue contact layer comprising silicone and an open area in an amount and proportion sufficient to inhibit scar tissue formation when NPWT is applied at the wound site preferably comprising silicone and an open area comprising around 20% or less of an overall area of the wound contact layer.

In a particular advantage the dressing is part of an apparatus for applying negative pressure to a wound, comprising: a dressing configured to be placed over the wound and to create a substantially fluid impermeable seal over the wound; a source of negative pressure configured to be coupled to the dressing; and a controller configured to:
  activate the source of negative pressure;
  monitor a plurality of duty cycles of the source of negative pressure over a plurality of consecutive and equal time durations; and
  determine if a duty cycle of the plurality of duty cycles exceeds a duty cycle threshold.

The sealant preferentially adheres to the dressing, at any part of its skin and/or wound contacting surface, border region and/or top surface thereof or part thereof. The dressing for example may comprise a border region, wherein the sealant preferentially adheres to the border region. The skin contact surface may be provided on a first face of the wound cover or dressing, to be applied inwardly to a wound site, and the wound cover or dressing comprises a second face to be applied outwardly, wherein the border region is provided on the second face of the wound cover. Such an arrangement may provide a bead optionally smoother to form a film seal bridging an interface between the dressing and skin about the dressing, including predominantly the skin and second face. Such arrangement may provide additional mechanical strength to the seal.

Alternatively the peripheral region may be provided on the first face of the wound cover or dressing.

Method of Preparation

A further aspect if the preparation of a composition as hereinbefore defined comprising providing polymers i) and (ii) and catalyst (iii) and incorporating components to confer properties of viscosity, cure time and tack and optionally additionally elastomeric properties as hereinbefore defined. Methods for preparing curable compositions as hereinbefore defined in 2 or more Parts are known in the art.

A further aspect is a method for preparing a curable composition as claimed in any of claims 1 to 12 comprising the steps of:
  combining polymers (i) and (ii) and catalyst (iii) as hereinbefore defined to form at least one Part A and at least one Part B; and sealing the at least one Part A and at least one Part B in or on respective receptacles or supports suitable for cooperatively dispensing, for example for cooperatively dispensing from a double barrel syringe.

Method of Sterilisation

A further aspect is a method of sterilising the curable composition comprising heating the at least one Part A and at least one Part B sealed in respective thermally stable receptacles or supports at an elevated temperature of 121° C. or more for a period of up to 28 hours, or by irradiating the at least one Part A and at least one Part B wherein polymers (i) and (ii) and catalyst (iii) are apportioned in at least one Part A and at least one Part B in manner such that polymer (ii) is absent from Part A and polymer (i) is absent from Part B or Part B incorporates a trace amount of polymer (i) represented as molar ratio (Si—H unit or moiety)/(alkenyl unit or moiety) of greater than or equal to 2000 with a radiation source selected from the group consisting of gamma, x-ray, and e-beam radiation in effective sterilising dose.

Apparatus

A further aspect is in the form of an apparatus suitable for use in the field of woundcare, comprising a dispensing device having plural barrel(s) or plural cassette(s), advancing means and mixing means, said barrel(s) or cassette(s) comprising the composition as hereinbefore defined such that Parts A and B are contained in respective barrels or cassettes, the device having means for contacting respective Parts.

Preferably mixing means, contacting means and/or advancing means are provided integral with or separate from the device. Mixing means may be static or active. The apparatus may incorporate a dwell chamber for mixed Parts A and B to partially cure to higher viscosity before being dispensed.

Preferably the apparatus is disposable comprising integral barrel(s) or cassette(s).

Preferably the apparatus comprised an applicator for applying composition comprising means to configure composition on application, for example comprising an applicator with integral spreader. A further aspect is in the form of an apparatus for covering a wound site, for use with a sealant composition as hereinbefore defined, comprising a first skin contact surface and/or wound contact surface to be applied inwardly with respect to a wound site and a second cover surface to be applied outwardly with respect to a wound site, wherein a region is provided at the perimeter of the first surface and/or the second surface comprising a surface or coating which is different to the first surface and/or second surface respectively, and which exhibits adhesion to the sealant greater than that of the first and/or second surface respectively to the sealant. The second surface may be polyurethane (high mvt). The perimeter region may be anything which preferentially adheres.

e.g. the peripheral region may be an embossed film having micro embossing in the form of a hatching pattern, indentations or random channels or any suitable pattern that creates peaks and troughs in the surface of the film. Such peak to trough heights may be in the range 0.1 to 30 micron, preferably 0.1 to 20 micron, or 0.5 to 15 micron, or 0.5 to 10 micron, or 0.1 to 5 micron, or 0.5 to 5 micron, or 0.1 to 2 micron. Such embossing may be achieved by running the film between engraved rollers. The rollers present a mirror image pattern to the film. Other techniques may include laser etching or methods of modifying the surface energy of the peripheral region e.g. Corona treatment or plasma treatment of the surface of the material presented at the peripheral region or any techniques known generally in the art for modifying the surface energy of polymers e.g. chemical coatings or oxidants.

The dressing may comprise a perimeter region, at the upper and/or lower face thereof, comprising a textured region such that the adherence of the sealant to the dressing is greater than to skin. Adherence is improved by mechanical keying and is a function of the coarseness and raised nature of the surface structure of the border region of the dressing and to the magnitude of the contact area between sealant and dressing.

The apparatus may comprise an elastomeric sealant at or adjacent a border region of the first face, preferably a skin-compatible gasket having skin wetting properties.

The skin contacting surface of the dressing may be adhesive or non-adhesive, selected from drying adhesive, pressure sensitive adhesive, contact adhesive, hot melt adhesive, multipart adhesive, one part adhesive or other adhesive. Preferably an adhesive is selected from silicone gel, silicone pressure sensitive adhesive, synthetic latex, hydrocolloid, hydrogel, polyurethane, cyanoacrylate, pressure sensitive adhesive, acrylic, hotmelt or other adhesive used for skin contact applications known within the art.

Preferred skin contacting surfaces include acrylic PSA and a silicone gel adhesive.

The wound cover or dressing is flexible to assist in supporting the seal. The dressing may comprise a known wound cover or dressing, modified to comprise a perimeter region as hereinbefore defined, including conventional advanced wound dressings such as Allevyn, Allevyn Adhesive, Allevyn Gentle Border, Allevyn Gentle, Allevyn Ag Gentle Border, Allevyn Ag Gentle, Mepilex, Mepilex Border.

Also TNP dressings may be employed, optionally modified to comprise a perimeter region as hereinbefore defined. Known TNP dressings include: Smith & Nephew Disposable Kits for TNP such as Smith & Nephew, RENASYS-F/AB, Abdominal Dressing Kit; Smith & Nephew, RENASYS-F/P, Foam Dressing Kit With Port; Smith & Nephew, RENASYS-G, Gauze Dressing Kit; Smith & Nephew, PICO™ dressing kit; and KCI Kits for TNP including, V.A.C.™ GranuFoam Dressings Kits; and the like. Additional dressings and methods of treating wounds with negative pressure are disclosed in the following applications that are hereby incorporated by reference: U.S. application Ser. No. 13/381,885, filed 30 Dec. 2011 and published as US2012/0116334; U.S. application Ser. No. 12/886,088, filed 20 Sep. 2010 and published as US2011/0213287; U.S. application Ser. No. 13/092,042, filed 21 Apr. 2011 and published as US2011/0282309; U.S. application Ser. No. 12/744,277, filed 20 Sep. 2010 and published as US2011/0028918; and U.S. application Ser. No. 12/744,218, filed 20 Sep. 2010 and published as US2011/0054421.

Conventional TNP dressings are applied with a drape placed thereover, of which the second face is air-tight. Such dressings can additionally comprise a tissue (wound) contact layer, a negative pressure distribution layer and wound exudate absorbing layer as hereinbefore defined. The PICO™ dressing incorporates an integral air-tight surface and is supplied together with a number of adhesive strips comprised of drape material. The apparatus as hereinbefore defined may optionally omit such strips. The sealant as hereinbefore defined may optionally be applied to the PICO™ dressing without adhesive strips.

The skin contacting surface may comprise a central skin contacting region provided with an adhesive and the perimeter region comprise an adhesive other than that provided on the skin contacting region.

If required these systems may be adapted for use by applying a suitable skin-compatible adhesive at a perimeter region as hereinbefore defined.

Kit and Components Thereof

A further aspect is a kit for use in the field of wound care comprising a dressing for overlying a wound and skin thereabout comprising a first skin and/or wound contact surface, and a skin-compatible sealant wherein:

a) the sealant is a composition as hereinbefore defined; or b1) wherein the first surface is a silicon wound contact layer, and the sealant is adapted to be applied as a discrete or continuous seal bridging an interface between at least a part of the dressing between the periphery of the dressing and skin about the dressing;

b2) wherein the first surface is silicon or silicon based, and the sealant is adapted to be applied as a discrete or continuous seal bridging an interface between at least a part of the dressing between the periphery of the dressing and skin underlying the dressing; or b3) wherein the sealant is provided as a filler, for body topography irregularities, providing a prepared site for application of a dressing;

c) wherein the wound dressing comprises a first skin and/or wound contact surface to be applied inwardly with respect to a wound site, and a second cover surface to be applied outwardly with respect to a wound site, wherein a perimeter region is provided at the perimeter of the first surface and/or the second surface comprising a surface or coating which is different to the first surface and/or second surface respectively, and which exhibits adhesion to the sealant greater than that of the first and/or second surface respectively to the sealant, as hereinbefore defined.

Preferably the kit comprises a dressing for overlying a wound and skin thereabout and a skin-compatible sealant wherein the sealant is a composition as hereinbefore defined and wherein the dressing comprises a first skin and/or wound contact surface to be applied inwardly with respect to a wound site, and a second cover surface to be applied outwardly with respect to a wound site, wherein the first surface is a skin-compatible surface such as a silicone surface or silicone containing surface.

Further features of the kit are as herein claimed. A sealant for b) or c) may for example be selected from a curing system such as a curable two or more part composition comprising a first part and a second part, for example a 2 part composition as hereinbefore defined, epoxy such as two part resins, cyanoacrylates, acrylic, curing silicone systems, polyurethane or polyurethane curing system, polymeric system functionalised with silicone chain linking functional groups, polymeric system functionalised with polyurethane curing functional groups, or non-curing such as a drying system, including a flexible solid or elastomer rendered fluid by the presence of a volatile solvent, such as putty, gels, hydrogels, xerogels, an air-drying silica gel, spray on elastomers such as acrylic water or solvent based. Preferably the sealant comprises silicone or a functional equivalent thereof. Preferably the sealant is selected from curing silicone systems. Curing silicone systems include addition cure RTV-2 silicone systems.

A curing or non-curing sealant composition comprised in a kit as hereinbefore defined may have any relevant properties or characteristics of a novel 2 or more part sealant composition as hereinbefore defined. Preferably the sealant composition is skin-compatible and comprises skin wetting properties and forms an elastomeric fluid-tight seal when dispensed at an interface with skin and a dressing, wherein the sealant adheres to the dressing in preference to skin or has cohesion greater than or equal to its adhesion to skin.

Suitably the sealant adheres to the dressing in preference to skin. The sealant may adhere to any face of the dressing. The top face is typically PU film. The wound contact layer may be adhesive or non-adhesive.

Preferably the sealant adheres to an adhesive face of a dressing skin contact layer selected from an acrylic PSA and a silicone gel skin contacting adhesive, hot melt SiPSA adhesive and the like.

In the case of a TNP therapy kit, the sealant generates or enhances an air-tight seal and the wound cover comprises a drape, of which the second face is air-tight, and a suction port to interface with a negative pressure source.

A dressing is as hereinbefore defined, and may incorporate a perimeter region for enhanced preferential adhesion or may be in form as commercially available, including conventional advanced wound dressings such as dressings as hereinbefore referred including specific provision for management of wound exudates such as Allevyn, Allevyn Adhesive, Allevyn Gentle Border, Allevyn Gentle, Allevyn Ag Gentle Border, Allevyn Ag Gentle, Mepilex, Mepilex Border; infection management dressings such as ACTICOAT, IODOSORB; iv site care dressings such as IV3000, dressings for management of compromised skin about the wound, post operative surgical drapes such as OPSITE, temporary bioskin dressings such as BIOBRANE; also TNP dressings may be employed, including: Smith & Nephew Disposable Kits for TNP such as Smith & Nephew, RENASYS-F/AB, Abdominal Dressing Kit; Smith & Nephew, RENASYS-F/P, Foam Dressing Kit With Port; Smith & Nephew, RENASYS-G, Gauze Dressing Kit; Smith & Nephew, PICO™ dressing kit; and KCl Kits for TNP including, V.A.C.™ GranuFoam Dressings Kits; and the like.

Integrated TNP kits are available in which the wound cover is integral with the additional layers including a tissue (wound) contact layer, a negative pressure distribution layer and an optional wound exudate absorbing layer and the wound cover optionally allows transpiration or liquid evaporation from wound exudate, as for example with the PICO™ dressing.

Some kits comprise a vacuum pump.

Generic Sealant

The sealant component of the kit is a further aspect in the form of any novel sealant composition or known composition for novel use in the field of wound care, for sealing a wound cover comprising a skin-compatible dispensable composition suitable for locating at or about at least part of a wound site, wherein the sealant comprises skin wetting properties and forms an elastomeric fluid-tight seal when dispensed at an interface with skin and a dressing, wherein the sealant adheres to the dressing, in preference to skin or has cohesion greater than or equal to its adhesion to skin.

A further aspect is in the form of a known or novel composition for use in the field of wound care, for filling a skin crevice or the like comprising a skin-compatible composition when dispensed at or about at least part of a wound site, to form a continuous or planar surface for locating a dressing. Preferably the filler comprises skin wetting properties and forms an elastomeric filling, when dispensed to skin about or adjacent a wound. The filler may form a continuous or planar surface for locating a dressing, wherein the filler adheres to the dressing, in preference to skin or has cohesion greater than or equal to its adhesion to skin. Alternatively the filler may act as a bio barrier to prevent contamination of an adjacent wound.

In a particular advantage, the kit, sealant composition and/or dressing or wound cover may be terminally sterile. Techniques are know for sterilising apparatus, such as dry heat, steam, radiation and the like. GB1020005.3, GB 1019997.4 and GB1104512.7 disclose terminally sterilisable 2 part compositions and methods for their sterilisation. Methods include heat sterilisation and radiation sterilisation, in particular gamma, e-beam or x-ray radiation sterilisation. Preferably the sealant is terminally sterilisable or sterile and is sterilized prior to dispensing by heating the first and second parts in a thermally stable receptacle or support at an elevated temperature of 121° C. or more for a period of up to 28 hours, or by irradiating the first and second parts with a radiation source selected from the group consisting of gamma, x-ray, and e-beam radiation with a dose that provides an effective sterility assurance level.

A further aspect is a method for dispensing or releasing, and curing a composition as hereinbefore defined, comprising dispensing into a desired location at curing temperature for curing time.

The composition may be manually mixed and dispensed. Alternatively any form of dispensing device may be employed, for example the composition may be dispensed by means of a cooperative dispensing device cooperatively dispensing, for example by means of a double barrel syringe, for example by activating respective barrels of a double barrel syringe, or loading respective cassettes therefore and activating.

The method may comprise putting sealant down to fill topography and subsequently placing dressing over.

A further aspect is an elastomer comprising a cured composition as hereinbefore defined, METHOD OF USE A further aspect is a method for dispensing a composition having viscosity and tack as hereinbefore defined comprising:

combining Parts A and B of a curable composition as hereinbefore defined thereby initiating cure; whilst the composition has viscosity as hereinbefore defined, dispensing into a location so as to simultaneously contact/overlie an edge of a dressing and skin about said edge, said dressing overlying a wound site and skin thereabout;

after a period corresponding to that defined to reach a level of tack as defined, an elastomeric seal is formed.

A further aspect is a method for sealing a woundcare dressing comprising: positioning a dressing overlying a wound and skin thereabout;

combining Parts A and B of a curable composition as hereinbefore defined thereby initiating cure;

whilst the composition has viscosity as hereinbefore defined, dispensing into a location so as to simultaneously contact/overlie an edge of said dressing and skin about said edge;

after a period corresponding to that defined to reach a level of tack as defined, an elastomeric seal is formed between dressing and skin.

Preferably the composition is dispensed by means of a cooperative dispensing device as hereinbefore defined cooperatively dispensing, for example by means of a double barrel syringe, for example by activating respective barrels of a double barrel syringe, or loading respective cassettes therefore and activating, preferably wherein the syringe incorporates integral means to configure the dispensed sealant, for example an integral spreader head.

Method of Treatment

A further aspect is a method for sealing a dressing or for treating a wound site, of a human or animal subject in need thereof comprising:

dressing the wound site with a dressing,
dispensing a composition at an interface between the dressing and skin thereabout, around at least part of the wound site in manner to seal the interface;
wherein the composition is as hereinbefore defined.

Preferably dispensing a sealant composition is by means of a device as hereinbefore defined for cooperative dispensing.

Preferably the method further comprises adjusting the position of the dressing before the composition is dispensed.

Preferably the sealant is dispensed after dressing the wound site with the dressing.

Preferably the wound dressing is adapted to contain a negative pressure, the method additionally comprising applying negative pressure to the wound site using a source of negative pressure connected to the wound site.

Preferably applying negative pressure is conducted before dispensing sealant.

Preferably applying negative pressure is by means of a portable negative pressure source in fluid communication with the wound dressing located over a wound site.

Preferably the method includes monitoring transmitted negative pressure at the wound against generated negative pressure.

Preferably a dressing is a combination NPWT dressing incorporating drape, functional wound therapy layers and an integral attachment for a negative pressure source, preferably a portable and/or periodic negative pressure source.

A further embodiment relates to a method of treating a wound site, comprising:

applying a dressing to the wound site, wherein the dressing comprises an outer perimeter adapted to be placed in contact with skin surrounding the wound site; and
dispensing a sealant composition to the perimeter of the dressing, wherein the sealant composition cures in intimate contact with and overlying both the dressing at its perimeter and skin surrounding the perimeter, and rapidly attains zero or low tack, preferably rapidly becomes tack-free.

Preferably the sealant composition cures in intimate contact with and overlying one or more discrete points on, sections of or lengths of the perimeter.

Preferably the sealant composition cures in intimate contact with and overlying substantially the entire perimeter and skin thereabout.

Preferably the dressing comprises at its perimeter a skin-contacting face and an outer face to be positioned remote and facing away from the skin wherein sealant composition cures in contact with and overlying the dressing at the outer face thereof.

Preferably the sealant becomes tack-tree at 32 C at a time in the range between 0.5 minutes to 20 minutes from combining or dispensing.

Preferably the method comprises combining at least two pre-polymers to form the sealant.

Preferably the sealant is tack-free when the a finger touch fails to lift a sample thereof as hereinbefore defined.

Preferably a wound packing material is located so as to partially or completely fill the wound site.

Preferably the dressing comprises a substantially fluid-tight drape, and wherein negative pressure is applied to the wound site through or under the drape using a source of negative pressure.

Preferably an aperture is created into or under the drape so as to connect the wound site to the source of negative pressure.

Preferably the dressing is adhered over the wound site with at least an adhesive underside of the dressing or an adhesive disposed on at least an underside of the dressing.

The sealant may be dispensed before the dressing is applied to the wound site.

Preferably the sealant is dispensed after the dressing is applied to the wound site.

For example, the method addresses covering the wound site with a wound cover, and providing a sealant to skin around at least a portion of the wound site; the wound cover contacting the sealant and forming a fluid-tight seal over the wound, wherein the sealant is skin-compatible, and comprises skin wetting properties and provides a seal at the interface with skin and with the wound cover, and preferentially adheres to the wound cover, or has cohesion greater than or corresponding to its adhesion to skin, wherein the skin contact layer of the wound cover is skin-compatible.

The sealant may also protect healthy skin from the damaging effects of wound exudate, although this is a subsidiary objective and may be achieved by alternative means than the sealant.

Providing the sealant may be by means of dispensing a sealant composition as hereinbefore defined by the method as hereinbefore defined.

The method may further comprise adjusting the position of the dressing before the composition is dispensed.

Filler sealant may be provided before or after, preferably before locating dressing.

The sealant may be provided before or after dressing the wound site. Preferably providing the sealant is conducted after dressing the wound site.

Preferably the wound dressing is a substantially fluid-tight dressing or adapted to contain a negative pressure, the method additionally comprising applying negative pressure to the wound site using a source of negative pressure connected to the wound site.

Preferably applying negative pressure is conducted before providing sealant.

Preferably applying negative pressure is by means of a portable negative pressure source in fluid communication with the wound dressing located over a wound site.

The method may include monitoring transmitted negative pressure against generated negative pressure. This may be used to provide the user with feedback during the dressing application. Typically NP is monitored at the pump, or alternatively at end of port.

Preferably the dressing is applied, the NP source activated, pump down initiated, detecting for alarms indicating NP loss, rub down dressing to close off any sites of NP loss, apply sealant at NP loss sites or about dressing edge in general.

The method is preferably a method for TNP treating a wound site, preferably wherein a dressing is a combination TNP dressing incorporating drape, functional wound therapy layers and an integral attachment for a negative pressure source, preferably a portable and/or periodic negative pressure source.

In an advantage, providing the sealant is by means of dispensing a sealant composition, wherein the composition is a fluid that when dispensed forms a material capable of making a substantially fluid-tight seal. This provides admirable wetting properties.

Preferably the method further comprises adjusting the position of the wound cover before the seal is formed.

It is particularly advantageous to dispense sealant after covering the wound site. This has several advantages: it allows the dressing or drape or apparatus as hereinbefore defined to be repositioned. However most importantly and of greatest significance, it allows air leaks to be minimised through smoothing of the border prior to application of the sealant; and the location that the sealant needs to be applied to is readily apparent.

Dispensing may alternatively be conducted before covering the wound site. This is appropriate particularly in cases where repositioning is not envisaged and the location that the sealant needs to be applied to is readily apparent.

Sealant may be applied continuously or in discrete locations. For example sealant may be applied to form a gasket or may be applied at discrete points at the edge of the dressing or drape. Discrete points may be identified as high stress points or repair points. For example points subject to particular stress, or points where rucking of the cover is observed may be sealed. In a particular advantage, applying as discrete points reduces potential trauma in the case that preferential adhesion is not reliable. This reduces the amount of residue that may need to be manually removed before reapplying the wound cover. In a further advantage, applying as discrete points reduces potential trauma in the case that the wound cover is only acceptably skin-compatible, but repeated readjusting and repositioning and reapplication is likely to cause discomfort if not trauma. In the case that the wound cover was inaccurately positioned and repositioning would be preferred, the weak points may be locally strengthened by discrete application of sealant.

Sealant may be applied in any known manner as hereinbefore defined, such as by direct application from a container. Examples include the primary packaging used commercially for the application of topical medication such as creams, foams, gels, lotions and ointments. Containers such as pots, pouches and tubes are known. These may have an orifice or integrated nozzle to aid in the application process, e.g., the INTRASITEGel APPLIPAK, Smith & Nephew.

Application may be by a range of tools known for sealing, such as by pallet knife or syringe, [for a two part curing system that requires mixing, a double barrelled syringe with a static mixing head can be used, additionally a spreader tip to allow spread of material may be used to facilitate positioning (e.g. Double-Syringe Prefilled Delivery System (L-System), Medmix Systems Ag, fitted with static mixer and spreader tip http://www.medmix.ch/L-SYSTEM.html)]. Application may be by spray, wipe, brush, foam, sponge, non-woven. These materials may be part integrated or fully integrated into dressing or applicator, or can allow manual application. [An applicator using a sponge is demonstrated with Chloraprep i.e. http://www.chloraprep.co.uk].

In an advantage the applicator includes an integral spreader. Where material is applied directly to the junction between the skin and the dressing edge it will be advantageous to manipulate this material to ensure optimal placement. An integral spreader will minimise cross contamination when the sealant is manipulated. During the manipulation cross contamination could relate to: contamination of the sealant with a microbiological burden, contamination of the sealant with foreign bodies, contamination of the sealant with chemicals (such chemicals may have an influence on the sealant) and contamination of personnel or equipment with the sealant.

Alternatively a non-spreader applicator may be beneficial . . . .

Where the composition is a curing system chemical contamination may adversely affect the cure process. For example where the composition is a platinum catalysed RTV-2 silicone, contact with latex or nitrile containing gloves could affect the curing. In a medical setting an integral applicator with spreader therefore overcomes the obstacle of a clinician not being able to use a gloved finger (subject to the chemical composition of the glove) to manipulate the sealant, overcomes the possibility of using an ungloved finger, thus eliminating direct hand to patient contact (not only would this approach be inappropriate for most clinical settings, it would likely result with transfer of the curing composition to the clinician's fingertip) and overcomes the requirement to contaminate any other medical devices or implements with the curing composition.

Use of a sterile applicator with integral spreader would allow the sealant application and manipulation to be carried out using aseptic technique.

Where the applicator with integral spreader is sterile this has the advantage of allowing the device to be used in sterile field without the requirements for any secondary, sterile implements to be provided should the clinician wish to manipulate the sealant during application.

Sealant removal is a further consideration. Preferably it should remove substantially in one piece. Preferably the sealant can be removed with adhesion to the apparatus, i.e. dressing or drape.

Preferably the wound cover is a substantially fluid-tight drape or dressing, optionally incorporating means for fluif communication with a source of negative pressure, the method additionally comprising applying negative pressure to the wound site using a source of negative pressure in fluid communication with the wound site.

Preferably applying negative pressure is by means of a vacuum pump in fluid communication with a wound dressing located over a wound site.

Preferably the NPWT method includes monitoring transmitted negative pressure at the wound against generated negative pressure. In a particular advantage embodiments minimise the deviation of transmitted negative pressure from generated negative pressure.

The method may further comprise creating at least one aperture into or under the drape so as to connect the source of negative pressure. Many techniques to connect the source are known in the art.

The method may further comprise placing foam into the wound site as known in the art.

In some embodiments, it may be preferable for the wound site to be filled partially or completely with a wound packing material. This wound packing material is optional, but may be desirable in certain wounds, for example deeper wounds. The wound packing material can be used in addition to the wound dressing. The wound packing material generally may comprise a porous and conformable material, for example foam (including reticulated foams), and gauze. Preferably, the wound packing material is sized or shaped to fit within the wound site so as to fill any empty spaces. The wound dressing may then be placed over the wound site and wound packing material overlying the wound site. When a wound packing material is used, once the wound dressing is sealed over the wound site, TNP is transmitted from a pump through the wound dressing, through the wound packing material, and to the wound site. This negative pressure draws wound exudate and other fluids or secretions away from the wound site.

NPWT has been considered using negative pressure values in the range 0 to −650 mmHg. More preferably in the range 0 to −250 mmHg. It is envisaged that the negative pressure range for the kit may be between about −20 mmHg and −200 mmHg (note that these pressures are relative to normal ambient atmospheric pressure thus, −200 mmHg would be about 560 mmHg in practical terms). More preferably −40 to −200 mmHg. This is the range of set points available on commercially available pumps such as the Renasys pumps (EZ+& GO)). Aptly the pressure range may be between about −40 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

Canisterless NPWT (omitting a dedicated canister to contain wound exudate) has also been considered using negative pressure values in the same range as conventional NPWT. More preferably −40 to −200 mmHg. More preferably −40 to −140 mmHg.

It will be appreciated that according to certain embodiments the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilised. Aptly more complex amplitude/frequency wave forms of pressure flow profiles may also be provided e.g. sinusoidal, sore tooth, systolic-diastolic or the like etc.

Preferably the dressing will be part of a portable NPWT system. The exudate is managed in a portable canister or preferably within the dressing. The negative pressure source is portable or may be connected intermittently. Preferably the skin contact layer is an adhesive silicone gel, other adhesive or combination of adhesive silicone gel and other adhesive.

Advanced NPWT (herein "combination") dressings are described for example in PCT/GB2011/000629, the contents of which are incorporated herein by reference and are hereinbelow described as follows.

A wound contact layer may be present in the form of a polyurethane layer or polyethylene layer or other flexible layer which is perforated, for example via a hot pin process, laser ablation process, ultrasound process or in some other way or otherwise made permeable to liquid and gas, which enables fluid to flow through the layer. The wound contact layer helps prevent tissue ingrowth into the other material of the wound dressing. The perforations are small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer. For example, a lower pressure sensitive adhesive may be provided on the underside surface of the wound dressing whilst an upper pressure sensitive adhesive layer may be provided on the upper surface 103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilised this helps adhere the wound dressing to the skin around a wound site.

A layer of porous material is located above the wound contact layer. This porous layer, or transmission layer, allows transmission of fluid including liquid and gas away from a wound site into upper layers of the wound dressing. In particular, the transmission layer ensures that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalised negative pressure. The layer is formed of a material having a three dimensional structure. For example, a knitted or woven spacer fabric (for example Baltex 7970 weft knitted polyester). Other materials could of course be utilised.

Material constructions are well known which help control moisture flow across the transmission layer. For example, by having a top layer which is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Techniques are known to improve the liquid flow across the transmission layer (that is to say perpendicular to the channel region formed between the top and bottom spacer layers, such as treating the 3D fabric with a dry cleaning agent to help remove any manufacturing products such as mineral oils, fats and/or waxes used previously which might interfere with the hydrophilic capabilities of the transmission layer.

A layer of absorbent material is provided above the transmission layer. The absorbent material which may be a foam or non-woven natural or synthetic material and which may optionally include or be super-absorbent material forms a reservoir for fluid, particularly liquid, removed from the wound site and draws those fluids towards a cover layer. The material of the absorbent layer also prevents liquid collected in the wound dressing from flowing in a sloshing manner. The absorbent layer also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudate flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer may typically be manufactured from ALLEVYN™ foam, Freudenberg 114-224-4 and/or Chem-Posite™11 C-450.

Aptly, the absorbent layer is a layer of non-woven cellulose fibres having super-absorbent material in the form of dry particles dispersed throughout. Use of the cellulose fibres introduces fast wicking elements which help quickly and evenly distribute liquid taken up by the dressing. The juxtaposition of multiple strand-like fibres leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid and increase the transpiration rates of the dressing.

An equilibrium is set up within the dressing core whereby moisture passes from an absorbent layer into a dryer surrounding area and as it hits the top film the film switches and the fluid vapour starts to be transpired. A moisture gradient is established within the dressing to continually remove fluid from the wound bed and ensure the dressing does not become heavy with exudate.

Aptly the absorbent layer may include at least one through hole located so as to underly the suction port.

A gas impermeable, but optionally moisture vapour permeable, cover layer extends across the width of the wound dressing. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer may be sealed to the wound contact layer in a border region around the circumference of the dressing, ensuring that no air is drawn in through the border area, for example via adhesive or welding techniques. The cover layer protects the wound from external bacterial contamination (bacterial barrier) and allows liquid from wound exudates to be transferred through the layer and evaporated from the film outer surface. The cover layer typically comprises two layers; a polyurethane film and an adhesive pattern spread onto the film. The polyurethane film is moisture vapour permeable and may be manufactured from a material that has an increased water transmission rate when wet.

This process of transpiration occurs even when negative pressure has been applied to the wound cavity, and it has been found that the pressure difference across the cover layer when a negative pressure is applied to the wound cavity has negligible impact on the moisture vapour transmission rate across the cover layer.

An orifice may be provided in the cover film to allow a negative pressure to be applied to the dressing. A suction port may be sealed to the top of the cover film over the orifice, and communicate negative pressure through the orifice. A length of tubing may be coupled at a first end to the suction port and at a second end to a pump unit to allow fluids to be pumped out of the dressing.

A filter element that is impermeable to liquids, but permeable to gases may be provided to act as a liquid barrier, and to ensure that no liquids are able to escape from the wound dressing.

In operation the wound dressing is sealed over a wound site forming a wound cavity. A pump unit applies a negative pressure at a connection portion of the port which is communicated through the orifice to the transmission layer. Fluid is drawn towards the orifice through the wound dressing from a wound site below the wound contact layer. The fluid moves towards the orifice through the transmission layer. As the fluid is drawn through the transmission layer wound exudate is absorbed into the absorbent layer.

In the case of a curing, solvent based or otherwise hardening or solidifying sealant, an appropriate delay may be incurred between applying the sealant, applying the apparatus ie drape or dressing, and initiating negative pressure in any desired sequence. The delay depends on the individual system and is suitably no more than several minutes in each case. In most cases these operations may be carried out in immediate succession, ensuring optimum seal, and optimum wicking.

The wound dressing may be sized as necessary for the size and type of wound it will be used in. Combination TNP wound dressings are presized, and are not typically cut to shape, although they are in some cases cut to size, such as Cutiplast, Smith & Nephew #66001464 (4 cm×5 m). Presized TNP dressings include Allevyn non-adhesive (Smith & Nephew #66000663, 70 cm×40 cm), Elastoplast plastic (Elastoplast, 2-3 cm circular diameter), Acticoat ExFix (Smith & Nephew #66800637 3.8 cm hexagonal distance between parallel sides) and the like. TNP wound dressings may be applied as multiples overlapping, to dress oversize wounds or wounds in oversized regions of compromised skin.

It will be understood that according to embodiments the wound contact layer is optional. This layer is, if used, porous to water and faces an underlying wound site. A transmission layer such as a knitted or woven spacer fabric is used to distribute gas and fluid removal such that all areas of a wound are subjected to equal pressure. The cover layer together with the filter layer forms a substantially liquid tight seal over the wound. Thus when a negative pressure is applied to the port 150 the negative pressure is communicated to the wound cavity below the cover layer. This negative pressure is thus experienced at the target wound site. Fluid including air and wound exudate is drawn through the wound contact layer and transmission layer. The wound exudate drawn through the lower layers of the wound dressing is dissipated and absorbed into the absorbent layer where it is collected and stored. Air and moisture vapour is drawn upwards through the wound dressing through the filter layer and out of the dressing through the suction port. A portion of the water content of the wound exudate is drawn through the absorbent layer and into the cover layer and then evaporates from the surface of the dressing.

Upon the application of negative pressure with the pump, the dressing may in some embodiments partially collapse and present a wrinkled appearance as a result of the evacuation of some or all of the air underneath the dressing. In some embodiments, the pump may be configured to detect if any leaks are present in the dressing, such as at the interface between the dressing and the skin surrounding the wound site. Should a leak be found, such leak is preferably remedied prior to continuing treatment.

Treatment of the wound site preferably continues until the wound has reached a desired level of healing. In some embodiments, it may be desirable to replace the dressing after a certain time period has elapsed, or if the dressing is full of wound fluids. During such changes, the pump may be kept, with just the dressing being changed.

A further aspect provides the use of a composition, kit or apparatus as hereinbefore defined for dressing wounds, preferably for negative pressure wound therapy dressing of wounds as hereinbefore defined. The sealant composition, kit and apparatus may be useful for example in sealing medical dressings, for example in restraining egress of wound exudate or ingress of air or infection, or providing a vacuum seal for NPWT application.

Such use includes use on wounds selected from chronic, acute, traumatic, sub-acute and dehisced wounds, ulcers (such as pressure or diabetic), partial-thickness burns and flaps and grafts. These include open, moist, granulating wounds, preferably surgical wounds such as those resulting from excision of ulcers, cancerous tissue such as perianal and perineal wounds and the like. For optimum healing of such wounds, the wound should be prevented from closing in on itself and allowing fluids to accumulate, whilst at the same time allowing the tissue around the wound to progressively contract, and the wound to shrink. Wound filling materials in NPWT therefore function as a type of "stent", supporting the wound and holding it open.

A sealant composition, kit or apparatus is particularly suited for use in clean, aseptic or sterile applications. Preferably the composition, kit or apparatus is rendered sterile, as known in the art or as hereinbefore defined, and packaged within barrier means. Further barrier means provide a barrier to infection, whereby the composition, kit or apparatus is a double wrapped item, this allows for the removal of the first layer of sterile sealed packaging to reveal receptacles or supports such as cartridges for or incorporated in a syringe, adhesive strips and the like, which are completely sterile inside and out, facilitating entry into a sterile environment. The composition omitting a further barrier means would comprise a non-sterile external surface of receptacles or supports and associated barrier means. As it is not possible to sterilise the composition using standard conditions for medical apparatus as hereinbefore described, it would not be possible to take such a composition into a sterile field.

A sealant for medical dressings may be applied in any known or novel manner. WO 00/74738 (Guyuron) discloses use of silicone based RTV-2 compositions to seal wounds i.a to minimise potential infections. The sealant may suitably therefore be used by casting on top of the wound and surrounding skin and allowing to cure.

WO2004/108175 (Molnlycke Health Care AB) discloses use of silicone based RTV-2 compositions to disintegrating skin or skin around wounds i.a to minimise potential infections and protect against harmful effects of wound exudate. The sealant is used by applying to skin about a wound, or to disintegrating skin, applying an adhesive or non-adhesive dressing over the wound and in contact with the sealant and allowing to cure, or by applying to an adhesive or non-adhesive dressing, applying the dressing to a wound and allowing to cure. In either case the dressing is sealed to the skin about the wound. Embodiments present an admirable improvement on these methods by providing the surgeon, clinician or patient with a sterile sealant for use in these known manners or modifications thereof.

In a preferred embodiment, the composition is dispensed at the border of a dressing which has been positioned in place over a wound.

A further aspect provides the medical or non-medical, dental or non-dental use of a kit, sealant or apparatus as hereinbefore defined other than for wound dressing. Such use includes use as dyes; preservatives; gels; foams; aerosols; pharmaceuticals; adhesives; encapsulants; hair/skin care; cosmetic use; dental use; release coatings; coatings; adhesives and sealants; wound care; skin care including scar reduction; cavity care; medical device encapsulation such as electronic device encapsulation for biomedical applications; mould making; orthopaedics; drug delivery systems including antimicrobial systems; haemostatic and pharmaceutical systems; nutrition including manufacture of foodstuffs; aerospace, marine and submarine applications; ecologically sensitive applications; confined or isolated organisms, or their habitats, or confined or isolated medium or atmosphere such as those having low immunity; sterile, clean or aseptic applications; germination or propagation of living matter such as plants or organisms; including manufacture and repair of equipment, apparatus or components for any of the above and in particular aerospace, submarine sterile, clean or aseptic, germination or propagation.

Embodiments have one or more of the following advantages:

Enhanced sealing to reduce air leaks.

Enhanced sealing to reduce ingress of potentially infectious materials (e.g. infection from faecal and urinary contamination at sacral wounds).

Enhanced sealing to reduce exudate leaks.

Allows curved dressing perimeters to be sealed readily.

Sealing of 3-dimensional dressing perimeters following complex body contours enhancing the ability to remove or reduce leaks.

Sealing of overlapping dressings.

Sealing of dressings where the borders conform to body geometries with tight external radii or are otherwise subject to high levels of deformation.

Sealing of systems where the dressing will be subject to a great deal of movement (e.g. neck, shoulder, underarm, elbow, forearm, wrist, hand, groin, knee, ankle, heel, foot).

Mechanical retention over and above sealing

A number of specific embodiments are given hereinbelow, appropriate for conventional Advanced Wound Dressings, conventional NPWT Drapes/Dressings or PICO™ and a sealant as hereinbefore defined.

Embodiment 1 [Continuous Gasket at the Interface Between the Skin and the Dressing Edge]

1. Prepare and clean the skin surrounding the wound area. Any excess hair should be clipped to ensure close approximation to the wound.

2. Using an appropriate dressing for the wound to be treated, as hereinbefore defined, remove the appropriate release handle(s) and anchor the adhesive side of the dressing to the skin. Smooth the dressing over the wound removing the remaining release handle(s) and ensure that the dressing is adhered all around the wound. (see Modified version of the Allevyn Gentle Border Instructions For Use http://global.smith-nephew.com/us/product253615871.htm)

3. Apply the sealant at the interface between the skin and the edge of the dressing such that the sealant forms a continuous gasket between the skin and the entire perimeter of the dressing edge.

In the case of NPWT systems the dressing should be adhered to the wound as in Step 2, negative pressure should be applied and any leaks minimised. Once air leaks have been minimised the sealant should be applied as in Step 3.

The embodiment is illustrated by example in FIGS. 2d to 2g.

Embodiment 2 [Continuous Gasket at the Interface Between the Skin and the Dressing Edge+Retention Strips]

Follow Steps 1 and 2 in Embodiment 1.
3. Retention strips are applied, covering the dressing borders, the sealant and the skin. If sealant is a curing system a time delay may need to be observed here.

In the case of NPWT systems the dressing should be adhered to the wound as in Step 2, negative pressure should be applied and any leaks minimised. Once air leaks have been minimised the sealant and retention strips should be applied as in Step 3.

Embodiment 3 [Localised Sealing at the Interface Between the Skin and the Edge of the Dressing]

Follow Steps 1 and 2 in Embodiment 1.
3. Examine the dressing that extends over the skin from the peri-wound area to the edge of the dressing. Identify any locations where a poor seal could be possible and that are not readily improved by smoothing the dressing down (areas that are difficult to seal, areas with complex body contours, areas where dressing materials overlap, areas with hair, sections of the dressing that have become raised, tented or rucked). Apply the sealant at these discrete points at the interface between the skin and the edge of the dressing.

Figure 2A:
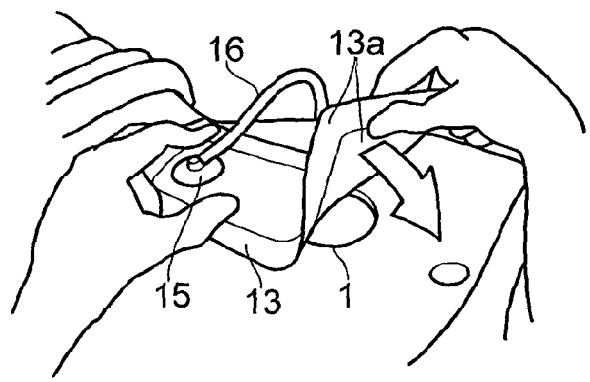
FIGS. 2a to 2k illustrate the application and sealing of an embodiment of a wound cover kit, apparatus and sealant onto a subject.
Figure 2B:
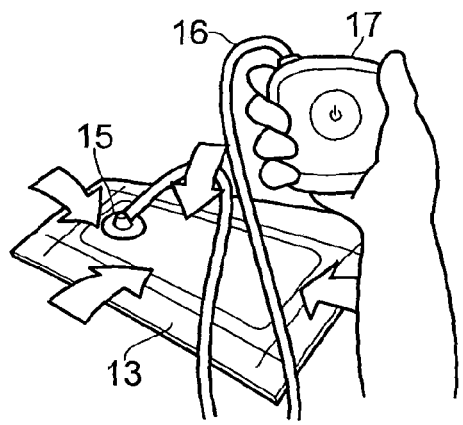
Figure 2C:
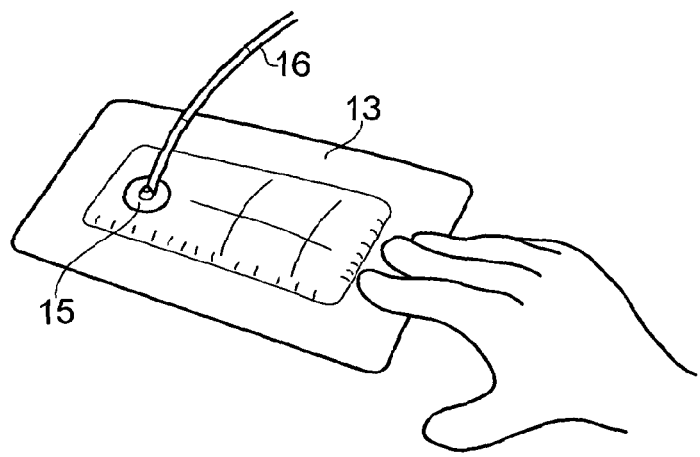
Figure 2D:
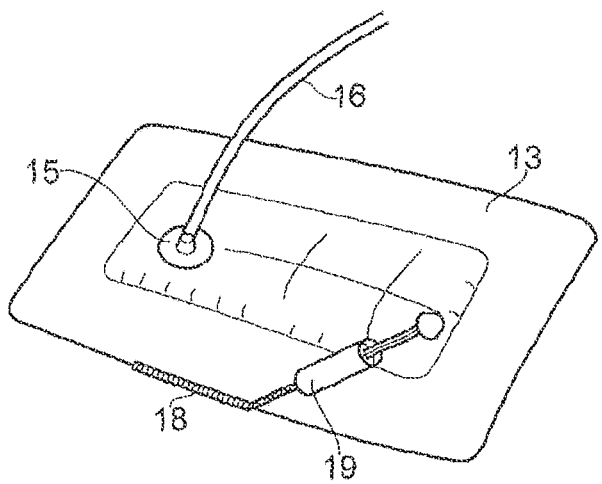
Figure 2E:
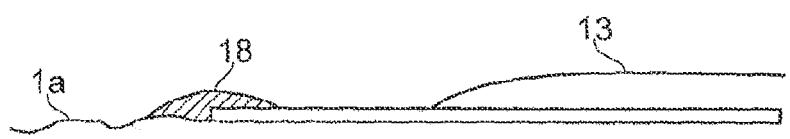
Figure 2F:
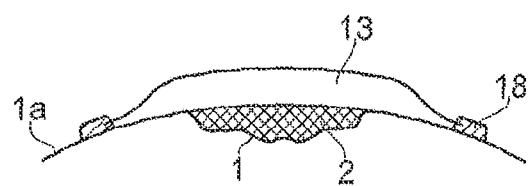
Figure 2I:
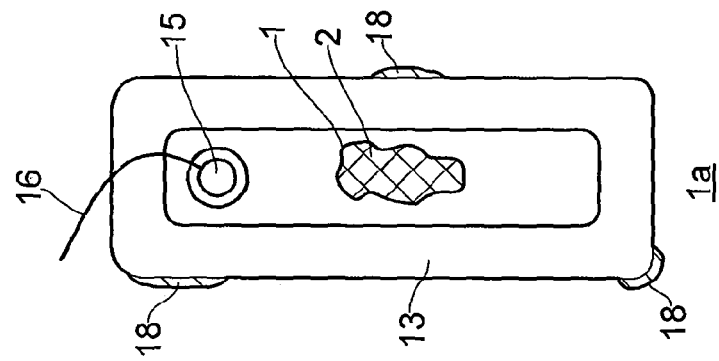
Figure 2H:
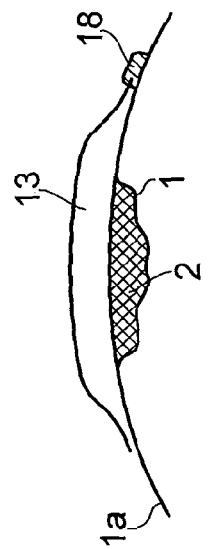

The embodiment is illustrated by example in FIGS. 2h and 2i.

Embodiment 4 [Localised Sealing at the Interface Between the Skin and the Edge of the Dressing+Retention Strips]

Follow Steps 1 and 2 in Embodiment 1.
3. Examine the dressing that extends over the skin from the peri-wound area to the edge of the dressing. Identify any locations where a poor seal could be possible and that are not readily improved by smoothing the dressing down (areas that are difficult to seal, areas with complex body contours, areas where dressing materials overlap, areas with hair, sections of the dressing that have become raised, tented or rucked). Apply the sealant at these discrete points at the interface between the skin and the edge of the dressing.
4. Retention strips are applied, covering the dressing borders, the sealant and the skin.

In the case of NPWT systems the dressing should be adhered to the wound as in Step 2, negative pressure should be applied and any leaks minimised. Once air leaks have been minimised the sealant and retention strips should be applied as in Steps 3 and 4.

Embodiment 5 [Gasket Applied to Skin Under the Skin Contact Layer]

For: Conventional Advanced Wound Dressings, conventional NPWT Drapes/Dressings.
Follow Step 1 in Preferred Embodiment 1.
 1a. Apply the sealant directly to the skin such that the sealant forms a continuous loop of material around the entire perimeter of the wound.
Follow Step 2 in Preferred Embodiment 1.
For: PICO
The dressing will be part of a NPWT system with integrated dressing borders (such as the current PICO dressings) where step 1a must be carried out such that when the continuous loop of sealant is applied directly to the skin at a location where it is only covered by the border of the dressing, when the dressing is subsequently applied.

Additionally retention strips could be applied, covering the dressing borders, the sealant and the skin.

Figure 3B:
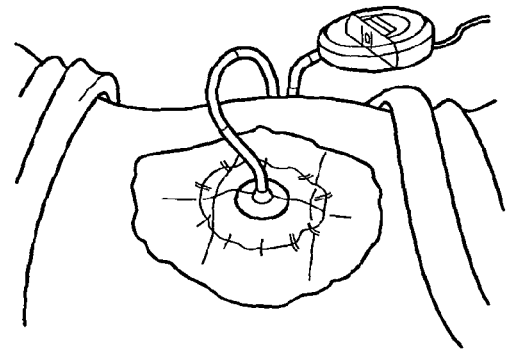
Figure 3B:
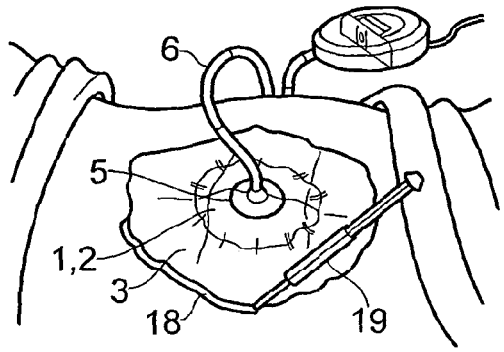
Figure 3B:
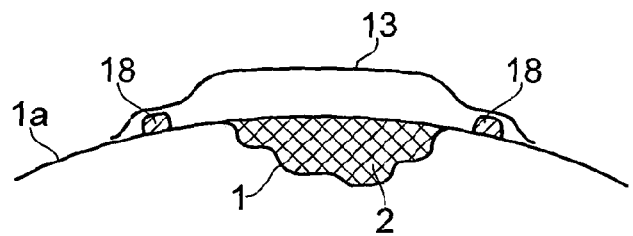
Figure 3C:
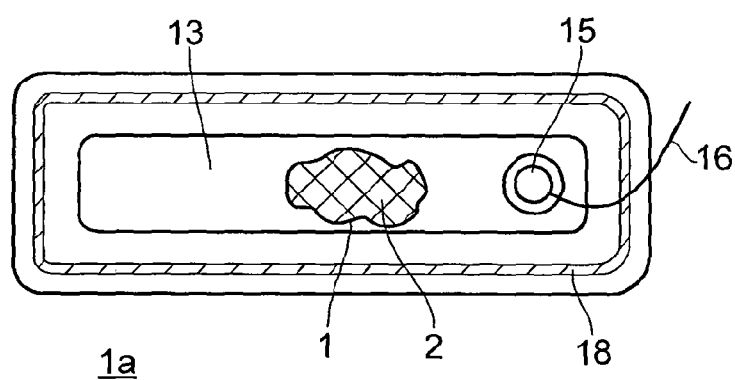

The embodiment is illustrated by example in FIGS. 3b and 3c.

Embodiment 6 [Gasket Applied to Dressing Under the Skin Contact Layer]

For:: conventional Advanced Wound Dressings, any dressing that has a reasonable level of internal rigidity
Follow Step 1 in Preferred Embodiment 1.
2. Using an appropriate dressing for the wound to be treated, having a reasonable level of internal rigidity, remove the appropriate release handle(s). Apply the sealant directly to the skin contacting face of the dressing such that the sealant forms a continuous loop of material proximal to the edge of the dressing. Anchor the adhesive side of the dressing and sealant to the skin. Smooth the dressing over the wound and ensure that the dressing is adhered all around the wound.

Additionally retention strips could be applied, covering the dressing borders, the sealant and the skin.

Figure 1B:
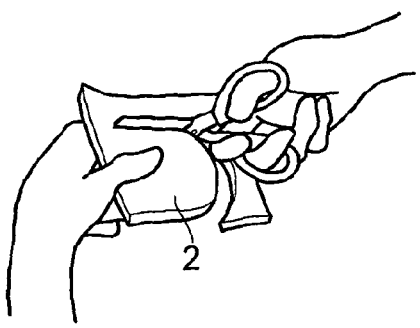
Figure 1C:
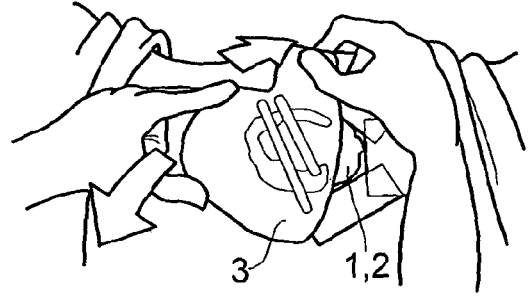

Referring now to FIG. 1a, in conventional foam based NPWT the wound cavity (1) is filled or covered with a porous foam packing material (2) or other wound filler, that may need to be cut to shape (FIG. 1b). Strips (4) may be applied to protect the periwound area. The assemblage is then covered over as shown in FIG. 1c, and sealed with an adhesive flexible sheet (a drape, 3) such as described above that is fairly impermeable to fluids.

Figure 1D:
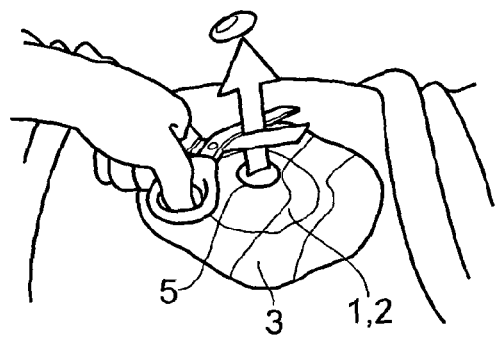
Figure 1E:
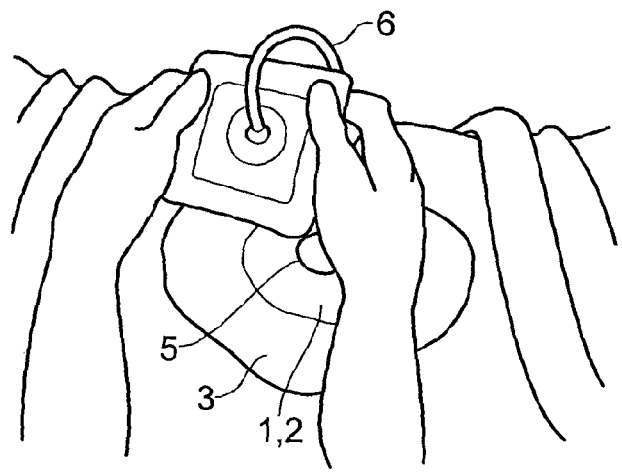
Figure 1F:
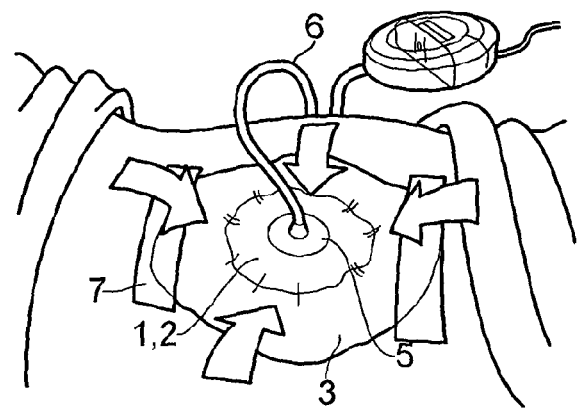

Referring to FIG. 1d, a hole (5) may be cut in the drape (3) to allow for connection of vacuum to the wound site under the drape. Alternatively, vacuum can be connected to the wound site through any sort of aperture or channel under or through the drape (3) into the wound site (1) and optional filler (2). As shown in FIG. 1e, a vacuum line (6) may comprise a conduit or tube that is connected to the hole (5), and may include a port at a proximal end thereof surrounded by an adhesive sheet configured to be adhered to the drape (3) around the hole (5). In other embodiments, the vacuum line (6) can pass through or under the drape (3) and may be received in an aperture or groove in the filler or wrapped in gauze. The distal end (not shown) of vacuum line (6) is connected to a vacuum source (commonly a pump, not shown). In FIG. 1f the wound cavity, enclosed by the drape (3) and tissue, contracts under the force of atmospheric pressure and compresses the packing material or dressing visibly. The system may however be prone to loss of negative pressure. Additional retention strips (7) may be added if required.

In some embodiments (not shown), a sterile foamable composition may be dispensed from a syringe into a wound site. The composition cures once dispensed to form a foamed block contacting the wound bed (1). A drape is placed thereover and sealed in place in conventional manner. A vacuum line is applied to the drape in conventional manner whereupon vacuum may be initiated via a vacuum line. The wound cavity behaves in corresponding manner as described in relation to FIG. 1f. This system improves the fit of the foam filler, and reduces somewhat the stresses placed on the adhesive sealing drape.

Alternatively the foamed block (2) includes a button projecting through aperture (5). The button is broken off to provide an aperture into the foam body. Vacuum line (6) is then coupled to aperture (5) and connected to a vacuum pump in conventional manner.

Figure 1G:
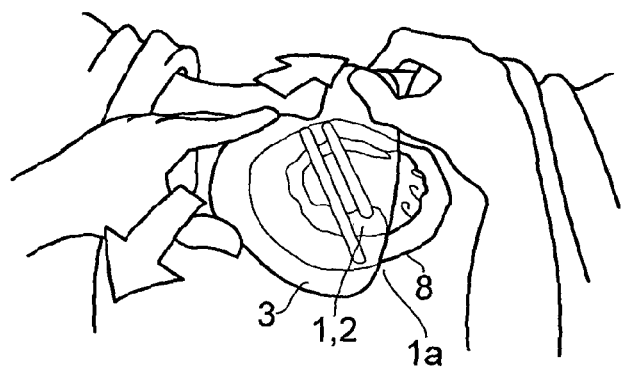

FIG. 1g illustrates a NPWT sealant such as in the embodiments described above. The sealant (8) is applied to skin (1a) about or around a wound site (1), or to disintegrating skin. Adhesive or non-adhesive drape (3) is applied, with optional dressing (not shown) over the wound (1) and in contact with the sealant (8) and the sealant is allowed to cure in contact with the drape (3). Vacuum line (6) is connected to the drape through an aperture in the drape (3) or in any other conventional manner as shown in FIGS. 1d and 1e whereupon vacuum may be initiated. The sealant improves the quality of the negative pressure transmitted to the wound bed. The sealant may be manufactured, prepared, and delivered as described previously.

FIG. 2a shows the aforesaid procedure using a combination NPWT dressing (13) with silicone skin and/or wound contact surface (13a) and integral vacuum port (15) and vacuum line (16). Optional filler (not shown) may be inserted before applying dressing (13). FIG. 2b shows the application of negative pressure by means of portable pump (17). In FIG. 2c is shown the step of smoothing down the dressing border. In FIG. 2d sealant (18) is dispensed at the interface between dressing edge and skin by means of syringe (19) after the dressing (13) is applied. In FIG. 2e the sealant (18) is shown bridging the interface between dressing (13) and skin (1a). This Figure as with all Figures is not to scale. In this Figure in particular it is useful to appreciate the scale of sealant and dressing thicknesses. The PICO border (18) is of thickness approx 0.1 mm. The sealant is disoensed as a bead and conveniently smoothed to a film of corresponding thickness, 0.05-0.15 mm. The between the vacuum chamber and the edge of the dressing (18) extends for approximately 2 to 2.5 cm, and sealant (18) suitably extends for 3 to 5 mm over the skin and a similar distance over the border. The sealant may be manufactured, prepared, and delivered as described previously.

Figure 2G:
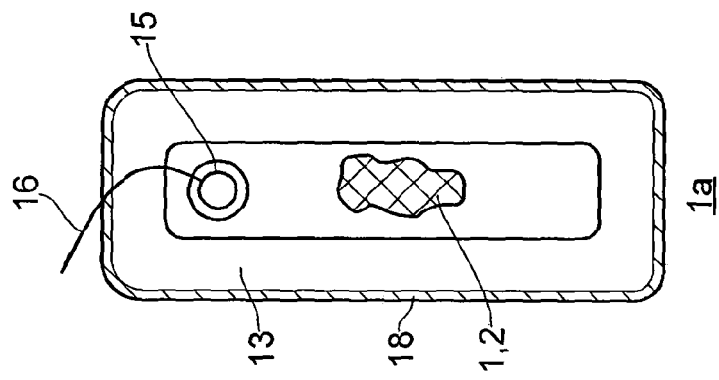

FIGS. 2d to 2i and 3a-3c show variants, relating to dispensing sealant (18) to seal combination dressings/drapes (13) including integral port (15) for vacuum line (16).). The sealant may be manufactured, prepared, and delivered as described previously. For these combination dressings (13) the previously described method (FIG. 1g) of dispensing the sealant (18) to the region of skin (1a) which will underly the border region of the drape (3) that will contact intact skin, may be very imprecise to judge. In the case that it is difficult to prejudge where this border region will contact the skin (1a), dispensing about the edge of the combination dressing (13) is advantageous, as in FIGS. 2d through 2i. The sealant (18) may be applied over the entire perimeter of the dressing as shown in FIGS. 2f and 2g, or sealant (18) may be dispensed at the edge of the drape at positions where loss of negative pressure can be observed or is suspected as in FIGS. 2h and 2i.

Figure 2J:
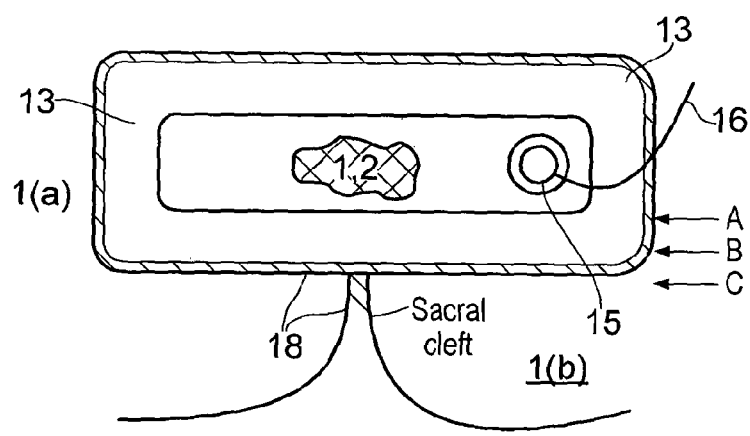
Figure 2K:
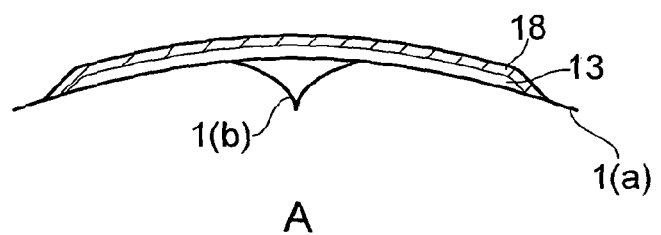
Figure 2K:
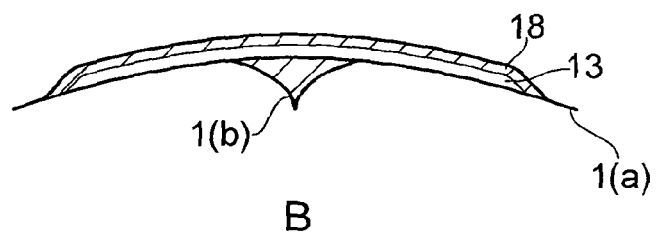
Figure 2K:
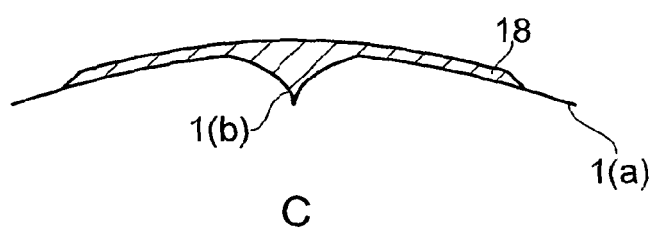

Referring now to FIG. 2j, sealing at a wound adjacent irregular body topography is illustrated. The wound is a sacral ulcer, and the dressing overlies, in part, the sacral cleft (1b). This is a source of gross negative pressure leakage, which requires contouring the dressing into the cleft, in turn compromising the seal at the opposing side of the perimeter of the dressing. The dressing is applied in manner as illustrated in FIGS. 2a to 2c. In FIG. 2j however sealant (18) is dispensed, following the method of FIG. 2d, at the interface between dressing edge and skin by means of syringe (19) after the dressing (13) is applied. In this case sealant (18) is also dispensed into the cleft (1b) underlying and/or protruding from the dressing (13) as a filling of backfilling. In FIG. 2k the sealant (18) is shown filling the cleft (1b) where there is no interface between dressing (13) and skin (1a). In The sealant may be manufactured, prepared, and delivered as described previously.

In FIGS. 3a-i and 3a-ii sealant (18) is applied to a conventional NPWT drape at its edge using an applicator (19) having a spreader head to smooth sealant over both surfaces to be sealed. Sealing may be between skin and dressing interface or dressing and dressing. In all cases sealant will however be applied to the outside face of the dressing.

Alternatively sealant (18) may be dispensed directly to the combination dressing, illustrated in FIGS. 3b and 3c, as a gasket (18), and the dressing then applied over the wound. In all cases, adhesive tape strips (7) can be overlaid to ensure both adhesion and seal are satisfactory. In all cases, curing, sealing and operation of the vacuum are as previously described.

It is to be noted that further details of the methods, compositions, and apparatuses of treating a patient described in other parts of this description may be incorporated with the description of the figures herein.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. Details of any foregoing embodiments should not be considered to be limiting unless expressly indicated as such. Embodiments may relate to any novel one, or any novel combination, of the features disclosed in this specification (including any accompanying claims, abstract and drawings), or to any novel one, or any novel combination, of the steps of any method or process so disclosed.

Herein either a full stop or comma is used as the decimal marker.

The reader's attention is directed to all papers and documents which are filed concurrently with or previous to this specification in connection with this application and which are open to public inspection with this specification, and the contents of all such papers and documents are incorporated herein by reference.

EXAMPLES

The following Examples are given as non-limiting illustration.

Compositions

RTV-2 Si compositions having 2 Parts incorporating i), ii) and iii) as defined above, literature values of physical properties are shown in Table T1, experimental values in Tables T2:

Comparison—Prior Art:

P1 Cavi-Care™ (20 g), Part A and Part B Polymers Product Code 4563 (Smith & Nephew).

This is a commercially available foaming in situ dressing.

P2 Mepiseal™ (3 ml), Part A and Part B Polymers Ref. 283100 (Mölnlycke

This is a commercially available dispensable adhesive sealant intended to seal wound exudates within a wound area from contacting intact skin.

P3 Silpuran® 2450 Part A and B Polymers Ref 60063054 and 60063056 (Both Wacker Chemie A G).

This is a commercially available elastomer for casting as alignment, shock, damping members etc in prosthetics.

Example—According to Claims

I1 Silpuran® 2445 A/B Part A and B polymers Ref 60063054 and 60063056 (both Wacker Chemie A G).

This is a commercially available elastomer for casting as alignment, shock, damping members etc in prosthetics.

TABLE T1

| | P1 | P2 | P3 | I1 |
|---|---|---|---|---|
| Viscosity (after stirring) measured in accordance with DIN EN ISO 3219, Plate/Cone, D = 10 s$^{-1}$ (Pa.s) | — | — | Part A = 35.000 Part B = 20.000 | Part A = 10.000 Part B = 10.000 |
| Hardness Shore A of cured material (curing conditions of 10 minutes & 135° C.) measured in accordance with ISO 868 | — | — | 50 | 40 |
| Tensile strength of cured material (curing conditions of 10 minutes & 135° C.) measured in accordance with ISO 37 (N.mm$^{-2}$) | — | — | 6.00 | 6.00 |
| Elongation at break of cured material (curing conditions of 10 minutes & 135° C.) measured in accordance with ISO 37 (%) | — | — | 200 | 400 |
| Tear strength of cured material (curing conditions of 10 minutes & 135° C.) measured in accordance with ASTM D 624 B (N.mm$^{-1}$) | — | — | 7 | 15 |

Example T2—Parameter Testing

Samples were assessed to determine whether their parameters are suitable as a composition as hereinbefore described. Results are shown in Tables T2

Temperature

For Extensibility, Permanent Set, Tensile, Elongation at Break and Probe Tack tests the environment was conditioned to a temperature of 20° C.±2° C. and a relative humidity of 65%±15%. For Viscosity, Manual Kinetic Cure Time and Tack Free Time tests the temperature is specified in each case.

Height of Silicone

From the height measurements recorded in the examples, it was observed that the minimum height of the cured silicone product was 0.07 mm and the maximum was 1.58 mm. Where recorded the mean heights of the smoothed-edge products ranged from 0.20 to 0.65 mm.

Whilst there is no strict upper or lower limit for the height of the sealant that could be applied, it seems likely that the sealant will be spread with a height in the range 0.01 to 5.00 mm, more preferably in the range 0.05 to 2.00 mm, with the majority of the sealant likely in the range 0.10 to 1.00 mm.

Sample Details

Specimen Preparation for Extensibility, Permanent Set, Tensile and Elongation at Break Tests General guidance on methods and know-how for processing RTV-2 silicones are disclosed in the art (e.g. *Elastosil, Processing RTV-2 silicone rubbers*, 6020e/06.06, Wacker Chemie A G, München).

P1: Parts A and B were dispensed in a 50:50 v/v ratio into a disposable container, vigorously hand mixed for 10 seconds and poured into a flat base PTFE mould. Sufficient material was employed to afford a depth of approx. 5 mm at time of transfer. Removal of large entrained gas bubbles was achieved by pouring the material from height in as thin a stream as possible. The mould was allowed to stand on a horizontal surface for approx. 5 minutes at room temperature. The material was then cured at 135° C. for 10 minutes, allowed to cool and demoulded.

P2: Parts A and B were dispensed in a 50:50 v/v ratio via the integral static mixer present on commercially available Mepiseal units into a flat base PTFE mould. Sufficient material was employed to afford a depth of approx. 5 mm. Where multiple units of Mepiseal were required these were dispensed in rapid succession and within the working time of the material. Immediately after transfer the top of the material was skimmed to afford a flat upper surface. The mould was allowed to stand on a horizontal surface for approx. 5 minutes at room temperature. The material was then cured at 135° C. for 10 minutes, allowed to cool and demoulded.

P3: Parts A and B were dispensed in a 50:50 w/w ratio into a disposable container, vigorously hand mixed for 3 minutes, transferred to a vacuum chamber (set point of 10 mbar) and evacuated. Evacuation was continued until bubble collapse was observed within the catalysed rising mix. At the point of bubble collapse evacuation was immediately discontinued and the material poured into a flat base PTFE mould. Sufficient material was employed to afford a depth of approx. 5 mm. The mould was allowed to stand on a horizontal surface for approx. 5 minutes at room temperature. The material was then cured at 135° C. for 10 minutes, allowed to cool and demoulded.

I1: Parts A and B were dispensed via a 16 element helical static mixer, DN6.5, into a flat base PTFE mould. Sufficient material was employed to afford a depth of approx. 5 mm.

The mould was allowed to stand on a horizontal surface for approx. 5 minutes at room temperature. The material was then cured at 135° C. for 10 minutes, allowed to cool and demoulded.

Method

Viscosity

Figure 4:
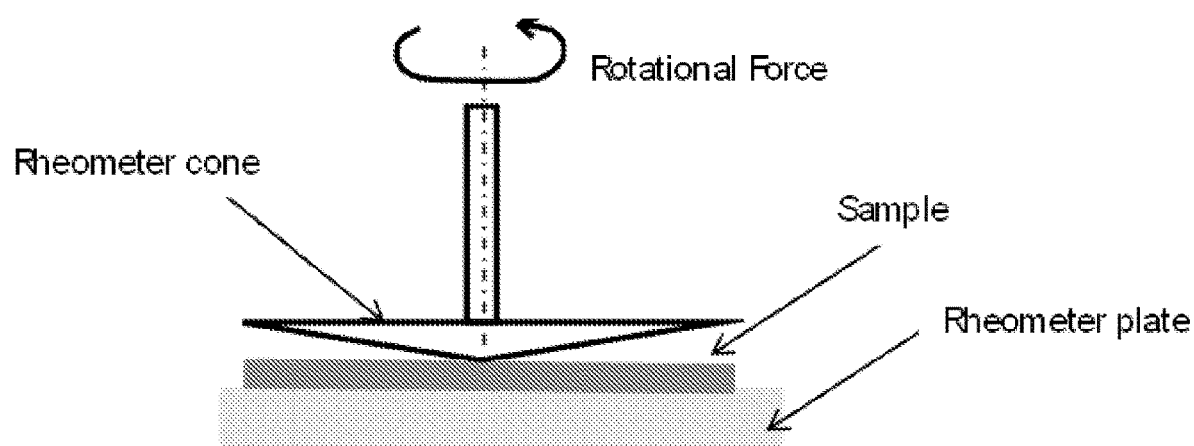
FIGS. 4-7 illustrate experimental instrumentation for testing.

Viscosity is a measure of the resistance of a fluid to deformation by shear or tensile stress and gives an indication of the fluidity of a liquid, suspension or slurry. The viscosity of a sample is measured using a rotational viscometer which simultaneously measures shear rate and shear stress as shown in FIG. 4. Polymers A and B for each of P1, P2, P3 and I1 were independently tested on a cone and plate rheometer, using a 2° steel cone of diameter 60 mm. The samples were tested across a shear rate range of 5-15 s$^{-1}$, at 23° C. in accordance with DIN EN ISO 3219: 1994, Annex B. The viscosity is calculated using the shear stress at a shear rate of 10 s$^{-1}$ and is given in Pa·s.

Calculations $$\text{Viscosity (Pa·s)} = \frac{\text{Shear stress (Pa)}}{\text{Shear rate (s}^{-1})}$$

Assessment of Cure Profile: Manual Kinetic Cure Time and Tack Free Time

Time to reach Manual Kinetic Cure Time and Tack Free Cure Time (or more descriptively zero to low tack) was assessed. All materials, contact apparatus and the environment of the test area were allowed to thermally equilibrate at the specified temperature of the test (minimum conditioning period of 1 hour) prior to dispensing into a Petri dish. P1, P3 and I1 were dispensed from pre-filled 50:50 v/v double barrelled syringes via 16 element helical static mixers, DN6.5. P2 was dispensed via the integral static mixer on the primary packaging it was supplied in. The composition was rapidly dispensed as a line across the diameter of the Petri dish and time t=0 was taken as the end of this procedure.

Periodic testing was conducted by lightly and briefly touching a finger to the surface of the sample in the Petri dish. The sample was assessed for the transition from a material that transferred to the finger when touched to a material that when touched was observed not to transfer material to the finger. The time taken to reach this point was recorded and defined as the Manual Kinetic Cure Time. Periodic testing continued following the Manual Kinetic Cure Time to assess the time taken to reach "tack free". When the tack of the sample had dropped to a point that the assessor was able to lightly place the pad of one chosen finger on top of the material for 1 second and gently raise it vertically away from the sample without causing any disturbance to or lift of the Petri dish, this was recorded and defined as the Tack Free Time.

To minimise the inherent subjectivity with these test the same assessor carried out all of the cure profile assessments. In all cases the Tack Free Time was assessed using the pad of the middle finger of the right hand. To determine the nominal skin contact area employed a fine, inorganic powder was dusted over a high contrast surface and the assessor carried out one Tack Free Time assessment on this model. The impression made was imaged and area determined using Image Pro Plus v6.6 image analysis software (Media Cybernetics Inc, USA) by means of greyscale thresholding. The contact area was determined as 189 mm². The combined mass of each sample and Petri dish was found to be in the range 8 g and 10 g.

The significance of the substrate should be underscored and drawing any direct correlations between the interactions of a material with skin and the interactions of the same material with steel should be done with caution. Moreover the variation in human skin from person to person, or indeed the same person exposed to different environmental conditions can be significant (I. Webster and P. J. West, Adhesives for Medical Applications, in Polymeric Biomaterials, Revised and Expanded, ed. S. Dumitriu, Marcel Dekker Inc., 2$^{nd}$ edn., 2001, ISBN 9780824705695 pp. 706).

Probe Tack Test

Figure 5:
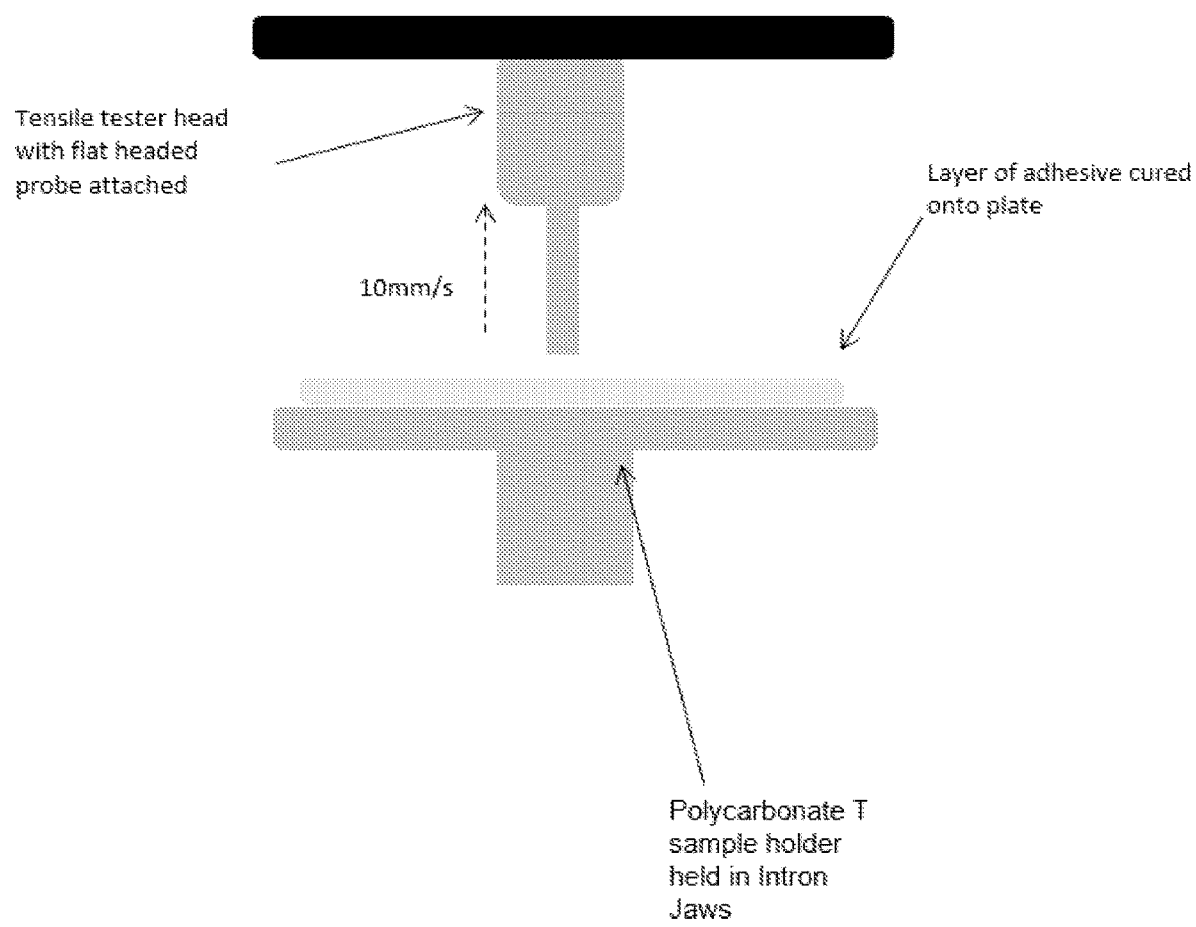

Tack is a measure of the bond formed rapidly when a material is brought into contact with another surface. The testing was based upon the standards set out in ASTM D2979-01. Approximately 2 mm deep slabs of material were dispensed onto a polycarbonate sample holder as shown in FIG. 5. The top was smoothed to create a flat surface and the well-mixed samples (50:50 v/v) were cured at 37° C. for 24 hours. A clean stainless steel rod of surface finish 13 µm rms was brought into contact with the sample at a rate of 10 mm/s for a dwell time of 1 s. The probe was separated from the sample at 10 mm/s and the maximum force to separate the probe from the sample was recorded. The tack is given as the force per cross-sectional area of sample in contact with the probe. Measurements were made along the length of two separately cured samples and treated as one data set.

Calculations $$\text{Tack (kgfcm}^{-2}) = \frac{\text{Separation force (kgf)}}{\text{Probe area (cm}^{-2})}$$

Extensibility and Permanent Set

Extensibility gives an indication of the conformability of a dressing and measures how easy it is to stretch the product by 20%. It was performed using the standard test method BS EN 13726-4 "Test methods for primary wound dressings—Part 4—Conformability".

Figure 6:
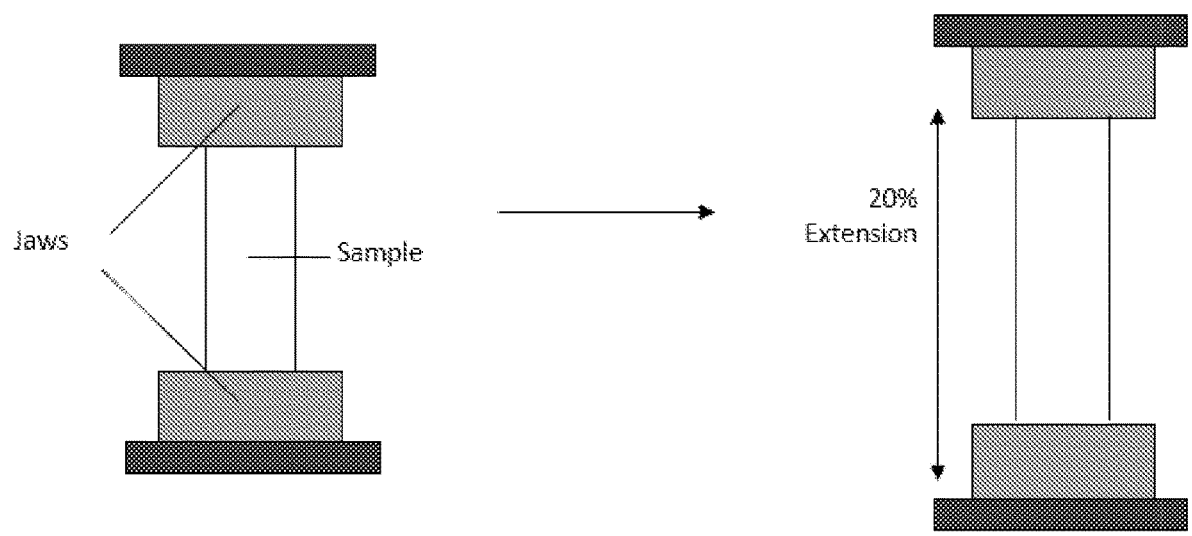

A sample was placed between two jaws of a tensile tester and pulled apart at a constant rate (300 mm/min) until an extension of 20% was reached as shown in FIG. 6. At this point, the force required to stretch the product was measured, and recorded as kgfcm$^{-2}$.

Calculations $$\text{Extensibility (kgfcm}^{-2}) = \frac{\text{Load to produce a 20\% extension (kgf)}}{\text{Sample width (cm)} \times \text{Sample thickness (cm)}}$$

$$\text{Permanent set (\%)} = \frac{\text{Final length (cm)} - \text{Initial length (cm)}}{\text{Initial length (cm)}} \times 100$$

Tensile Strength and Elongation at Break

Tensile strength is a measure of the force required to break a sample of material. Elongation at break is the breaking point of a sample expressed as a % increase in length. The testing was performed using the standard test method BP1993 Appendix XX E "Minimum Breaking Load—Method 1".

Figure 7:
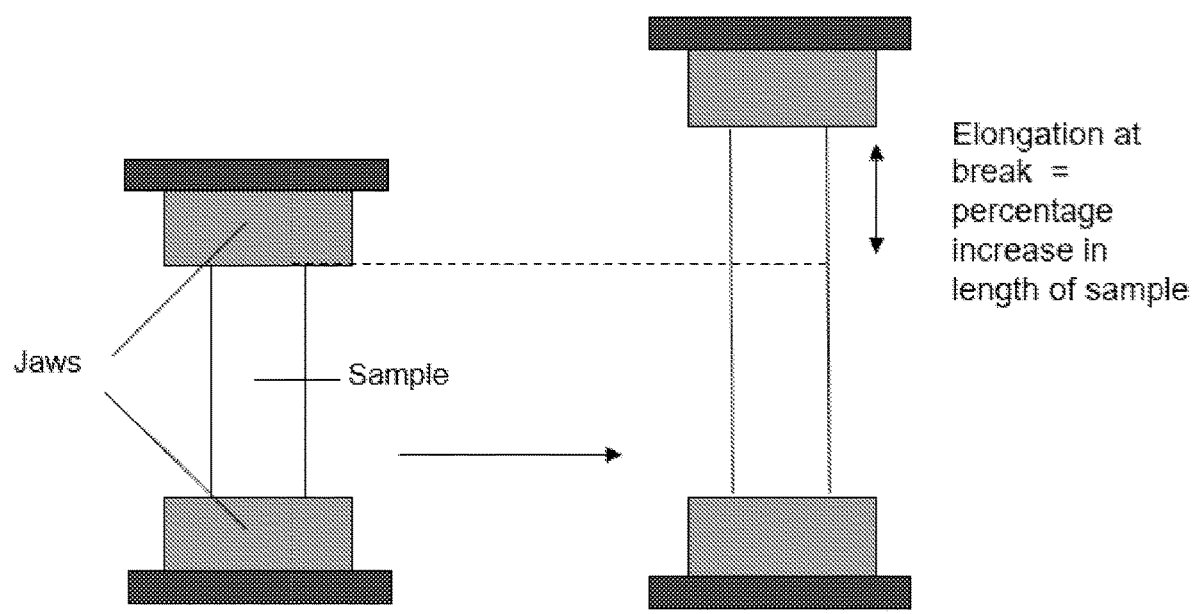

A sample was placed between two jaws of a tensile tester and pulled apart at a constant rate (300 mm/min) until the break point was reached as illustrated in FIG. 7. At this point, the force required to break the product was measured and recorded as kgfcm$^{-2}$. The elongation at break was measured and recorded as the percentage increase from the original gauge length.

Calculations $$\text{Elongation (\%)} = \frac{\text{Sample extension (mm)} \times 100}{\text{Gauge length (mm)}}$$

$$\text{Tensile Strength } (\text{kgfcm}^{-2}) = \frac{\text{Load at specified sample extension (kgf)}}{\text{Sample width (cm)} \times \text{Sample thickness (cm)}}$$

Results

TABLE T2

| | viscosity | | |
|---|---|---|---|
| | Viscosity at shear rate of 10/s, T 23° C. (Pa.s) | | |
| | Results | | Mean |
| Cavi-Care Part A | 1.643 | 1.653 | 1.648 |
| Cavi-Care Part B | 1.773 | 1.804 | 1.7885 |
| Mepiseal part from chamber with Text | 42.30 | 41.97 | 42.135 |
| Mepiseal part from chamber without Text | 34.19 | 36.10 | 35.145 |

TABLE T2-continued

| | viscosity | | |
|---|---|---|---|
| | Viscosity at shear rate of 10/s, T 23° C. (Pa.s) | | |
| | Results | | Mean |
| Silpuran 2450A | 79.40 | 76.32 | 77.86 |
| Silpuran 2450B | 25.20 | 24.39 | 24.795 |
| Silpuran 2445A | 26.07 | 20.39 | 23.23 |
| Silpuran 2445B | 11.81 | 12.01 | 11.91 |

Manual kinetic cure time at 20° C.
Manual kinetic cure time at 23° C.
Tack free time at 23° C.
Manual kinetic cure time at 32° C.
Tack free time at 32° C.

Twenty Degrees Centigrade

| Sample description | Manual kinetic cure time at 20° C. | | | |
|---|---|---|---|---|
| | Results | | | Mean |
| P1 | 1 m 29 s | 1 m 25 s | 1 m 20 s | 1 m 25 s |
| P2 | 17 m 38 s | 16 m 13 s | 16 m 8 s | 16 m 40 s |
| P3 | 45 m 11 s | 42 m 51 s | 44 m 17 s | 44 m 6 s |
| I1 | 21 m 14 s | 21 m 1 s | 22 m 53 s | 21 m 43 s |

Twenty Three Degrees Centigrade

| Sample description | Manual kinetic cure time at 23° C. | | | | | | | | | Mean |
|---|---|---|---|---|---|---|---|---|---|---|
| | Results | | | | | | | | | |
| P1 | 1 m 3 s | 1 m 5 s | 1 m 4 s | 1 m 5 s | 1 m 2 s | 1 m 0 s | 1 m 1 s | 59 s | 1 m 4 s | 58 s | 1 m 3 s | 1 m 02 s |
| P2 | 13 m 4 s | | 13 m 5 s | | 12 m 19 s | | 12 m 7 s | | 12 m 39 s | 12 m 39 s |
| P3 | 37 m 42 s | 39 m 0 s | 38 m 47 s | 37 m 2 s | 40 m 24 s | 38 m 12 s | 40 m 36 s | 38 m 49 s |
| I1 | 16 m 28 s | 16 m 36 s | 17 m 8 s | 17 m 10 s | 16 m 50 s | 17 m 27 s | 16 m 56 s |

| Sample description | Tack free time at 23° C. | | | | | Mean |
|---|---|---|---|---|---|---|
| | Results | | | | | |
| P1 | 2 m 11 s | 2 m 10 s | 2 m 4 s | 2 m 17 s | 1 m 48 s | 2 m 06 s |
| P2 | n/a | | | | | n/a |
| P3 | 2 h 56 m 10 s | | 2 h 34 m 32 s | | 2 h 54 m 48 s | 2 h 48 m 30 s |
| I1 | 1 h 1 m 57 s | | 54 m 21 s | | 55 m 46 s | 57 m 21 s |

Thirty Two Degrees Centigrade

| Sample description | Manual kinetic cure time at 32° C. | | | Mean |
|---|---|---|---|---|
| | Results | | | |
| P1 | 26 s | 26 s | 27 s | 26 s |
| P2 | 5 m 14 s | 5 m 5 s | 4 m 35 s | 4 m 58 s |
| P3 | 15 m 6 s | | 13 m 57 s | 14 m 32 s |
| I1 | 5 m 24 s | | 4 m 57 s | 5 m 11 s |

| Sample description | Tack free time at 32° C. | | | Mean |
|---|---|---|---|---|
| | Results | | | |
| P1 | 1 m 25 s | 1 m 12 s | 1 m 13 s | 1 m 23 s | 1 m 18 s |
| P2 | n/a | | | n/a |
| P3 | 40 m 46 s | 42 m 24 s | 44 m 10 s | 42 m 27 s |
| I1 | 20 m 17 s | 17 m 59 s | 20 m 57 s | 19 m 44 s |

-continued

Tack (gfcm$^{-2}$) post cure at 37° C. for 24 hours

| | Results | | | | | | | | | Mean |
|---|---|---|---|---|---|---|---|---|---|---|
| Cavi-Care | 35 | 36 | 11 | 11 | 16 | 8 | 3 | 8 | 14 | 12 |
| | 5 | 3 | 3 | 6 | 14 | 9 | 25 | | 12 | |
| | 23 | 21 | 15 | 9 | 12 | −1 | 0 | | 9 | |
| Mepiseal | 476 | 479 | 501 | 548 | 490 | 485 | 566 | 468 | 458 | 570 |
| | 486 | 815 | 659 | 785 | 428 | 473 | 462 | | 750 | |
| | 1003 | 859 | 611 | 494 | 499 | 484 | 488 | | 485 | |
| Silpuran | 167 | 175 | 130 | 112 | 166 | 165 | 144 | 122 | 193 | 125 |
| 2450 | 141 | 114 | 118 | 104 | 98 | 100 | 100 | | 103 | |
| | 119 | 117 | 114 | 111 | 97 | 106 | 98 | | 114 | |
| Silpuran | 40 | 85 | 76 | 79 | 76 | 72 | 80 | 86 | 93 | 89 |
| | 94 | 87 | 94 | 95 | 100 | | 95 | 94 | 93 | |
| | 88 | 91 | 93 | 110 | 111 | | 101 | 102 | 90 | |

Extensibility (kgfcm$^{-2}$)

| | Results | | | | | Mean |
|---|---|---|---|---|---|---|
| Cavi-Care | 0.04 | 0.06 | 0.04 | 0.07 | 0.07 | 0.06 |
| Mepiseal | 0.07 | 0.06 | 0.09 | 0.07 | 0.08 | 0.07 |
| Silpuran 2450 | 2.60 | 2.41 | 2.42 | 2.25 | 2.70 | 2.48 |
| Silpuran 2445 | 1.20 | 1.39 | 1.32 | 1.39 | 1.60 | 1.38 |

Permanent Set (%)

| | Results | | | | | | Mean |
|---|---|---|---|---|---|---|---|
| Cavi-Care | 0 | 0 | 0 | 0 | 0 | 0 | |
| Mepiseal | 0 | 0 | 0 | 0 | 0 | 0 | |
| Silpuran 2450 | 0 | 0 | 0 | 0 | 0 | 0 | |
| Silpuran 2445 | 0 | 0 | 0 | 0 | 0 | 0 | |

Tensile Strength (kgfcm$^{-2}$)

| | Results | | | | | Mean |
|---|---|---|---|---|---|---|
| Cavi-Care | 0.24 | 0.27 | 0.26 | 0.24 | 0.29 | 0.26 |
| Mepiseal | 1.64 | 0.95 | 1.77 | 1.69 | 2.00 | 1.61 |
| Silpuran 2450 | 47.64 | 47.64 | 55.85 | 44.37 | — | 48.87 |
| Silpuran 2445 | 37.74 | 39.73 | 39.98 | 41.16 | 37.15 | 39.15 |

Elongation at Break (%)

| | Results | | | | | Mean |
|---|---|---|---|---|---|---|
| Cavi-Care | 92 | 90 | 83 | 73 | 120 | 92 |
| Mepiseal | 425 | 283 | 463 | 450 | 466 | 418 |
| Silpuran 2450 | 199 | 204 | 234 | 184 | — | 205 |
| Silpuran 2445 | 322 | 332 | 334 | 342 | 302 | 326 |

CONCLUSION

Compositions were cast as blocks and beads and inspected for method-related properties and elastomeric properties as follows, wherein √=pass and o=Fail:

| | P1 | P2 | P3 | I1 |
|---|---|---|---|---|
| Viscosity | o | √ | √ | √ |
| Manual Kinetic cure time | √ | √ | o | √ |
| Low-tack time | √ | o | o | √ |
| Low-tack | √ | o | √ | √ |
| Tensile strength | o | o | √ | √ |
| Extensibility | √ | √ | √ | √ |
| Elongation at break | √ | √ | √ | √ |
| Permanent set | √ | √ | √ | √ |

P1, P2 and P3 were found to fail for too low viscosity or too slow to cure or to attain low-tack.

Moreover P1 and P2 failed on elastomeric properties required for seal integrity. P3 and I1 passed on elastomeric properties required for seal integrity and only I1 passed on both elastomeric and method-related properties.

We were surprised to find that low-tack time is considerably greater than cure time at 23 C, and this initially indicated that we would have to seek an alternative solution to the problem addressed herein. However on conducting low-tack time measurements at 32 C, being generally accepted skin temperature, we were further surprised to find a dramatic reduction in low tack time for I1, and to find that we had indeed overcome the problem faced and found a solution.

Examples A-D: Dispensing to Dressing and Skin

PICO Dressing Under Negative Pressure

Example History

Examples A were conducted initially as controlled experiments on subjects not prepared by shaving or clipping hair. Therefore not truly indicative of theatre conditions, nevertheless a skin assessment had been conducted and experiments were performed on forearm which was deemed not to require shaving or clipping. Examples were conducted for 9 minutes, which was insufficient for full cure but satisfactory indication of ease of dispensing compositions.

Examples B, C and D were conducted as verification of A, performed for 2 hours wear time on subjects having suitable skin surface when non-prepped by shaving or clipping. Where hair was present at the application site, this was found to interfere with results and these results were discarded.

Procedure

Step 0. To clean, dry, intact skin, composition was applied. The composition was dispensed to form a continuous bead of material on the skin in the area where the PICO dressing border was to sit Step 1a/1b To clean, dry, intact skin, if applicable having composition dispensed thereto as Step 0, a dressing was applied:
(a) a PICO dressing (15 cm×20 cm, such as supplied in the kit with product code 66800866 (Smith & Nephew)) or
(b) a retention strip (15 cm×20 cm, such as supplied in the kit with product code 66800866 (Smith & Nephew)).

The dressing was orientated such that the midline of the dressing ran longitudinally along the anterior forearm, with the port distal (d) or proximal (p). NPWT was applied ((a) only) using a PICO pump (such as supplied in the kit with product code 66800866, Smith & Nephew) modified for clinical trials incorporating a data logger. The border area of the dressing was smoothed down to minimise any air leaks ((a) and (b)).

Step 2a. If applicable, four retention strips were applied directly to the junction between the skin and the dressing edge. The strips were applied such that they covered the complete perimeter of the dressing.

Step 2b. If applicable, a continuous bead of composition was applied directly to the junction between the skin and the dressing edge. The material was applied such that it covered the complete perimeter of the dressing.

Step 3. At a given time after the start of the dressing application NPWT was stopped and the complete dressing removed.

Observations were made of quality of performance, shown in Table 1.

Measurements were made and results are shown in Table 2

Procedure Table A & B

| Example | Step 0 sealant under | Step 1a (PICO)/ 1b (strips) | Step 2a strips | Step 2b sealant edge | Step 3 |
|---|---|---|---|---|---|
| A1 | control | — | 1a (d) | 2a | — | 9 min |
| A2 | control | — | 1a (d) | — | — | 9 min |
| A3 | P2 | Y | 1a (p) | — | — | 9 min |
| A4 | P2 | — | 1a (d) | — | 2b | 9 min |
| A5 | P2 | Y | 1b | — | — | 9 min |
| B1 | control | — | 1a (p) | — | — | 2 hrs |
| B1 | control | — | 1a (p) | 2a | — | 2 hrs |
| B2 | control | — | 1a (d) | 2a | — | 2 hrs |
| B2 | control | — | 1a (p) | 2a | — | 2 hrs |

Procedure Table C

In this case each experiment was conducted against a control on the subjects opposing forearm, as C1 control in the Table.

In Step 0 a flexible 10 cm×15 cm template was positioned such that it covered the intended location of a PICO dressing and a continuous bead of composition was applied to the skin approx. 1 cm distant from the template edge.

In the case of Step 0 or Step 2b sealant P2 is provided in a syringe, however for sealant P1, P3 and I1 where indicated (Step 0 syringe, Step 2b syringe) Parts A and B were transferred into the separate chambers of a double barrelled cartridge fitted with syringe cap (50 ml, 1:1, S-System, MedMix Systems Ag, comprised of: dispenser, 50 ml, 1:1/2:1, med, plain, part no. DS 50-01-00M; double barrelled syringe cartridge, 50 ml, 1:1, PP natural, med, part no. CS 050-01-32M; syringe pistons A&B, 50 ml, 1:1, PE natural, Si O-ring, med, part no. KSD 50-01-02SM; syringe cap, 1:1/2:1, PE natural, med, part no. VB 200-SM; 16 element helical static mixer, DN6.5×16,1:1/2:1, green, part no. MB 6.5-16-S). The cartridge pistons were inserted, expelling the air headspaces, so that they were flush with the surfaces of the pre-polymers and locked. The filled cartridge and associated static mixer were allowed to thermally equilibrate at 37° C. prior to use.

In Step 3, on removal of dressing the silicone bead was separated from skin and wound contact layer, the height of the silicone was then measured using digital callipers, in 8 locations, in the region of the centre of each dressing edge and in the region of the centre of each dressing corner.

| Example | Step 0 sealant under | Step 1a (PICO)/ 1b (strips) | Step 2a strips | Step 2b sealant edge | Step 3 |
|---|---|---|---|---|---|
| C1 | control | — | 1a (p) | — | — | 2 hrs |
| C1 | P2 | Y | 1a (p) | — | — | 2 hrs |
| C2 | | | | | | |
| C3 | | | | | | |
| C4 | I1 | syringe | 1a (p) | — | — | 2 hrs |
| C5 | | | | | | |
| C6 | P3 | syringe | 1a (p) | — | — | 2 hrs |
| C7 | | | | | | |

Procedure Table D

Steps as Examples C

In Step 2b smoothed, the bead of silicone was smoothed down using a clean, dry fingertip or the tip of the syringe. The silicone was worked into any visible rucks or creases at the dressing edge. The material was spread such that it afforded overlap on the skin and the top surface of the dressing border.

In Step 2b poured, P1 was dispensed into the supplied mixing pot and the two components vigorously mixed for 15 seconds. The curing silicone foam was carefully poured over the junction between the skin and the PICO dressing edge such that it covered the complete perimeter of the dressing.

Step 3 measurement was not conducted for D8 and D9, D11, D12 and D13

| Example | Step 0 sealant under | Step 1a (PICO)/ 1b (strips) | Step 2a strips | Step 2b sealant edge | Step 3 |
|---|---|---|---|---|---|
| D1 | control | — | 1a (p) | — | — | 2 hrs |
| D1 | P2 | — | 1a (p) | — | 2b bead | 2 hrs |
| D2 | | | | | | |
| D3 | | | | | | |
| D4 | P2 | — | 1a (p) | — | 2b smoothed | 2 hrs |
| D5 | | | | | | |

-continued

| Example | Step 0 sealant under | Step 1a (PICO)/ 1b (strips) | Step 2a strips | Step 2b sealant edge | Step 3 |
|---|---|---|---|---|---|
| D6 | P1 | — | 1a (p) | — | 2b poured | 2 hrs |
| D7 | P1 | — | 1a (p) | — | 2b syringe bead | 2 hrs |
| D8 D9 | I1 | — | 1a (p) | — | 2b syringe smoothed | 2 hrs |
| D10 | I1 | — | 1a (p) | — | 2b syringe smoothed | 2 hrs |
| D11 D12 | P3 | — | 1a (p) | — | 2b syringe smoothed | 2 hrs |

Observations A

TABLE 1 A

Integrity of Seal and Comments/Observations

| | Comments/Observations |
|---|---|
| A1 | Strips were applied and this provided good retention as well as maintaining a good seal. |
| A2 | Application was noticeably faster and removal faster than for Example A1 |
| A3 | It was found that the initial keying of the dressing to the skin was hampered by the presence of the Mepiseal between the skin and the silicone wound contact layer. In the first few minutes the border area had to be continually smoothed down to encourage it to stick down. As the Mepiseal cured adhesion of the border to the skin improved, however edge lift was visible and remained a problem, with significant lift occurring at the dressing corners. Removal of the Mepiseal under the PICO dressing was messy. |
| A4 | It became apparent that the Mepiseal had not adhered particularly well to the dressing edge. Where the dressing was stretched due to rotation of the hand the dressing detached from the cured Mepiseal bead. On removal there was no preferential adhesion of the Mepiseal to the dressing, as such some Mepiseal adhered to the dressing and some adhered to the skin. |
| A5 | No NP testing. Removal was very clean. The Mepiseal adhered preferentially to the acrylic pressure sensitive adhesive and was removed cleanly from the skin. |

A—Conclusions:
1. Where Mepiseal was used on intact skin under a drape bearing an acrylic pressure sensitive adhesive wound contact layer it was found to perform well. The Mepiseal did not disturb the adhesion of the drape. On removal of the drape the Mepiseal was found to preferentially adhere to the drape allowing clean removal from skin.
2. Where Mepiseal was used underneath the border of a PICO dressing it was found that the initial keying of the dressing to the skin was hampered by the presence of the Mepiseal between the skin and the silicone wound contact layer. Until the RTV-2 silicone had cured the dressing border had to be continually smoothed down to encourage adherence. Post cure the adhesion of the dressing border to the skin improved and a reduction in loss of negative pressure was recorded, however edge lift was visible and remained a problem. The complexity of knowing where to position Mepiseal on skin such that it would sit under the dressing border and not under the pad, the significant degree of edge lift encountered and the mess generated on removal would be considered negative attributes for a commercial product.
3. Application of the PICO dressing followed by the Mepiseal at the interface between the skin and the dressing edge had three distinct advantages over applying it under the PICO dressing:
   It allowed the dressing to be repositioned.
   It allowed air leaks to be minimised through smoothing of the border prior to application of the Mepiseal.
   The location that the Mepiseal needed to be applied to was readily apparent (this was not the case where the Mepiseal had to be applied to the skin before the PICO dressing was applied).
   On application of the Mepiseal the PICO dressing was under negative pressure. No flow of material under the dressing border was observed. A more preferable product would have the ability to be drawn under the dressing border by the negative pressure in locations where leaks would otherwise be allowing ingress of air from the external environment.
   When the dressing was challenged across mobile and extensible surfaces of the body the Mepiseal detached from the dressing edge. A more preferable product for this application would adhere to both the dressing and to the skin and would be sufficiently extensible so as to accommodate the movement encountered when applied to dynamic body surfaces.
   The colour of any future sealant should be considered. The white silicone bead formed by Mepiseal did appear aesthetically harsh to the eye, however, it did provide a way of tracking its location and allowed easy location for removal. The use of a translucent silicone in this application should therefore be considered.
   On removal there was no preferential adhesion of the Mepiseal to the PICO dressing 8 to 9 minutes after application, as such some Mepiseal adhered to the dressing and some adhered to the skin. A more preferable product for this application would be removed cleanly from the skin with the removal of the dressing.

Observations B-D

In Table 1B-1D the following notation is used for MI (Mechanical Integrity of Seal):

i) CONTROL: OCCASIONAL LIFTING OF THE DRESSING BORDER was observed during wear. Lifting was most typically observed at the dressing corners.

ii) RETENTION STRIPS: NO LIFTING OF THE DRESSING BORDER OR RETENTION STRIPS was observed during wear.

iii-1) BEAD-UNDER: NO SIGNIFICANT DRESSING BORDER LIFT. Wrinkles and tenting in the border were set in place as the silicone cured.

iii-2) BEAD-UNDER: DRESSING BORDER LIFT ALONG A SMALL PROPORTION OF THE DRESSING EDGE. In these locations the border was raised above the skin from the silicone bead under the wound contact layer outwards to the dressing edge.

iii-3) BEAD-UNDER: DRESSING BORDER LIFT ALONG A SIGNIFICANT PROPORTION OF THE DRESSING EDGE. In these locations the border was raised above the skin from the silicone bead under the wound contact layer outwards to the dressing edge.

iv-1) BEAD/SMOOTHED/POURED-EDGE: NO LIFTING OF DRESSING BORDER was observed during wear: cured silicone adhered to skin, adhered to dressing top film and bridged the gap in between. No failures in the mechanical integrity of this seal were observed.

iv-2) BEAD/SMOOTHED/POURED-EDGE: COHESIVE FAILURE OF THE SEAL ALONG A SMALL PROPORTION OF THE DRESSING EDGE. Cohesive failure was observed as a marked break in the seal during wear. At break, the silicone on the skin remained adhered and the silicone on the dressing remained adhered, however mechanical failure of silicone bridging these two surfaces was clearly visible.

iv-3) BEAD/SMOOTHED/POURED-EDGE: COHESIVE FAILURE OF THE SEAL ALONG A SIGNIFICANT PROPORTION OF THE DRESSING EDGE. Cohesive failure was observed as a marked break in the seal during wear. At break, the silicone on the skin remained adhered and the silicone on the dressing remained adhered, however mechanical failure of silicone bridging these two surfaces was clearly visible.

iv-4) BEAD/SMOOTHED/POURED-EDGE: SEPARATION OF DRESSING FROM SILICONE BEAD. The bead remained adhered to the skin. In anatomical areas where the dressing border was subject to movement and thus extension, the skin adhered bead detached from the dressing. This was typically most noticeable at the dressing corners. The result was a residual skin attached bead that was not physically attached to the dressing in areas subject to movement.

iv-5) BEAD/SMOOTHED/POURED-EDGE: SEPARATION OF BEAD FROM SKIN. The product remained adhered to the dressing. In anatomical areas where the dressing border was subject to movement and thus extension, the dressing adhered product detached from the skin. This was typically most noticeable at the dressing corners. The result was a residual dressing attached product that was not physically attached to the skin in areas subject to movement.

TABLE 1 B

Integrity of Seal and Comments/Observations

| | MI | Comments/Observations |
|---|---|---|
| B1 Controls | i) | It should be noted that the control dressings were being used without retention strips. The location on the forearm was selected in combination with a 15 cm wide dressing to challenge the ability of the variants to retain and seal a PICO dressing contoured around the concave profile of the forearm. As such adhesion of the control dressing borders was dependent on the tack of the silicone wound contact layer. All control dressings stayed in place for the duration of the 2 hour wear time. |
| B1 retention strips | ii) | The secondary retention strips provided both retention and a good seal. |
| B2 retention strips | ii) | As for B1. |

TABLE 1 C

Integrity of Seal and Comments/Observations

| | MI | Comments/Observations |
|---|---|---|
| C2 | iii-3) | As for C1. The mean height of the silicone bead was 0.37 mm (with min. of 0.29 mm and max of 0.47 mm). |

TABLE 1 C-continued

Integrity of Seal and Comments/Observations

| | MI | Comments/Observations |
|---|---|---|
| C3 | iii-2) | As for C1. Dressing border lift occurred at a distal corner near the wrist. The mean height of the silicone bead was 0.73 mm (with min. of 0.35 mm and max of 1.27 mm). |
| C4 | iii-1) | Wrinkles and tenting in the border were set in place as the silicone cured. The seal formed reduced the mean air leak rate, however, the physical presence of the silicone bead under the wound contact layer appeared to promote edge lift. On removal the Silicone bead stayed attached to the dressing wound contact layer, removing cleanly from the skin. The mean height of the silicone bead was 0.49 mm (with min. of 0.37 mm and max of 0.62 mm). |
| C6 | iii-2) | Dressing border lift occurred at both of the distal corners. The seal formed reduced the mean air leak rate, however, the physical presence of the silicone bead under the wound contact layer appeared to promote edge lift. On removal the Silicone bead stayed attached to the dressing wound contact layer, removing cleanly from the skin. The mean height of the silicone bead was 0.71 mm (with min. of 0.34 mm and max of 1.18 mm). |
| C7 | iii-3) | As for C6. Dressing border lift occurred along the distal edge, a portion of the lateral edge and the proximal-lateral corner. The mean height of the silicone bead was 0.79 mm (with min. of 0.48 mm and max of 1.49 mm). |

TABLE 1 D

Integrity of Seal and Comments/Observations

| | MI | Comments/Observations |
|---|---|---|
| D1 | iv-4) | Application of the silicone bead improved the seal when compared to the Control, however, large air leaks were recorded by the pump (at 64-65 minutes and 110-115 minutes) which required the dressing border to be smoothed down by hand to restore the seal between the skin and the dressing where the Mepiseal had failed. |
| D3 | iv-5) & iv-2) | The cure time of the silicone bead was considered too long for applications where it is on an outer surface. The bead was smeared in two locations during cure with concurrent transfer of the silicone onto the opposing contact surfaces. The soft tack of product following cure proved undesirable, the product adhered to clothes and other surfaces that it came into contact with. In one instance where the arm was rested on a hard surface and then moved this caused the dressing to lift from the skin along the length of one edge. The tack of the cured Mepiseal therefore presents a potential failure mode when applied to the top surface of a dressing. Following 2 hours wear, dressing edge lift was observed along one long edge. |

TABLE 1 D-continued

Integrity of Seal and Comments/Observations

| | MI | Comments/Observations |
|---|---|---|
| | | Along the proximal edge the silicone was seen to have been spread during cure and then suffered cohesive failure post cure at this point. The mean air leak recorded by the pump was low. The mean height of the silicone bead was 0.48 mm (with min. of 0.13 mm and max of 0.94 mm). |
| D4 | iv-3) | Silicone transferred to vacuum tube and arm during cure. Tack caused foreign objects to stick to the silicone during wear. During wear cohesive failure was observed at 3 of the dressing corners, along the proximal and along the distal dressing edges. On removal the dressing was removed with the Mepiseal remaining adhered on the skin. This occurred with a tearing of the silicone occurring near the dressing edge. Application of the smoothed Mepiseal increased the mean leak rate when compared to the Control. The mean height of the smoothed silicone was 0.32 mm (with min. of 0.17 mm and max of 0.71 mm). |
| D5 | iv-2) | Silicone transferred to arm during cure. Application of the smoothed Mepiseal increased the mean leak rate when compared to the Control. During wear cohesive failure was visible at the proximal lateral dressing corner. The mean height of the smoothed silicone was 0.20 mm (with min. of 0.07 mm and max of 0.46 mm). |
| D6 | iv-1) | Due to the low viscosity of this product during the early stages of cure and the high curvature of the forearm, direct pouring of the curing silicone onto the target area did not afford the degree of control desired. In order to increase the control of product placement at the target site, the viscosity of the curing silicone was continually assessed with stirring in the mixing pot and the viscosity allowed to rise before it was dispensed. To balance this approach against the relatively short work time of Cavi-Care, two units were mixed and dispensed sequentially. During wear no lifting of the dressing border was seen. The cured silicone adhered to the skin, adhered to the dressing top film and bridged the gap in between. No failures in the mechanical integrity of this seal were observed, however, the mass of silicone employed was significant. The comprehensive seal achieved with this approach was reflected in the pump data. The last pump down occurred at 59 minutes and it should be noted that the overall seal of the system was sufficiently good that the pump did not need to operate again to maintain the pressure within set limits before the trial was terminated at 109 minutes. |
| D7 | iv-1) | The application method employed afforded an improvement in the degree of control during application compared with the hand mixing method described in D6. Nonetheless, due to the low viscosity of this product during the early stages of cure and the high curvature of the forearm, direct application onto the target area saw the silicone flow across areas of the dressing and skin, whilst curing that were unnecessary for the purpose of achieving a seal. |
| | | The comprehensive seal achieved with this approach resulted in no lifting of the dressing border during wear and a significant reduction in the mean leak rate when compared to the control. |
| D10 | iv-5) | On removal good adhesion to skin, subjectively greater peel force required to remove than for D13. During wear adhesive failure of the silicone to skin was observed at a discrete location near the wrist and at a discrete location near the cubital fossa. The mean height of the smoothed silicone was 0.51 mm (with min. of 0.21 mm and max of 0.99 mm). |
| D11 | iv-2) | Cure time far longer than targeted dressing change time (45-60 minute pot life at 23° C.). During wear cohesive failure was observed along approx. ⅔ of the proximal dressing edge near the cubital fossa. No failure in the mechanical integrity of the silicone was observed at any other location on the dressing perimeter. Dressing removed with the bulk of applied product remaining adhered to dressing, entire system removing cleanly from skin in one piece. This was considered advantageous for ease of removal. A white colouration was observed on the skin under the product. This was attributed to either a silicone residue or increased moisture content in the skin. |
| D12 | iv-2) | As D11. During wear cohesive failure was observed along approx. ⅓ of the proximal dressing edge near the cubital fossa. No failure in the mechanical integrity of the silicone was observed at any other location on the dressing perimeter. |
| D13 | iv-3) | Hair at application site, results discarded |

TABLE 2

Leak rate and % reduction in leak rate

| | Mean leak rate (ml $min^{-1}$) | | % reduction in leak rate | Border retention/ seal | Pass/Fail |
|---|---|---|---|---|---|
| | Control | Variant | (%) | integrity[1] | assessment[2] |
| B1-Retention Strips | 1.42 | 0.20 | 86 | + | ✓ |
| B2-Retention Strips | 9.02 | 0.73 | 92 | + | ✓ |
| C2 | 10.13 | 0.08 | 99 | − | ✗ |
| C3 | 1.35 | 0.12 | 91 | +/− | ✓ |
| C4 | 9.34 | 2.71 | 71 | + | ✓ |
| C6 | 0.61 | 0.10 | 84 | +/− | ✓ |
| C7 | 1.31 | 0.34 | 74 | − | ✗ |
| D1 | 8.43 | 1.39 | 84 | − | ✗ |
| D3 | 7.22 | 0.32 | 96 | − | ✗ |
| D4 | 0.71 | 2.08 | −192 | − | ✗ |
| D5 | 0.40 | 0.85 | −115 | +/− | ✗ |
| D6 | 2.81 | 0.47 | 83 | + | ✓ |

TABLE 2-continued

Leak rate and % reduction in leak rate

| | Mean leak rate (ml min$^{-1}$) | | % reduction in leak rate | Border retention/ seal | Pass/Fail |
|---|---|---|---|---|---|
| | Control | Variant | (%) | integrity[1] | assessment[2] |
| D7 | 5.98 | 0.38 | 94 | + | ✓ |
| D10 | 0.59 | 0.06 | 90 | +/− | ✓/χ |
| D11 | 5.44 | 0.12 | 98 | +/− | ✓ |
| D12 | 2.37 | 0.12 | 95 | +/− | ✓ |

[1](+ good,
+/− border line, in the case of D10, failure was at specific high-stress regions, the seal remained intact elsewhere
− bad)
[2](% reduction leak rate ≥50% AND integrity of seal ≥ +/−) (✓pass,
χ fail).
✓/χ borderline Discussion Variations in dressing attachment and the ingress of air associated with this will change significantly from volunteer to volunteer. As such, data on variants should only be compared relative to the control dressing placed on the opposing arm of the same volunteer, during the same time frame. During the trials reported in the examples above regular visual checks were made of the applied product, specifically looking for edge lift of the dressing and signs of mechanical failure of the product. In addition data recorded by the pumps was used to establish if the leak rate had been effectively reduced.

In the case of a composite NPWT dressing such as the PICO dressing described above. Application of the sealant to the skin before application of the dressing was found to be a cumbersome process. To form an effective seal the sealant has to be placed between the border area of the dressing and the skin. The use of a template (or other method) to ensure accurate topographical application of the sealant coupled with the necessary careful positioning and application of the dressing does not afford an intuitive easy to use process for dressing applications. Where the sealant can be transferred to other surfaces it reduces the ability of a dressing with a silicone wound contact layer to be applied and then re-positioned without loss of functionality. In the examples above, whilst many of the variants applied under the wound contact layer reduced the leak rate, they negatively interfered with dressing retention by promoting edge lift.

It was established that the preferred method to apply the sealant was to applying the composite NPWT dressing in line with standard practice: first, apply the dressing, apply negative pressure and then smooth the border down to minimise any air leaks. Second, apply the sealant directly to the junction between the skin and the dressing edge. This approach allows the dressing to be readily applied to the wound, re-positioned if necessary and the seal between the silicone wound contact layer and the skin optimised. The sealant is then able to achieve two key tasks:

retain the dressing and maintain the integral seal between the silicone wound contact layer and the skin
provide a secondary seal In summary P2 was found not to be suitable as it readily suffered cohesive failure when applied to the edge of the dressing. The relatively long cure time and inherent tack of P2 were also undesirable properties for this application.

P1 overcame the problem of cohesive failure but control of this low viscosity product at application was less than optimal for this application.

P3 was observed to afford the best reductions in air leaks. The material had suitably high viscosity to stop significant flow of the curing silicones during application, however, the cure time was far too long.

I1 was found to have improved material and mechanical properties—colour, higher elongation at break, lower shore hardness and higher tear strength. Visually this appeared to provide the best seals.

CONCLUSION

The ideal product for use as a sealant in this application should, adhere well to the skin and adhere well to the top film on the dressing border. The product should be extensible (to readily conform to movement of the skin), have a high elongation at break (to avoid cohesive failure), Ideally the product should have a relatively high viscosity (or be thixotropic) so as to remain in the area applied. However it should still be possible for the product to be ejected from an applicator and conform to any rucks or creases at the dressing edge.

If the product cures, the cure time should be sufficiently rapid that the product does not flow away from the area applied or extend the dressing application time significantly.

Ideally the product should have a high MVTR.

Ideally removal should be atraumatic.

Ideally the product should be translucent for improved appearance.

Ideally the product should not be tacky when cured so as not to adhere to clothing or other surfaces following cure.

Ideally the product should not leave a residue on the skin following removal.

The invention claimed is:

1. A method of treating a wound site, comprising:
applying a wound dressing having a substantially fluid-tight drape to the wound site, wherein the dressing comprises an outer perimeter adapted to be placed in contact with skin surrounding the wound site;
applying negative pressure to the wound site through or under the drape using a source of negative pressure;
monitoring negative pressure at the wound site compared to negative pressure generated at the source of negative pressure or at a port of the wound dressing;
identifying a leak between the wound dressing and the skin about the dressing;
dispensing a sealant composition to at least a portion of the outer perimeter of the wound dressing where the leak occurs, wherein the sealant composition is dispensed to the wound dressing positioned over the wound site such that the sealant composition at least partially overlies the wound dressing at an edge of the wound dressing to form an exposed seal at the edge, wherein the sealant composition cures in contact with both the wound dressing and the skin, wherein the sealant composition is apportioned between at least one Part A and at least one Part B and comprises:
one or more alkenyl-group containing polymers having at least one alkenyl group or moiety per molecule;
one or more SiH-containing polymers having at least one Si—H unit per molecule; and a catalyst for curing by addition of the one or more alkenyl-group containing polymers to the one or more SiH-containing polymers;

wherein dispensing the sealant composition comprises combining Part A and Part B; and curing a combination of Parts A and B to form a seal at the portion of the outer perimeter of the wound dressing where the leak occurs after the wound dressing is positioned over the wound site, wherein the combination of Parts A and B cures in a time between approximately 0.5 min to approximately 25 min and the composition cures to an elastomer exhibiting zero or low tack at a time ranging from approximately 0.5 minutes to approximately 30 minutes.

2. The method of claim 1, wherein the seal is exposed at the edge and provides an air-tight seal between the wound dressing and the skin about the dressing.

3. The method of claim 1, wherein the outer perimeter of the wound dressing comprises a skin-contacting face and an upper face configured to be positioned facing away from the skin, wherein the sealant composition cures in contact with and overlying the upper face of the wound dressing.

4. The method of claim 1, further comprising drawing the sealant composition between the wound dressing and the skin at the location of the leak.

5. The method of claim 1, further comprising dispensing the sealant composition in the form of a bead or film at discrete points, thereby bridging an interface between the wound dressing and the skin.

6. The method of claim 1, further comprising placing a wound packing material within the wound site and applying the wound dressing to the wound site with the wound dressing covering the wound packing material.

7. The method of claim 1, wherein applying the wound dressing comprises adhering the wound dressing over the wound site with an adhesive disposed on an underside of the wound dressing.

8. A method of treating a wound site, comprising:

applying a wound dressing to the wound site, wherein the wound dressing comprises an outer perimeter adapted to be placed in contact with skin surrounding the wound site; and dispensing a sealant composition to at least a portion of the outer perimeter of the wound dressing, wherein the sealant composition is dispensed to the wound dressing positioned over the wound site such that the sealant composition at least partially overlies the wound dressing at an edge of the wound dressing to form an exposed seal at the edge, wherein the sealant composition cures in contact with both the wound dressing at the outer perimeter and the skin at the outer perimeter, wherein the sealant composition is apportioned between at least one Part A and at least one Part B and comprises:

one or more alkenyl-group containing polymers having at least one alkenyl group or moiety per molecule;

one or more SiH-containing polymers having at least one Si—H unit per molecule; and a catalyst for curing by addition of the one or more alkenyl-group containing polymers to the one or more SiH-containing polymers; and wherein dispensing the sealant composition comprises combining Part A and Part B after the wound dressing is positioned over the wound site, wherein a combination of Parts A and B cures in a time between approximately 0.5 min to approximately 25 min and the composition cures to an elastomer exhibiting zero or low tack at a time ranging from approximately 0.5 minutes to approximately 30 minutes.

9. The method of claim 8, wherein the sealant composition cures in contact with and overlying substantially the entire outer perimeter and skin thereabout.

10. The method of claim 8, wherein the outer perimeter of the wound dressing comprises a skin-contacting face and an upper face to be positioned remotely from and facing away from the skin, wherein the sealant composition cures in contact with and overlying the wound dressing at the upper face thereof.

11. The method of claim 8, further comprising applying negative pressure to the wound site through the wound dressing, wherein the cured sealant composition provides an air-tight seal between the wound dressing and the skin.

12. The method of claim 11, further comprising:

identifying at least one location where a leak allows ingress of air between the wound dressing and the skin about the dressing after applying negative pressure; and dispensing the sealant composition to at least the portion of the outer perimeter of the wound dressing at the location of the leak, wherein the cured sealant composition provides the air-tight seal at the location of the leak.

13. The method of claim 8, further comprising placing a wound packing material within the wound site and applying the wound dressing to the wound site with the wound dressing covering the wound packing material.

14. The method of claim 8, wherein the wound dressing comprises a substantially fluid-tight drape, the method further comprising applying negative pressure to the wound site through or under the drape using a source of negative pressure.

15. The method of claim 14, wherein applying negative pressure is performed at least partially before dispensing the sealant composition.

16. The method of claim 15, further comprising monitoring negative pressure at the wound site compared to negative pressure generated at the source of negative pressure.

17. The method of claim 16, further comprising:

identifying a location where a leak allows ingress of air between the wound dressing and the skin about the dressing; and dispensing the sealant composition to at least the portion of the outer perimeter of the wound dressing at the location of the leak.

18. The method of claim 17, further comprising drawing the sealant composition between the wound dressing and the skin at the location of the leak using the negative pressure.

19. The method of claim 8, wherein applying the wound dressing comprises adhering the wound dressing over the wound site with an adhesive disposed on an underside of the wound dressing.

* * * * *